(12) United States Patent
Kodym et al.

(10) Patent No.: US 8,163,709 B2
(45) Date of Patent: Apr. 24, 2012

(54) TAK1-D MEDIATED INDUCTION OF CELL DEATH IN HUMAN CANCER CELLS BY SPECIFIC SEQUENCE SHORT DOUBLE-STRANDED RNAS

(75) Inventors: Reinhard Kodym, Addison, TX (US); Michael Story, Southlake City, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 12/361,311

(22) Filed: Jan. 28, 2009

(65) Prior Publication Data

US 2009/0192118 A1 Jul. 30, 2009

Related U.S. Application Data

(60) Provisional application No. 61/024,076, filed on Jan. 28, 2008.

(51) Int. Cl.
*A61K 48/00* (2006.01)
(52) U.S. Cl. ...... 514/44; 536/24.5; 536/24.1; 536/24.31
(58) Field of Classification Search .................. None
See application file for complete search history.

(56) References Cited

FOREIGN PATENT DOCUMENTS

| WO | WO 02/068579 | 9/2002 |
|----|--------------|--------|
| WO | WO 03/039443 | 5/2003 |

OTHER PUBLICATIONS

Choo et al. TAK1-mediated stress signaling pathways are essential for TNF-alpha-promoted pulmonary metastasis of murine colon cancer cells. Int. J. Cancer 118, 2758-2764 (2006).*
"Homo sapiens mitogen-activated protein kinase kinase kinase 7 (MAP3K7), transcript variant D, mRNA," Accession No. NM_145333, 2006.
Brown et al., "Structural basis for the interaction of TAK1 kinase with its activating protein TAB1," *J. Mol. Biol.*, 354:1013-1020, 2005.
Bulavin et al., "Initiation of a G2/M checkpoint after ultraviolet radiation requires p38 kinase," *Nature*, 411:102-107, 2001.
Cans et al., "Proteasome-dependent degradation of human CDC25B phosphatase," *Mol. Biol. Rep.*, 26:53-57, 1999.
Dempsey et al., "Alternative splicing and gene structure of the transforming growth factor beta-activated kinase 1," *Biochim. Biophys. Acta.*, 1517:46-52, 2000.
Dowdy et al., "HER2/Neu- and TAK1-mediated up-regulation of the transforming growth factor beta inhibitor Smad7 via the ETS protein ER81," *J. Biol. Chem.*, 278:44377-44384, 2003.
Edlund et al., "Transforming growth factor-beta1 (TGF-beta)-induced apoptosis of prostate cancer cells involves Smad7-dependent activation of p38 by TGF-beta-activated kinase 1 and mitogen-activated protein kinase kinase 3," *Mol. Biol. Cell.*, 14:529-544, 2003.

Goss et al., "SAPK/JNK regulates cdc2/cyclin B kinase through phosphorylation and inhibition of cdc25c," *Cell Signal*, 15:709-718, 2003.
Hiscott et al., "Manipulation of the nuclear factor-kappaB pathway and the innate immune response by viruses," *Oncogene*, 25:6844-6867, 2006.
Judge et al., "Design of noninflammatory synthetic siRNA mediating potent gene silencing in vivo," *Mol. Ther.*, 13:494-505, 2006.
Katoh, "WNT/PCP signaling pathway and human cancer (Review)," *Oncology Reports*, 14:1583-1588, 2005.
Kodym et al., "Sequence-specific activation of TAK1-D by short double-stranded RNAs induces apoptosis in NCI-H460 cells," *RNA*, 14:535-542, 2008.
Kuma et al., "BIRB796 inhibits all p38 MAPK isoforms in vitro and in vivo," *J. Biol. Chem.*, 280:19472-19479, 2005.
Ninomiya-Tsuji et al., "The kinase TAK1 can activate the NIK-I kappaB as well as the MAP kinase cascade in the IL-1 signalling pathway," *Nature*, 398:252-256, 1999.
Sakurai et al., "TAK1-TAB1 fusion protein: a novel constitutively active mitogen-activated protein kinase kinase kinase that stimulates AP-1 and NF-kappaB signaling pathways," *Biochem. Biophys. Res. Comm.*, 297:1277-1281, 2002.
Sakurai et al., "Phosphorylation-dependent activation of TAK1 mitogen-activated protein kinase kinase kinase by TAB1," *FEBS Lett.*, 474:141-145, 2000.
Schultz and Nigg, "Identification of 21 novel human protein kinases, including 3 members of a family related to the cell cycle regulator nimA of Aspergillus nidulans," *Cell Grow. Diff.*, 4:821-830, 1993.
Singhirunnusorn et al., "Critical roles of threonine 187 phosphorylation in cellular stress-induced rapid and transient activation of transforming growth factor-beta-activated kinase 1 (TAK1) in a signaling complex containing TAK1-binding protein TAB1 and TAB2," *J. Biol. Chem.*, 280:7359-7368, 2005.
Zamanian-Daryoush et al., "NF-kappaB activation by double-stranded-RNA-activated protein kinase (PKR) is mediated through NF-kappaB-inducing kinase and IkappaB kinase," *Mol. Cell. Biol.*, 20:1278-1290, 2000.
Zhao et al., "Disruption of the checkpoint kinase 1/cell division cycle 25A pathway abrogates ionizing radiation-induced S and G2 checkpoints," *Proc. Natl. Acad. Sci. USA*, 99:14795-14800, 2002.

* cited by examiner

*Primary Examiner* — Kimberly Chong
(74) *Attorney, Agent, or Firm* — Fulbright & Jaworski

(57) ABSTRACT

The splicing variant D of the TAK1 gene is activated by short double-stranded RNAs in a sequence specific manner. Activation of TAK1-D leads to the downstream activation of the p38 MAPK and of SAPK/JNK but not the NFκB pathway. The current invention therefore provides a method of inducing apoptosis and/or cell cycle arrest in a cancer cell comprising contacting said cell with an agonist of Tak1-D function. The invention further provides a method of modulating inflammation and the treatment of cancer by the administration of an agonist of Tak1-D function or expression. In yet another aspect, the invention provides a method of inducing p38 MAPK and SAPK/JNK signaling in a cell comprising contacting said cell with an agonist of Tak1-D function or expression.

11 Claims, 27 Drawing Sheets

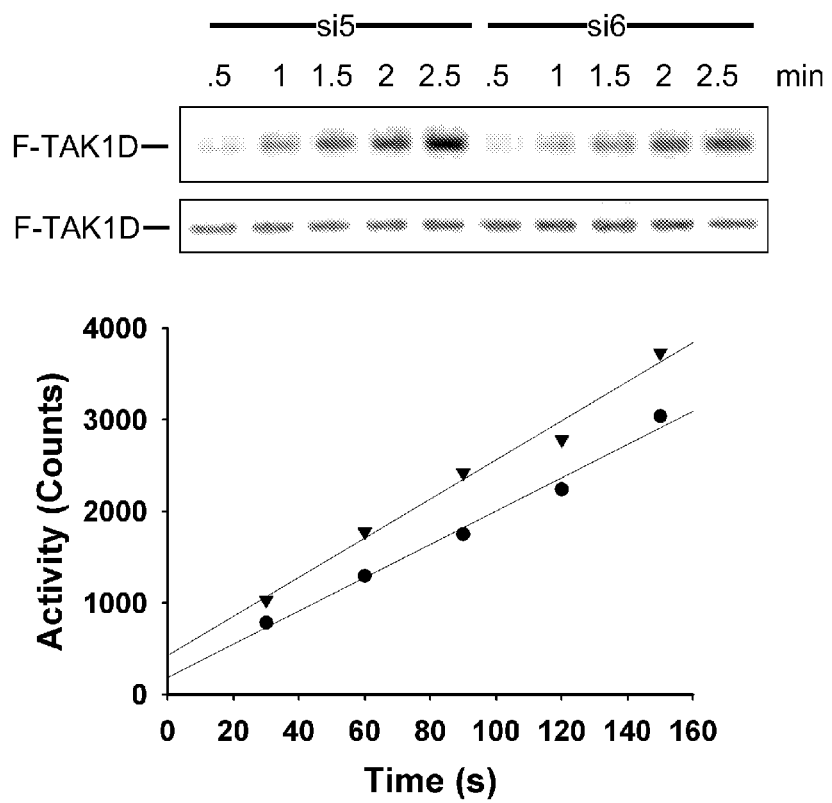
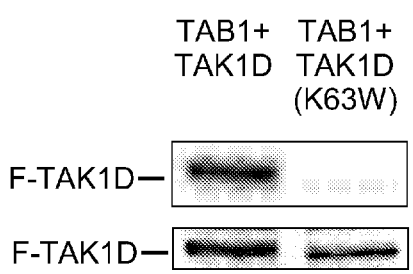
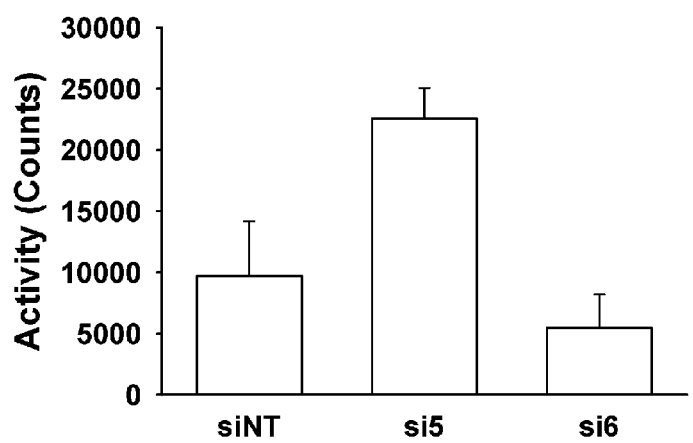
FIG. 2A-C

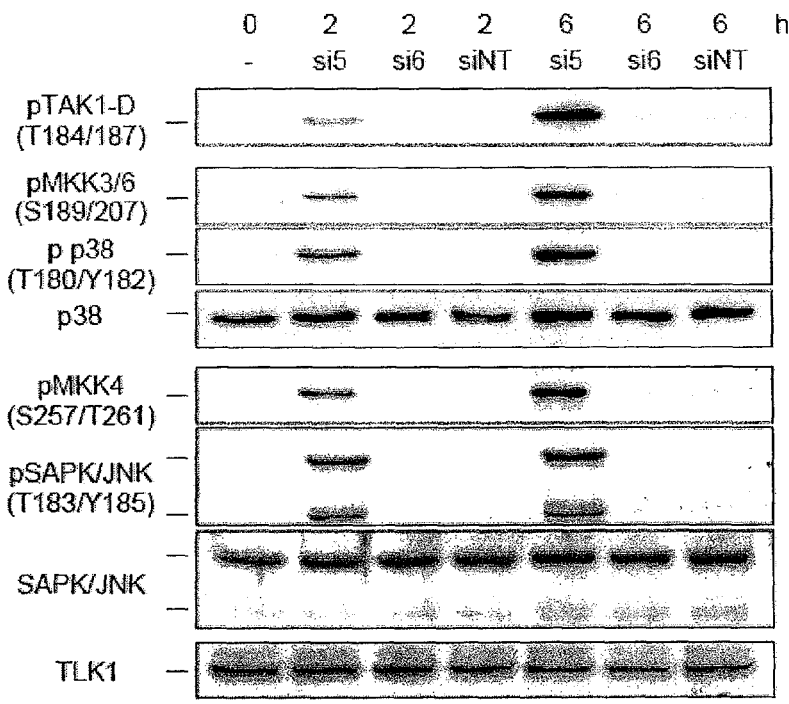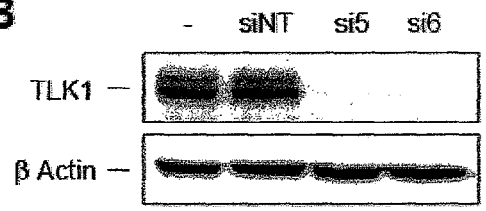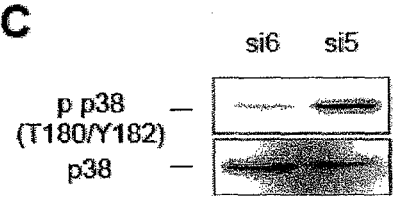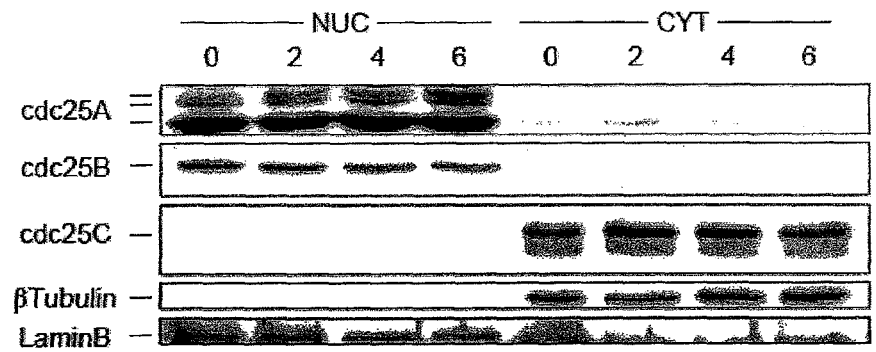
FIG. 3A-D

A
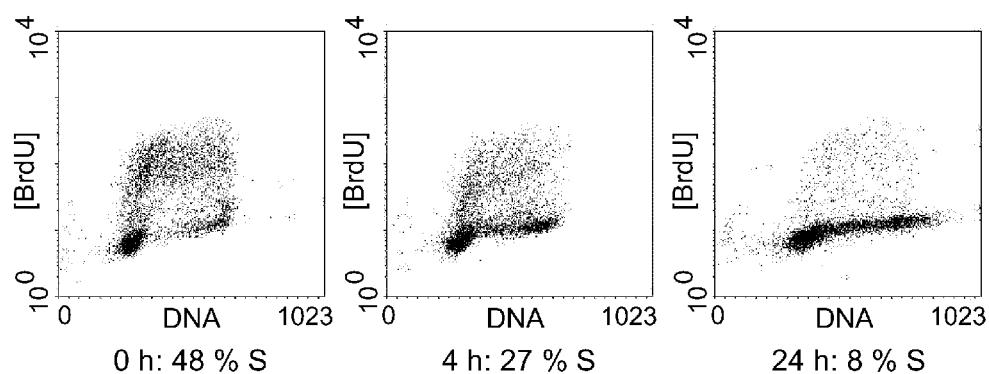
B
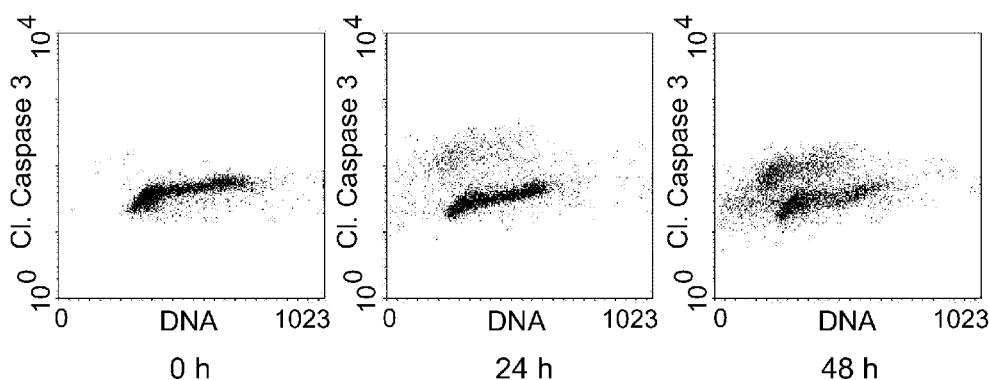
C
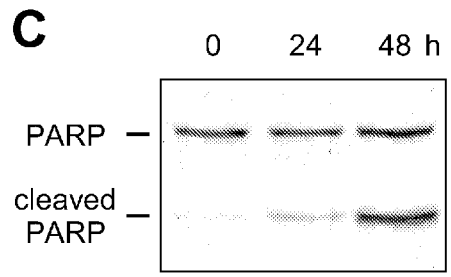
D
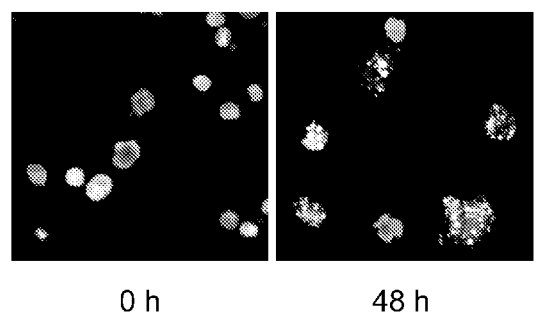
FIG. 10A-D

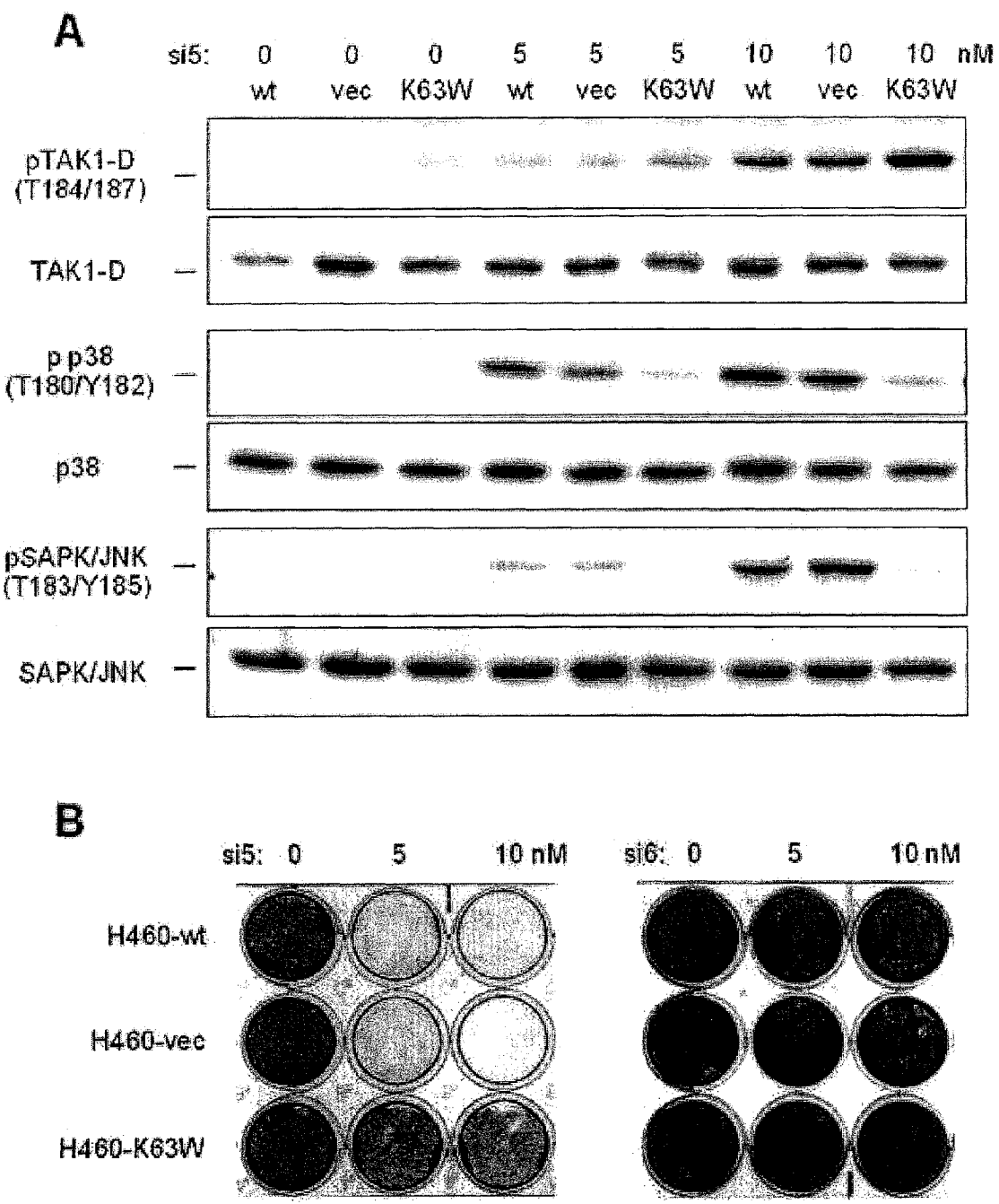
FIG. 16A-B

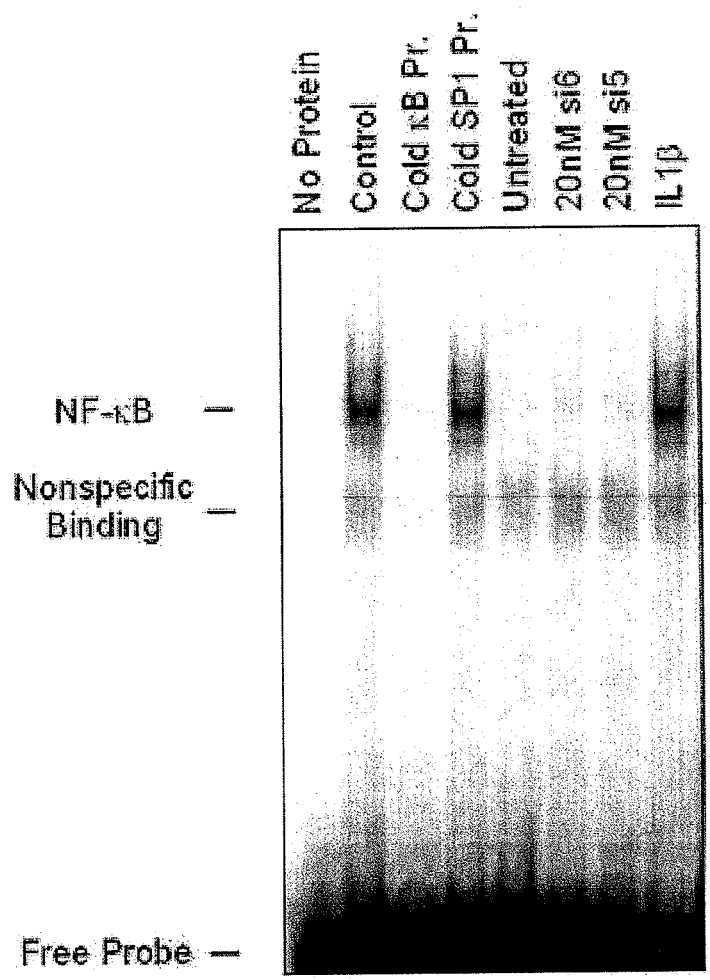
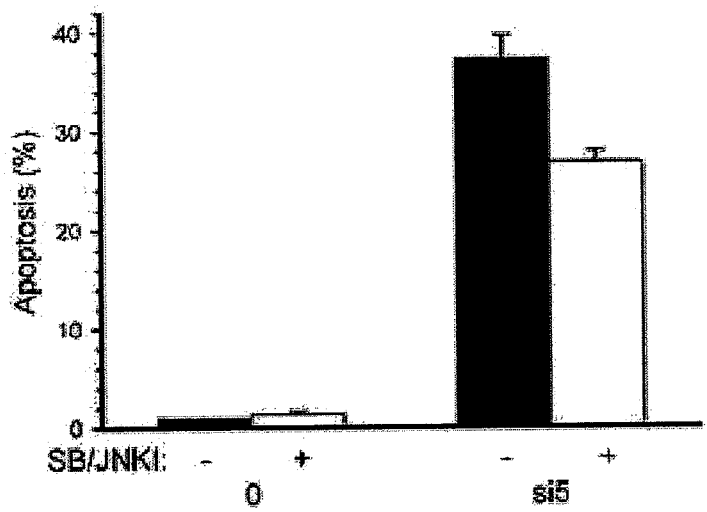
FIG. 16C–D

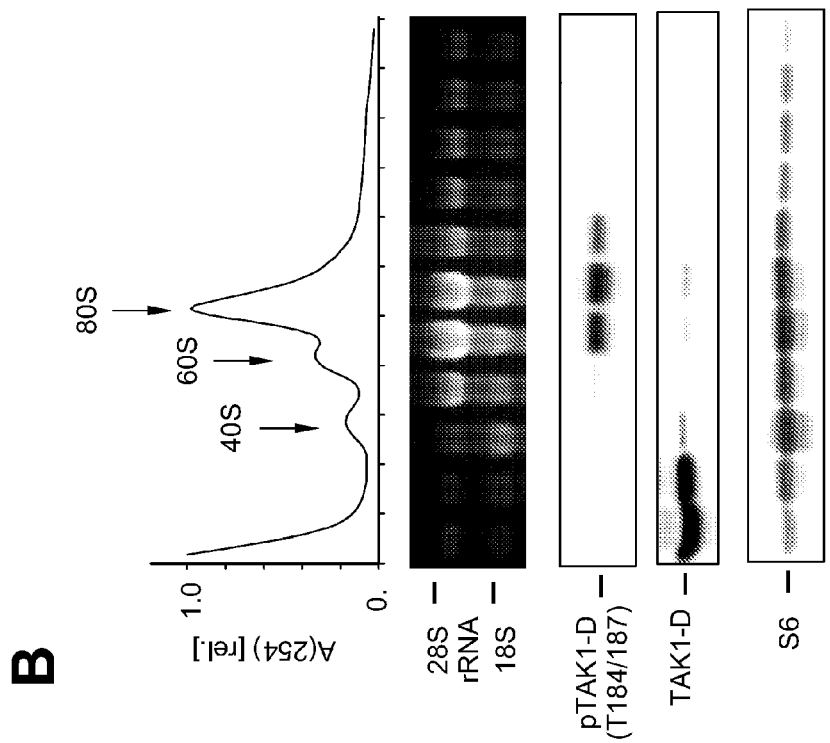
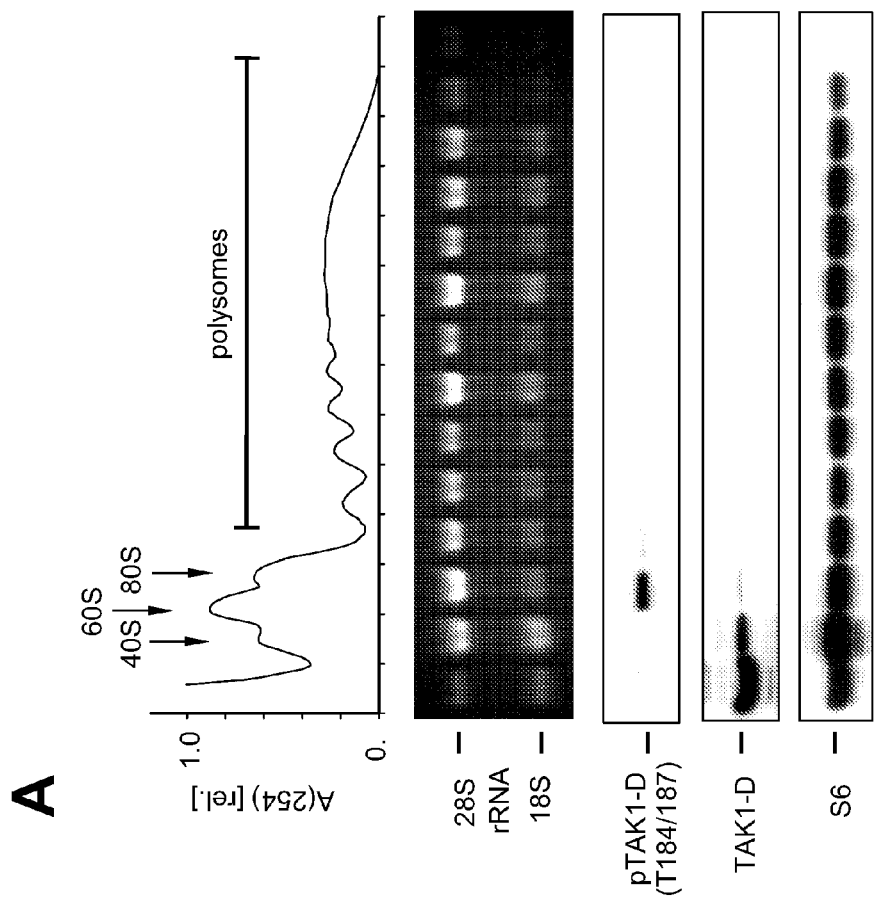
FIG. 18A-B

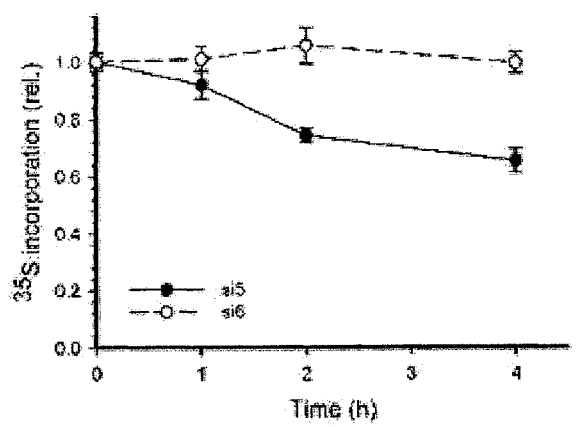
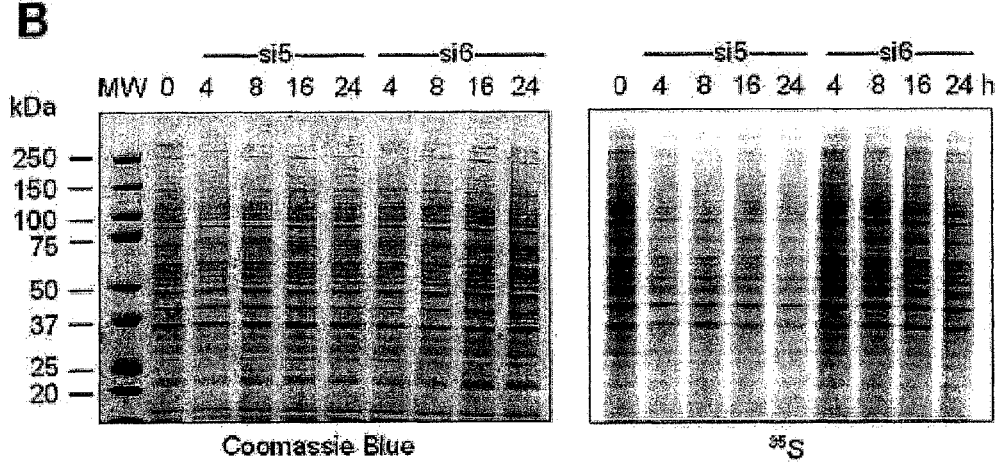
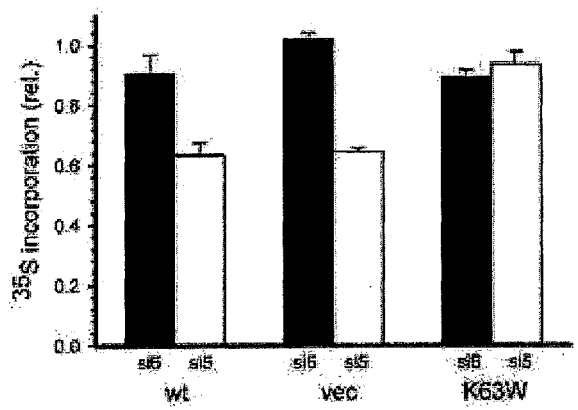
FIG. 21A-C

SEQUENCE LISTING

<160> NUMBER OF SEQ ID NOS: 28

<210> SEQ ID NO 1
<211> LENGTH: 19
<212> TYPE: RNA
<213> ORGANISM: Artificial Sequence
<220> FEATURE:
<223> OTHER INFORMATION: Artificial primer

<400> SEQUENCE: 1
ggcuuuugac cuuuaugaa                                                    19

<210> SEQ ID NO 2
<211> LENGTH: 21
<212> TYPE: DNA
<213> ORGANISM: Artificial Sequence
<220> FEATURE:
<223> OTHER INFORMATION: Artificial primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 2
ggcuuuugac cuuuaugaat t                                                 21

<210> SEQ ID NO 3
<211> LENGTH: 21
<212> TYPE: DNA
<213> ORGANISM: Artificial Sequence
<220> FEATURE:
<223> OTHER INFORMATION: Artificial primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 3
ttccgaaaac uggaaauacu u                                                 21

<210> SEQ ID NO 4
<211> LENGTH: 21
<212> TYPE: DNA
<213> ORGANISM: Artificial Sequence
<220> FEATURE:
<223> OTHER INFORMATION: Artificial primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 4
ggguggaaau ggcucaagut t                                                 21

<210> SEQ ID NO 5
<211> LENGTH: 21
<212> TYPE: DNA
<213> ORGANISM: Artificial Sequence
<220> FEATURE:
<223> OTHER INFORMATION: Artificial primer
<220> FEATURE:
<221> NAME/KEY: misc_feature
<222> LOCATION: (1)..(21)
<223> OTHER INFORMATION: This is a DNA/RNA combined sequence.

<400> SEQUENCE: 5
gtcccaccuu uaccgaguuc a                                                 21

```
<210> SEQ ID NO 6
<211> LENGTH: 19
<212> TYPE: RNA
<213> ORGANISM: Artificial Sequence
<220> FEATURE:
<223> OTHER INFORMATION: Artificial primer

<400> SEQUENCE: 6
ccaaaagaag augugauga                                                    19

<210> SEQ ID NO 7
<211> LENGTH: 21
<212> TYPE: RNA
<213> ORGANISM: Artificial Sequence
<220> FEATURE:
<223> OTHER INFORMATION: Synthetic primer

<400> SEQUENCE: 7
ggcuuuugac cuuuaugaau u                                                 21

<210> SEQ ID NO 8
<211> LENGTH: 21
<212> TYPE: RNA
<213> ORGANISM: Artificial Sequence
<220> FEATURE:
<223> OTHER INFORMATION: Synthetic primer

<400> SEQUENCE: 8
ccgaaaacug gaaauacuua a                                                 21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
atcgccgcaa ccacaggcaa c                                                 21

<210> SEQ ID NO 10
<211> LENGTH: 28
<212> TYPE: DNA
<213> ORGANISM: Artificial Sequence
<220> FEATURE:
<223> OTHER INFORMATION: Synthetic primer

<400> SEQUENCE: 10
gtccagttct gcaactagtt cttgcctg                                          28

<210> SEQ ID NO 11
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 11
ccaaaagaag augugaugat t                                                 21

<210> SEQ ID NO 12
<211> LENGTH: 21
<212> TYPE: DNA
```

```
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 12
ggcccguuuu ccacuaagat t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 13
ggcgaugggc cuauuuguut t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 14
ggguggaaau ggcucaagut t                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 15
cgaugggucu gugcacaaat t                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 16
gcucuuauga aguaccacat t                                              21

<210> SEQ ID NO 17
<211> LENGTH: 19
<212> TYPE: DNA
```

```
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(19)
<223> OTHER INFORMATION: This is a combined DNA/RNA sequence.

<400> SEQUENCE: 17
ggcuuuugac uuaugaatt                                                  19

<210> SEQ ID NO 18
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(23)
<223> OTHER INFORMATION: This is a combined DNA/RNA sequence.

<400> SEQUENCE: 18
ggcuuuugac cuguuuauga att                                             23

<210> SEQ ID NO 19
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 19
ggcuucugac cuuuaugaat t                                               21

<210> SEQ ID NO 20
<211> LENGTH: 42
<212> TYPE: RNA
<213> ORGANISM: Artificial Sequence
<220> FEATURE:
<223> OTHER INFORMATION: Synthetic primer

<400> SEQUENCE: 20
ggcuuuugac cuuuaugaau uaauucauaa aggucaaaag cc                        42

<210> SEQ ID NO 21
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 21
auauauauau auauauauat t                                               21

<210> SEQ ID NO 22
<211> LENGTH: 21
<212> TYPE: DNA
<213> ORGANISM: Artificial Sequence
<220> FEATURE:
<223> OTHER INFORMATION: Synthetic primer
<220> FEATURE:
```

```
<221> NAME/KEY: misc_feature
<222> LOCATION: (1)..(21)
<223> OTHER INFORMATION: This is a combined DNA/RNA sequence.

<400> SEQUENCE: 22
ttuauauaua uauauauaua u                                              21

<210> SEQ ID NO 23
<211> LENGTH: 21
<212> TYPE: RNA
<213> ORGANISM: Artificial Sequence
<220> FEATURE:
<223> OTHER INFORMATION: Synthetic primer

<400> SEQUENCE: 23
ggcuuuugac cuuuaugaau u                                              21

<210> SEQ ID NO 24
<211> LENGTH: 21
<212> TYPE: RNA
<213> ORGANISM: Artificial Sequence
<220> FEATURE:
<223> OTHER INFORMATION: Synthetic primer

<400> SEQUENCE: 24
uuccgaaaac uggaaauacu u                                              21

<210> SEQ ID NO 25
<211> LENGTH: 21
<212> TYPE: RNA
<213> ORGANISM: Artificial Sequence
<220> FEATURE:
<223> OTHER INFORMATION: Synthetic primer

<400> SEQUENCE: 25
ggcuuuugac cuuuaugaau u                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 26
ttccgaaaac uggaaauacu u                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(21)
<223> OTHER INFORMATION: This is a combined DNA/RNA sequence.

<400> SEQUENCE: 27
ggcuuuugac cuuuaugaat t                                              21

<210> SEQ ID NO 28
<211> LENGTH: 21
<212> TYPE: RNA
```

-continued

```
<213> ORGANISM: Artificial Sequence
<220> FEATURE:
<223> OTHER INFORMATION: Synthetic primer

<400> SEQUENCE: 28
uuccgaaaac uggaaauacu u                                              21
```

TAK1-D MEDIATED INDUCTION OF CELL DEATH IN HUMAN CANCER CELLS BY SPECIFIC SEQUENCE SHORT DOUBLE-STRANDED RNAS

This application claims benefit of priority to U.S. Provisional Application Ser. No. 61/024,076, filed Jan. 28, 2008, the entire contents of which are hereby incorporated by reference.

BACKGROUND OF THE INVENTION

A. Field of the Invention

The present invention relates to the fields of oncology, molecular biology and nucleic acid biochemistry. More particularly, it concerns methods of inducing apoptosis and/or cell cycle arrest in a cancer cell or modulating inflammation in a cell by contacting the cell with agonists of TAK1-D, including short nucleic acids.

B. Description of Related Art

Since the discovery of double-stranded RNA (dsRNA) mediated post-transcriptional gene silencing in *C. elegans* (Fire et al., 1998) and the description of 21 nucleotide dsRNAs effective in mammalian cells (Elbashir et al., 2001), small interfering RNAs (siRNAs) have been heavily used as a tool in biomedical research. In addition, the potential in vivo application of siRNAs as gene specific agents are now widely studied (Wall and Shi, 2003). Both applications depend decisively on the specificity of the siRNA for its target mRNA. Apart from acting as micro-RNAs and down-regulating gene expression through low stringency binding to the 3' untranslated region of mRNAs (Scacheri et al., 2004), siRNAs elicit cellular effects through binding and activating specific proteins. Currently, three such target proteins have been identified: (1) the Toll-like receptor 3 (TLR3), a receptor involved in the immune response, which activates NFκB and triggers the production of type I interferons (Alexopoulou et al., 2001); (2) dsRNA dependent protein kinase (PKR), a protein kinase activated preferentially by longer dsRNA molecules, which triggers the upregulation of interferon-inducible transcripts (Sledz et al., 2003) and inhibits protein synthesis through phosphorylation eIF-2α (de Haro et al., 1996); (3) 2',5'-oligoadenylate synthetase, which when activated catalyzes the formation of 2',5'-oligoadenylates that activate RNAase L, leading to cleavage of cellular RNAs (Player and Torrence, 1998). There remains, however, a need to identify new cancer targets for RNA therapy.

SUMMARY OF THE INVENTION

In one aspect, the invention provides a method of inducing apoptosis and/or cell cycle arrest in a cancer cell comprising contacting said cell with an agonist of Tak1-D function or expression. The angonist may be any agent that improves the activity of Tak1-D. In some embodiments, the agonist induces autophosphorylation of Tak1-D. In other embodiments, the agonist is a double-stranded RNA directed to an mRNA for TLK1. In a particular embodiment, the dsRNA has the sequence NC(A/U)(A/U)(A/U)(A/U)GAX$_{4-6}$AUGAN, wherein in N is any base or null and X is any base, GGCUUUUGACCUUUAUGAA (SEQ ID NO:1), CCAAAAGAAGAUGUGAUGA (SEQ ID NO:6), or

```
5'-GGCUUUUGACCUUUAUGAAU-U    (SEQ ID NO: 7)
                        |
3'-CCGAAAACUGGAAAUACUUA-A.   (SEQ ID NO: 8)
```

In some embodiments, the dsRNA may be encapsulated in a lipid vehicle. In another embodiment, the agonist is an expression construct that expresses activated Tak1-D. This activated form of TAK1-D could either be produced by the co-expression of TAK1-D and TAB1 protein (Sakurai et al., 2000) or by constructing a fusion protein consisting of the TAK1-D at the N terminus and TAB1 at the C terminus (Sakurai et al., 2002).

The cancer cell may be a lung cancer cell, a breast cancer cell, an esophageal cancer cell, a head & neck cancer cell, a brain cancer cell, a throat cancer cell, a stomach cancer cell, a colon cancer cell, a rectal cancer cell, a skin cancer cell, a liver cancer cell, a pancreatic cancer cell, an ovarian cancer cell, a testicular cancer cell, a prostate cancer cell, a uterine cancer cell, a cervical cancer cell, or a bladder cancer cell. In some embodiments, cancer cell is a metastatic cancer cell, a recurrent cancer cell, a multi-drug resistant cancer cell. The cancer cell may be a carcinoma, such as a keratinizing squamous cell carcinoma, a giant cell carcinoma, a bronchioalveolar adenocarcinoma, or a squamous cell carcinoma.

In some embodiments, the method further comprises contacting the cancer cell with a second apoptosis-inducing agent. The apoptosis-inducing agent may be any agent capable of inducing apoptosis in the cancer cell. In some embodiments, the second apoptosis-inducing agent may be a chemotherapeutic, radiation, or a polypeptide inducer of apoptosis.

In another aspect, the invention provides a method of modulating inflammation in a cell comprising contacting said cell with an agonist of Tak1-D function or expression. The cell may be an immune cell such as a B-cell or a T-cell. In some embodiments, the T-cell is reactive against an autoantigen. In some embodiments, the method further comprises contacting said cell with a second anti-inflammatory agent. The second anti-inflammatory agent may be any agent that reduces inflammation. In some embodiments, the second anti-inflammatory agent may be a non-steroidal anti-inflammatory agent (NSAID), a steroid, or an anti-metabolite.

In yet another aspect, the invention provides a method of treating a subject with cancer comprising administering to said subject an agonist of Tak1-D function or expression. Compounds of the present invention may be administered to a cell, tissue, organism, or patient in any manner known to those of skill in the art. For example, in certain embodiments, the agonist of Tak1-D function may be administered intratumorally, into tumor vasculature, loco-regional to a tumor, or systemically.

"Treatment" and "treating" refer to administration or application of an agent, drug, or remedy to a subject or performance of a procedure or modality on a subject for the purpose of obtaining a therapeutic benefit of a disease or health-related condition.

A subject is any animal with cancer that undergoes treatment. In many embodiments of the invention, a patient is a mammal, specifically a human. It is contemplated that compositions administered to a patient may be in a pharmaceutically acceptable formulation.

In yet a further aspect, the invention provides a method of inducing p38 MAPK and SAPK/JNK signaling in a cell comprising contacting said cell with an agonist of Tak1-D function or expression.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-C: Effect of dsRNAs on the activity of purified recombinant TAK1-D protein. (FIG. 2A) In vitro kinase assay showing the activation of TAK1-D autophosphorylation by siRNA si5. FLAG-tagged TAK1-D and His-tagged TAB1 were coexpressed in Hela cells and purified by immunoprecipitation with anti FLAG antibody. The autoradiograph in the top panel and the phosphorylation kinetics (▼: si5, ●: si6) show that autophosphorylation of the TAK1-D/TAB1 complex is increased by siRNA si5. The lower panel shows the Ponceau S stained proteins as a loading control. (FIG. 2B) Autoradiograph (top) and Ponceau S stained loading control (bottom) of a kinase reaction performed with wild-type and kinase inactive (K63W) TAK1-D indicating that the signal detected in the kinase assay is specific for TAK1-D. (FIG. 2C) Binding of radio-labeled siRNAs on FLAG tagged TAK1-D immobilized on magnetic beads. siRNA si5 shows increased binding. Error bars indicate the standard error of 3 experiments.

FIGS. 3A-D: Downstream signaling events triggered by the dsRNA mediated activation of TAK1-D. (FIG. 3A) Transfection of NCI-H460 cells with siRNA si5 leads to autophosphorylation and activation of TAK1-D within 2 h. Phosphorylation of MKK3/6 leads to activation of p38 MAPK, while phosphorylation of MKK4 activates SAPK/JNK. No activation of the two MAPK cascades can be observed after exposure of cells to siRNA si6 or siNT. The bottom panel demonstrates that the intracellular concentrations of TLK1, the mRNA of which is targeted by si5 and si6, remain constant and therefore do not contribute to the activation of p38 MAPK and SAPK/JNK. (FIG. 3B) TLK1 protein levels in HeLa cells are reduced to almost undetectable levels by si5 and si6 after 48 h. (FIG. 3C) Mouse peritoneal macrophages were treated with siRNA si5 and si6 for 4 h. The Western blot demonstrates that the activation of the TAK1-D p38 pathway by siRNAs of specific sequence is not limited to the human small cell lung cancer cell line NCI-H460. (FIG. 3D) Response of the cell cycle control phosphatases cdc25 to activation of the p38 MAPK and SAPK/JNK pathway. Nuclear cdc25A shows an increased phosphorylation as early as 2 h after exposure of NCI-H460 cells to siRNA si5, as visible by the increased intensity of the upper band in the top panel. For cdc25B the nuclear levels of the phosphatase decrease in response to activation of TAK1-D. Cdc25C does not seem to participate in these signaling events, as all cdc25C protein can be found in the cytoplasm. The lower two panels show immunoblots of control protein for the subcellular fractionation.

FIGS. 10A-D: Reaction of NCI-H460 cells to activation of p38 MAPK and SAPK/JNK. (FIG. 10A) BrdU labeling was used to determine the amount of NCI-H460 cells in the S phase of the cell cycle. Cells were pulse labeled with 100 μM BrdU for 15 minutes (0 and 4 h) or 10 μM for 1 h (24 h). Dot blots show DNA content versus BrdU signal. The number of S phase cells decreases within a few hours after treatment of cells with siRNA si5. (FIG. 10B) Flow cytometry dot blots, showing the cellular DNA content versus the amount of cleaved Caspase 3. Within 24 h after exposure to siRNA si5 cells in G1 as well as in the S phase of the cell cycle show Caspase 3 activation. (FIG. 10C) Activation of Caspase 3 leads to PARP cleavage and to (FIG. 10D) nuclear chromatin condensation visible in Hoechst 33342 stained NCI-H460 cells, typical of apoptosis.

FIGS. 16A-D: The kinase function of TAK1-D is required for si5 mediated activation of the stress-activated protein kinase cascade. (FIG. 16A) Untransfected (wt), vector transfected (vec), and TAK1-D/K63W transfected H460 cells were treated with the indicated concentration of dsRNA si5 for 4 h. Western blots using phospho specific antibodies, which are marked by p in front of the antigen name show, that although TAK1-D shows an increasing activating autophosphorylation with increasing concentration of si5 dsRNA in all three cell lines, the activation of p38 MAP kinase as well as of SAPK/JNK is significantly reduced in H460 cells transfected with the kinase inactive TAK1-D (K63W). (FIG. 16B) The three H460 cell lines were plated in a 12 well plate and treated with si5 or control dsRNA si6 as described above. After 48 hours cells were fixed and stained with crystal violet. 5 and 10 nM dsRNA si5 induce massive cell death in wild-type (H460-wt) as well as in vector transfected (H460-vec) cells but not in TAK1-D/K63W transfected H460 cells, demonstrating the dominant-negative effect of TAK1-D/K63W inhibits dsRNA si5 mediated cell death. (FIG. 16C) EMSA showing that dsRNA si5 does not activate NF-κB 3 hours after transfection, indicating that dsRNA si5 does not activate NF-κB dependent. dsRNA sensitive signaling pathways. In the right lane H460 cells, which have been treated for 30 min with 10 ng/ml IL1β, are shown as positive control. The left four lanes (no protein added, positive control, positive control with cold competitor oligonucleotide, and positive control with cold unspecific competitor) demonstrate the specificity of the assay. (FIG. 16D) Inhibition of p38 MAP kinase by SB-203580 (2 μM) and inhibition of SAPK/JNK by JNK inhibitor II (2 μM) significantly (t test: p<0.025) reduces the amount of apoptosis induced in H460 cells 24 h after transfection with 20 nM dsRNA si5. Error bars indicate the standard error of 3 experiments.

FIG. 18A-B: TAK1-D phosphorylated on T184/T187 is associated with the 80S ribosome. (FIG. 18A) Ribosomes of untreated H460 cells were separated by centrifugation through a 10-40% sucrose gradient. The upper panel shows the absorption profile at 254 nm through the gradient. The distribution of ribosomal RNAs in the monosomal and polysomal fractions is shown in the ethidium bromide stained formaldehyde-agarose gel below. Western blot analysis of the fractions demonstrates that phosphorylated TAK1-D can be detected in the fractions containing monosomes but not in the ones containing polysomes. The bottom panels show the distribution of ribosomal protein S6 as a loading control. (FIG. 18B) H460 cells were treated with 20 nM dsRNA si5 for 4 h and with 500 μM puromycin prior to lysis to disrupt the polysomes. Ribosomes were separated by centrifugation through a 10-40% sucrose gradient. The upper panel shows the absorption peaks of the small ribosomal subunit (40S), the large subunit (60S), and of assembled ribosomes (80S). The rRNA distribution in the various fractions is shown in an ethidium bromide stained formaldehyeagarose gel below. Western blotting shows that phosphorylated TAK1-D (T184/T187) can be found in the fractions containing 80S monosomes. The bottom panels show the distribution of ribosomal protein S6 as a loading control.

FIGS. 21A-C: Inhibition of translation be dsRNA si5. (FIG. 21A) Protein synthesis measured by [$^{35}$S] methionine incorporation drops after transfection of H460 cells with dsRNA si5. Measured [$^{35}$S] activities were normalized to pre-treatment values and the error bars indicate the standard error of triplicate samples. (FIG. 21B) Total proteins from H460 cells pulse labeled with [$^{35}$S] methionine at various time points after incubation with dsRNA si5 and si6 were separated by SDS-PAGE. The left panel demonstrates equal loading of the Coomassie blue stained gel. The autoradiography in the right panel shows a reduction of [$^{35}$S] incorporation after treatment with dsRNA si5. The unaltered pattern of radiolabeled proteins indicate a general inhibition of proteins synthesis. (FIG. 21C) Protein synthesis measured by [$^{35}$S] methionine incorporation drops significantly (t test: p<0.025) 4 h after treatment of wild-type H460 cells (wt) or of vector transfected cells (vec) with 10 nM si5. In contrast no change in protein synthesis can be detected in si5 treated H460 cells, which have been transfected with the dominant negative TAK1-D mutant TAK1-D/K63W. [$^{35}$S] activities were normalized to pre-treatment values and the error bars indicate the standard error of triplicate samples.

DESCRIPTION OF ILLUSTRATIVE EMBODIMENTS

A. The Present Invention

Short double-stranded RNAs (dsRNA) are potent biological entities triggering a number of cellular effects. Most prominent among these is the post-transcriptional gene silencing of target genes by small interfering RNAs (siRNAs). In addition dsRNAs activate signal transduction processes through molecules like PKR or the Toll-like receptor important in viral defense and in explaining off target effects of siRNAs. Only few of these dsRNA triggered pathways have been characterized yet.

Here, the inventors show that the splicing variant D of the TAK1 gene is activated by short double-stranded RNAs in a sequence specific manner. Activation of TAK1-D leads to the downstream activation of the p38 MAPK and of SAPK/JNK but not the NFκB pathway. In the human lung cancer cell line NCI-H460, the activation of these pathways leads to cell cycle arrest and apoptosis. The inventors have demonstrated that TAK1-D is activated by siRNAs of specific sequences, offering a new explanation for off target effects triggered by these molecules. In addition, the dsRNA triggered activation of a cell death pathway in the human lung cancer cell line studied illustrates the use of TAK1-D as a new and promising therapeutic target for the treatment of cancer and inflammatory diseases.

B. Tak1-D

Figure 1:
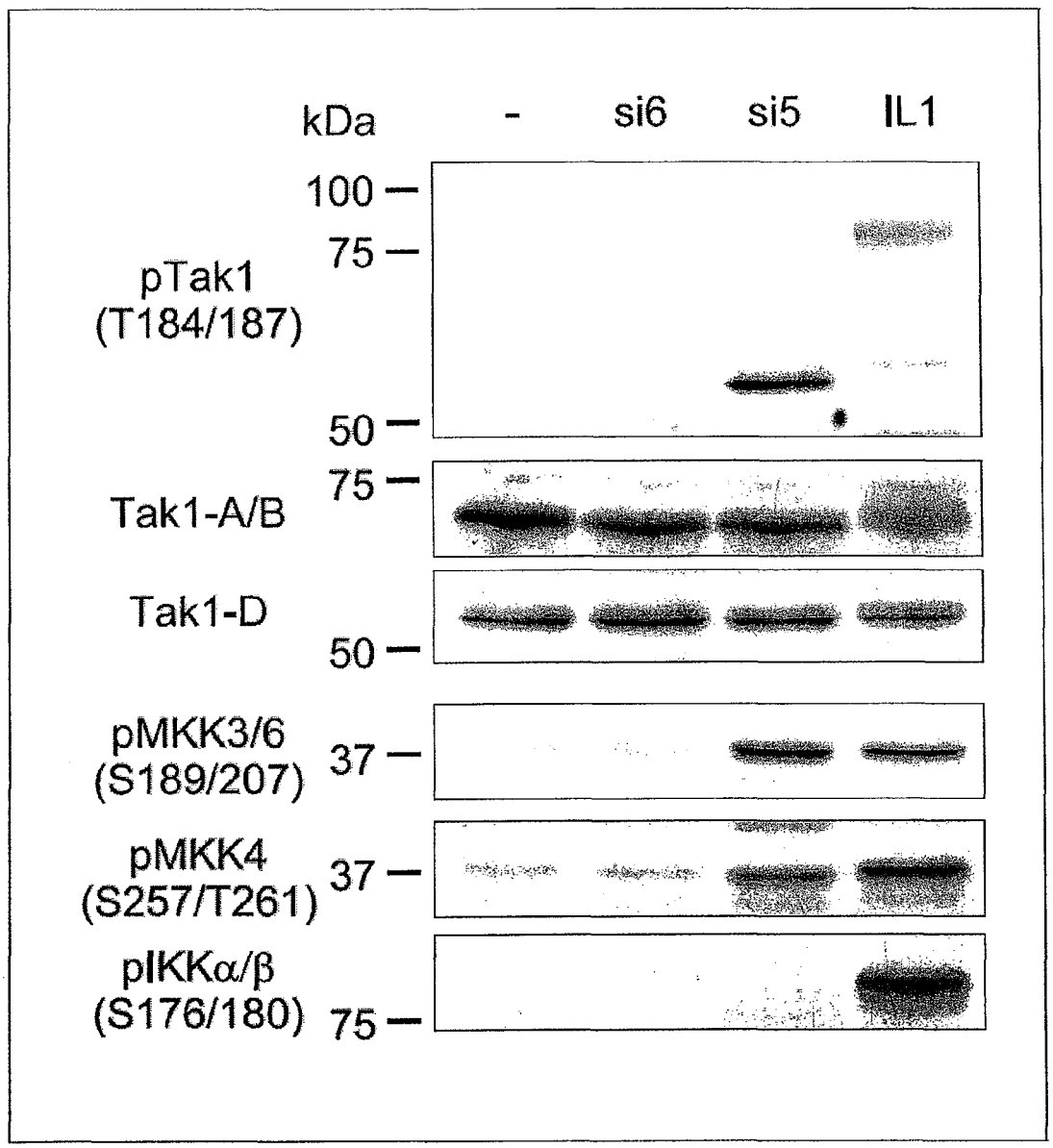
FIG. 1: Sequence specific activation of TAK1-D by short double-stranded RNAs. In intact NCI-H460 cells, treatment with siRNA si5 but not with si6 leads to autophosphorylation of TAK1 splice variant D on T184 and T187 within 3 h. TAK1-D is activated by these autophosphorylations and phosphorylates its downstream substrates MKK3/6 and MKK4. In contrast exposure of the cells to 10 ng/ml IL1β for 30 min activates exclusively the long form of TAK1 (TAK1-A), which in addition to MKK3/6 and MKK4 also activates the NFκB pathway through phosphorylation of IKKα/β.

As shown in FIG. 1, the TAK1 splicing variant activated by dsRNA si5 is TAK1-D. In contrast, treatment of NCI-H460 cells with 10 ng/ml IL-1 leads to autophosphorylation and activation of the long splicing variant A of TAK1 in response to IL-1 receptor activation (Ninomiya-Tsuji et al., 1999). It is also evident from the upper panel of FIG. 1 that IL-1 does not activate TAK1-D likely due to the lack of the TAB2/3 interaction domain in TAK1-D. The long (TAK1-A) and short (TAK1-D) variant of TAK1 also differ in their ability to phosphorylate and activate downstream targets. FIG. 1 shows that both TAK1-A and TAK1-D phosphorylate and activate mitogen activated protein kinase kinase (MAPKK) MKK3/6 and MKK4. In contrast only the long form (TAK1-A) is able to activate the NFκB pathway through phosphorylation of IKKα/β.

While there is a considerable body of knowledge about the cell biologic functions of the long splicing variants of TAK1, mainly about TAK1-A, the role of the short splicing variants has not yet been characterized. The inventors have demonstrated a specific activation of the D variant of TAK1 by short dsRNAs of defined sequence. Further, it has been demonstrated that activation of TAK1-D leads to the downstream activation of the p38 MAPK and of SAPK/JNK, but not the NFκB pathway.

P38 MAPK as well as SPK/JNK have a large number of downstream targets. Amongst these, the phosphorylation of the cell cycle control phos-phatase cdc25 (Bulavin et al., 2001; Goss et al., 2003) are of particular interest, as these phosphorylations have the potential to transduce an immediate and direct effect of TAK1-D activation to the cell cycle. It was determined that activation of TAK1-D in NCI-H460 cells leads to an inactivation of cdc25A and cdc25B through p38 MAPK and SAPK/JNK mediated phosphorylation and proteolytic destruction.

A pronounced effect on the cell cycle can be expected from the inactivation of cdc25A and cdc25B. BrdU pulse labeling and flow cytometric analysis were used to quantify the effect of TAK1-D induced inactivation of cdc25A and cdc25B on the cell cycle. FIG. 10A shows that within a few hours after transfection of NCI-H460 cells with siRNA si5 the number of cells in the S phase of the cell cycle drops to about half of the number found prior to the addition of the si5 siRNA. After 24 h DNA synthesis was found to have ceased in almost every cell. Because the fraction of cells containing a nuclear DNA amount specific for G1, S, or G2 cells did not change during the first 24 h after addition of siRNA si5, it can be concluded that activation of TAK1-D leads to an arrest of NCI-H460 cells in the G1, S, and G2 phase of the cell cycle. Cell cycle arrest triggers programmed cell death in many tumor cell lines.

C. RNA Interference

RNAi

In certain embodiments, the agonist of TAK1-D is a double-stranded RNA (dsRNA) directed to an mRNA for TLK1. In such embodiments, the dsRNA mediates the reduction of the expression of TLK1, which leads to the activation of TAK1-D.

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery et al., 1999; Montgomery et al., 1998; Sharp and Zamore, 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). It is generally accepted that RNAi acts post-transcriptionally, targeting RNA transcripts for degradation. It appears that both nuclear and cytoplasmic RNA can be targeted (Bosher and Labouesse, 2000).

1. siRNA siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998). siRNA are well known in the art. For example, siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

2. shRNA

Short hairpin RNA (shRNA) is a sequence of RNA that makes a tight hairpin turn that can be used to silence gene expression. shRNA is transcribed by RNA polymerase III. shRNA production in a mammalian cell can sometimes cause the cell to mount an interferon response as the cell seeks to defend itself from what it perceives as viral attack. Paddison et al. (2002) examined the importance of stem and loop length, sequence specificity, and presence of overhangs in determining shRNA activity. The authors found some interesting results. For example, they showed that the length of the stem and loop of functional shRNAs could vary. Stem lengths could range anywhere from 25 to 29 nt and loop size could range between 4 to 23 nt without affecting silencing activity. Presence of G-U mismatches between the 2 strands of the shRNA stem did not lead to a decrease in potency. Complementarity between the portion of the stem that binds to the target mRNA (antisense strand) and the mRNA, on the other hand, was shown to be critical. Single base mismatches between the antisense strand of the stem and the mRNA abolished silencing. It has been reported that presence of 2 nt 3'-overhangs is critical for siRNA activity (Elbashir et al., 2001). Presence of overhangs on shRNAs, however, did not seem to be important. Some of the functional shRNAs that were either chemically synthesized or in vitro transcribed, for example, did not have predicted 3' overhangs.

3. Production of Inhibitory Nucleic Acids dsRNA can be synthesized using well-described methods (Fire et al., 1998). Briefly, sense and antisense RNA are synthesized from DNA templates using T7 polymerase (MEGAscript, Ambion). After the synthesis is complete, the DNA template is digested with DNaseI and RNA purified by phenol/chloroform extraction and isopropanol precipitation. RNA size, purity and integrity are assayed on denaturing agarose gels. Sense and antisense RNA are diluted in potassium citrate buffer and annealed at 80° C. for 3 min to form dsRNA. As with the construction of DNA template libraries, a procedures may be used to aid this time intensive procedure. The sum of the individual dsRNA species is designated as a "dsRNA library."

The making of siRNAs has been mainly through direct chemical synthesis; through processing of longer, double-stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vitro transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

Several groups have developed expression vectors that continually express siRNAs in stably transfected mammalian cells (Brummelkamp et al., 2002; Lee et al., 2002; Miyagishi and Taira, 2002; Paddison et al., 2002; Paul et al., 2002; Sui et al., 2002; Yu et al., 2002). Some of these plasmids are engineered to express shRNAs lacking poly (A) tails (Brummelkamp et al., 2002; Paddison et al., 2002; Paul et al., 2002; Yu et al., 2002). Transcription of shRNAs is initiated at a polymerase III (pol III) promoter and is believed to be terminated at position 2 of a 4-5-thymine transcription termination site. shRNAs are thought to fold into a stem-loop structure with 3' UU-overhangs. Subsequently, the ends of these shRNAs are processed, converting the shRNAs into ~21 nt siRNA-like molecules (Brummelkamp et al., 2002). The siRNA-like molecules can, in turn, bring about gene-specific silencing in the transfected mammalian cells.

D. Nucleic Acids

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between 3 and about 100 nucleobases in length. The term "polynucleotide" refers to at least one molecule of greater than about 100 nucleobases in length.

These definitions refer to a single-stranded or double-stranded nucleic acid molecule. Double-stranded nucleic acids are formed by fully complementary binding, although in some embodiments a double-stranded nucleic acid may formed by partial or substantial complementary binding. Thus, a nucleic acid may encompass a double-stranded molecule that comprises one or more complementary strand(s) or "complement(s)" of a particular sequence, typically comprising a molecule. As used herein, a single-stranded nucleic acid may be denoted by the prefix "ss" and a double-stranded nucleic acid by the prefix "ds".

1. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. A nucleobase may be comprised in a nucleoside or nucleotide, using any chemical or natural synthesis method described herein or known to one of ordinary skill in the art.

2. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

3. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

4. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides, or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moeity which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moeity replacing phosphodiester backbone moeity used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate Rnase H; and U.S. Pat. No. 5,708,154 which describes RNA linked to a DNA to form a DNA-RNA hybrid.

5. Preparation of Nucleic Acids

A nucleic acid may be made by any technique known to one of ordinary skill in the art, such as chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

6. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

7. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

E. Vectors

In one embodiment, the agonist of Tak1-D is an expression construct that expresses activated Tak1-D. Activated Tak1-D may be encoded by a nucleic acid molecule comprised in a vector. In this manner, an activated Tak1-D can be provided to a patient through the administration of such a vector, so long as the activated Tak1-D is expressed in the patient. TAK1-D is activated when co-expressed with a fused to TAB1. Possible strategies are therefore: (1) expression of TAK1-D and TAB1 protein through different promoters, (2) expression of a polycistronic mRNA containing the coding sequence of TAK1-D and TAB1 from a single promoter, (3) expression of the fusion protein TAK1-D/TAB1 from a single promoter.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (2001) and Ausubel et al. (1996) both incorporated herein by reference. In addition to encoding a modified polypeptide such as modified gelonin, a vector may encode non-modified polypeptide sequences such as a tag or targetting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage. A targetting molecule is one that directs the modified polypeptide to a particular organ, tissue, cell, or other location in a subject's body.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Viral Vectors a. Adenoviral Vectors

One method for delivery of the recombinant DNA involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a recombinant gene construct that has been cloned therein.

The adenovirus vector may be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the some starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., 109-1011 plaque-forming units per ml, and they are highly infective. The life cycle of adenovirus does not require integration into the host cell genome. The foreign genes delivered by adenovirus vectors are episomal and, therefore, have low genotoxicity to host cells.

b. Retroviral Vectors

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants.

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

c. Adeno-Associated Viral Vectors

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin et al., 1984; Laughlin et al., 1986; Lebkowski et al., 1988; McLaughlin et al., 1988), which means it is applicable for use with the present invention. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Ohi et al., 1990; Walsh et al., 1994; Wei et al., 1994). Recently, an AAV vector has been approved for phase I human trials for the treatment of cystic fibrosis.

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

d. Herpesvirus Vectors

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene therapy contexts (U.S. Pat. No. 5,672,344).

e. Vaccinia Virus Vectors

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

f. Oncolytic Viral Vectors

Oncolytic viruses are also contemplated as vectors in the present invention. Oncolytic viruses are defined herein to generally refer to viruses that kill tumor or cancer cells more often than they kill normal cells. Exemplary oncolytic viruses include adenoviruses which overexpress ADP. These viruses are discussed in detail in U.S. Patent Application Pub. No. 20040213764, U.S. Patent Application Pub. No. 20020028785, and U.S. patent application Ser. No. 09/351,778, each of which is specifically incorporated by reference in its entirety into this section of the application and all other sections of the application. Exemplary oncolytic viruses are discussed elsewhere in this specification. One of ordinary skill in the art would be familiar with other oncolytic viruses that can be applied in the pharmaceutical compositions and methods of the present invention.

g. Other Viral Vectors

Other viral vectors that may be employed as vectors in the present invention include those viral vectors that can be applied in vaccines, or in dual vaccine and immunotherapy applications. Viral vectors, and techniques for vaccination and immunotherapy using viral vectors, are described in greater detail in PCT application WO0333029, WO0208436, WO0231168, and WO0285287, each of which is specifically incorporated by reference in its entirely for this section of the application and all other sections of this application. Additional vectors that can be applied in the techniques for vaccination and dual immunotherapy/vaccination include those oncolytic viruses set forth above.

Other viral vectors also include baculovirus vectors, parvovirus vectors, picornavirus vectors, alphavirus vectors, semiliki forest virus vectors, Sindbis virus vectors, lentivirus vectors, and retroviral vectors. Vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Other viral vectors for application in the compositions and methods of the present invention include those vectors set forth in Tang et al. (2004), which is herein specifically incorporated by reference in its entirety for this section of the application and all other sections of the application.

h. Gene Delivery Using Modified Viruses

A therapeutic nucleic acid may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Various strategies have been used to modify adenovirus tropism. Such modifications may allow adenoviral vectors to be targeted to specific cell types not normally infected by unmodified adenovirus vectors. U.S. Pat. No. 5,559,099 (herein incorporated by reference) describes a recombinant virus comprising a chimeric penton base protein with a nonpenton amino acid sequence specific for a receptor, antibody, or epitope in addition to or in place of a wild-type penton base sequence, and a therapeutic gene. U.S. Pat. No. 5,543,328 (herein incorporated by reference) claims an adenovirus wherein the adenovirus fiber includes a ligand specific for a receptor located on a desired cell type. Such an adenovirus fiber can be prepared by removing all or a portion of the fiber protein head portion and replacing it with ligand, or by creating a fusion between a full length fiber protein and a ligand. U.S. Publication No. 20060002893 (herein incorporated by reference) describes modification of adenoviral vector hexon proteins to target cells which express a urokinase-type plasminogen activator receptor (UPAR). Such modifications can make the these UPAR targeted vectors useful for gene delivery to tumor vasculature, endothelial cells, muscle cells and brain cells. U.S. Pat. No. 7,235,233 (herein incorporated by reference) discloses adenoviral vectors modified for tropism to skeletal muscle and myoblasts. U.S. Pat. No. 6,740,511 (herein incorporated by reference) discloses modification of adenovirus vector tropism for cells expressing gastrin releasing peptide, tumor cells expressing mucins and cells expressing $\alpha 4\beta 1$-integrins.

i. Protamine

Protamine may also be used to form a complex with an expression construct. Such complexes may then be formulated with the lipid compositions described above for administration to a cell. Protamines are small highly basic nucleoproteins associated with DNA. Their use in the delivery of nucleic acids is described in U.S. Pat. No. 5,187,260, which is incorporated by reference. U.S. patent application Ser. No. 10/391,068, which pertains to methods and compositions for increasing transduction efficiency of a viral vector by complexing the viral vector with a protamine molecule, is specifically incorporated by reference herein.

2. Non-Viral Delivery

In addition to viral delivery of the nucleic acid encoding a MDA-7 protein, the following are additional methods of recombinant gene delivery to a given host cell and are thus considered in the present invention.

In a further embodiment of the invention, an expression vector may be entrapped in a liposome or lipid formulation. Lipid particles, such as liposomes, are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Recent advances in lipid formulations have improved the efficiency of gene transfer in vivo (Smyth-Templeton et al., 1997; WO 98/07408). A novel lipid formulation composed of an equimolar ratio of 1,2-bis(oleoyloxy)-3-(trimethyl ammonio)propane (DOTAP) and cholesterol significantly enhances systemic in vivo gene transfer, approximately 150-fold. The DOTAP:cholesterol lipid formulation is said to form a unique structure termed a "sandwich liposome". This formulation is reported to "sandwich" DNA between an invaginated bi-layer or 'vase' structure. Beneficial characteristics of these lipid structures include a positive colloidal stabilization by cholesterol, two dimensional DNA packing and increased serum stability.

Manufacture and use of such a formulation for the treatment of cancer is provided in U.S. Ser. No. 09/575,473, which is hereby incorporated by reference.

In further embodiments, the lipid particle is further defined as a nanoparticle. A "nanoparticle" is defined herein to refer to a submicron particle. The submicron particle can be of any size. For example, the nanoparticle may have a diameter of from about 0.1, 1, 10, 100, 300, 500, 700, 1000 nanometers or greater. The nanoparticles that are administered to a subject may be of more than one size.

Any method known to those of ordinary skill in the art can be used to produce nanoparticles. In some embodiments, the nanoparticles are extruded during the production process. Exemplary information pertaining to the production of nanoparticles can be found in U.S. Publication No. 20050143336, U.S. Publication No. 20030223938, and U.S. Publication No. 20030147966, each of which is herein specifically incorporated by reference into this section.

In certain embodiments, an anti-inflammatory agent is administered with the lipid to prevent or reduce inflammation secondary to administration of a lipid:nucleic acid complex. For example, the anti-inflammatory agent may be a non-steroidal anti-inflammatory agent, a salicylate, an anti-rheumatic agent, a steroid, or an immunosuppressive agent. Information pertaining to administration of anti-inflammatory agents in conjunction with lipid-nucleic acid complexes can be found in U.S. Publication No. 20050143336, which is herein specifically incorporated by reference.

Synthesis of DOTAP:Cholesterol nanoparticles is by any method known to those of ordinary skill in the art. For example, the method can be in accordance with that set forth in Chada et al. (2003) or Templeton et al. (1997), both of which are herein specifically incorporated by reference. DOTAP:Cholesterol-DNA complexes were prepared fresh two to three hours prior to injection in mice.

One of ordinary skill in the art would be familiar with use of lipid particles such as liposomesto entrap nucleic acid sequences. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use subcutaneous, intradermal, intratumoral, or intracranial injection to avoid the toxicity and stability problems associated with cationic lipids in the circulation. The interaction of liposomes and plasma proteins is responsible for the disparity between the efficiency of in vitro (Felgner et al., 1987) and in vivo gene transfer (Zhu et al., 1993; Solodin et al., 1995; Liu et al., 1995; Thierry et al., 1995; Tsukamoto et al., 1995; Aksentijevich et al., 1996).

Recent advances in liposome formulations have improved the efficiency of gene transfer in vivo (WO 98/07408). A novel liposomal formulation composed of an equimolar ratio of 1,2-bis(oleoyloxy)-3-(trimethyl ammonio)propane (DOTAP) and cholesterol significantly enhances systemic in vivo gene transfer, approximately 150 fold. The DOTAP:cholesterol lipid formulation is said to form a unique structure termed a "sandwich liposome." This formulation is reported to "sandwich" DNA between an invaginated bi-layer or "vase" structure. Beneficial characteristics of these liposomes include colloidal stabilization by cholesterol, two dimensional DNA packing and increased serum stability.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

The liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

A nucleic acid for nonviral delivery may be purified on polyacrylamide gels, cesium chloride centrifugation gradients, column chromatography or by any other means known to one of ordinary skill in the art (see for example, Sambrook et al., 2001, incorporated herein by reference). In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, bulk of cellular components or in vitro reaction components, and/or the bulk of the total genomic and transcribed nucleic acids of one or more cells. Methods for isolating nucleic acids (e.g., equilibrium density centrifugation, electrophoretic separation, column chromatography) are well known to those of skill in the art.

E. Treatment of Disease

1. Cancer

In one aspect, the invention provides a method of inducing apoptosis and/or cell cycle arrest in a cancer cell comprising contacting said cell with an agonist of Tak1-D function. It is contemplated that a wide variety of tumors may be treated using these therapies, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

a. Formulations and Routes for Administration to Patients

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed (e.g., post-operative catheter). For practically any tumor, systemic delivery also is contemplated. This will prove especially important for attacking microscopic or metastatic cancer.

The active compounds may also be administered as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

b. Combination Treatments

In some embodiments, the method further comprises contacting the cancer cell with a second apoptosis-inducing agent. One goal of current cancer research is to find ways to improve the efficacy of chemo- and radiotherapy, such as by combining traditional therapies with other anti-cancer treatments. In the context of the present invention, it is contemplated that the agonist of TAK1-D function could be used in conjunction with chemotherapeutic, radiation, a polypeptide inducer of apoptosis or other therapeutic intervention. The methods of the current invention may precede or follow the second agent/treatment by intervals ranging from minutes to weeks. It also is conceivable that more than one administration of either the agonist of TAK1-D function or the other agent will be desired.

i. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

ii. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of your internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques. Stereotactic radiotherapy is used to treat brain tumors. This technique directs the radiotherapy from many different angles so that the dose going to the tumor is very high and the dose affecting surrounding healthy tissue is very low. Before treatment, several scans are analyzed by computers to ensure that the radiotherapy is precisely targeted, and the patient's head is held still in a specially made frame while receiving radiotherapy. Several doses are given.

Stereotactic radio-surgery (gamma knife) for brain tumors does not use a knife, but very precisely targeted beams of gamma radiotherapy from hundreds of different angles. Only one session of radiotherapy, taking about four to five hours, is needed. For this treatment you will have a specially made metal frame attached to your head. Then several scans and x-rays are carried out to find the precise area where the treatment is needed. During the radiotherapy, the patient lies with their head in a large helmet, which has hundreds of holes in it to allow the radiotherapy beams through.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

iii. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gene silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds can be used to target the anti-cancer agents discussed herein.

Examples of immunotherapies currently under investigation or in use are immune adjuvants e.g., *Mycobacterium bovis*, *Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

iv. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

v. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

vi. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon α, β, and γ; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

2. Inflammation

In another aspect, the invention provides a method of modulating inflammation in a cell comprising contacting said cell with an agonist of Tak1-D function. For example, the second anti-inflammatory agent may be a non-steroidal anti-inflammatory agent (NSAID), a steroid, or an anti-metabolite.

"Inflammation" or the "inflammatory process" refers to inflammation as characterized by four basic symptoms: redness, swelling, heat, and pain. Inflammation can be acute or chronic, with chronic inflammation characterized further by infiltration of T lymphocytes and mononuclear phagocytes, while acute inflammation is characterized by neutrophil infiltration and edema (see, e.g., Paul, 1993). In the inflammatory process, presentation to or recognition of foreign antigen by B and T cells leads to activation an amplification system, including the complement cascade, lipid mediator, coagulation cascade, antibody production, cytokine release, recruitment of phagocytes, etc. Cytokine signaling, e.g., by Il-1β, TNF-α, and IFN-γ, is an important component of the inflammatory process for recruitment of phagocytes and T lymphocytes. Cytokines are produced by immune cells such as T cells (IFN-γ) and macrophages (Il-1β, TNF-α). Immediate and delayed type hypersensitivity are acute and chronic inflammation, respectively, that occur in the skin.

The therapies of the present invention may be used in combination with secondary therapies directed to the treatment or prevention of inflammation in a subject. For example, agents that bind to one or more of the mediators of inflammation may be employed. One of skill in the art will recognize other secondary therapies that may be used in conjugation with the methods and compositions of the present invention.

This process may involve contacting the cancer cell with the therapies at the same time, such as by contacting the cell with a single composition or treatment that includes both agents, or by contacting the cell with two distinct compositions or treatments at the same time. Alternatively, the treatment of the current invention may precede or follow the other treatment by intervals ranging from minutes to weeks. In embodiments where the agents are applied separately to the cell, one would generally ensure that a significant period of time did not expire between the time of each delivery, such that the treatments would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

F. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Small Double-Stranded RNAs of Specific Sequence Induce Tak1-D Autophosphorylation and Activation of the Stress-Activated Protein Kinase Cascade While studying the effect of siRNAs on the expression of the protein kinase TLK1 the inventors observed an unexpected activation of the cellular stress response pathways. After screening several mitogen activated protein kinase kinase kinase (MAPKKK) proteins the inventors found an siRNA mediated activation of transforming growth factor beta activated kinase 1 (TAK1). Of two 21-mer siRNAs studied, only one induced a stress response in the human NSCLC line NCI-H460. The sequences of the two siRNA were the following:

```
si5:    GGCUUUUGACCUUUAUGAAtt    (SEQ ID NO: 2)
        ttCCGAAAACUGGAAAUACUU    (SEQ ID NO: 3)
si6:    GGGUGGAAAUGGCUCAAGUtt    (SEQ ID NO: 4)
        gtCCCACCUUUACCGAGUUCA    (SEQ ID NO: 5)
```

Both siRNAs were directed against the mRNA of the same gene TLK1. As shown in FIG. 1 treatment of H460 cells with 20 nM of siRNA si5 leads to the activation of the p38 MAP kinase pathway through activating phosphorylation of its upstream kinases MKK3 and MKK6 as well as to the activation of the stress-activated protein kinase jun-amino-terminal kinase (SAPK/JNK) pathway by activating phosphorylation of its upstream kinase MKK4. An equal concentration of siRNA si6 had no effect. The activation of these kinases via si5 was found to be rapid as the signal shown in FIG. 1 was obtained after a 3 h incubation, indicating that the RISC mediated degradation of mRNAs played no role in the phenomenon observed.

In an effort to identify the MAPKKK responsible for the activation of the p38 MAP kinase and SAPK/JNK pathway, several of these kinases were screened for siRNA si5 mediated activation. Using a phosphorylation specific antibody directed against the activating phosphorylation of Tak1 on threonine 184 and 187, a si5 induced signal was detected by Western blot hybridization slightly above 50 kDa as shown in the upper panel of FIG. 1. This band was shown to be also immuno reactive with an antibody directed against the N-terminal sequence of Tak1 and therefore represents splicing variant D of Tak1. Autophosphorylation of T187 as well as of other residues in the activation loop of TAK1 have been shown to be essential for the activation of the kinase (Singhirunnusorn et al., 2005).

As shown in FIG. 1 treatment with siRNA si5 does not induce activating autophosphorylation of the other three splicing variants of Tak1 which could be detected in H460 cells on the mRNA level. In contrast, treatment of H460 cells with 10 ng/ml IL1 leads to the well established (Ninomiya-Tsuji et al., 1999) autophosphorylation of the large splicing variant of Tak1 (A and B), activating the p38 MAP kinase pathway (MKK3/6), the SAPK/JNK pathway (MKK4), as well as the NFκB cascade (IKKα/β) as shown in the right lane of FIG. 1. It is also evident from the upper panel of FIG. 1 that IL-1 does not activate TAK1-D likely due to the lack of the TAB2/3 interaction domain in TAK1-D. The long (TAK1-A) and short (TAK1-D) variant of TAK1 also differ in their ability to phosphorylate and activate downstream targets. FIG. 1 shows that both TAK1-A and TAK1-D phosphorylate and activate mitogen activated protein kinase kinase (MAPKK) MKK3/6 and MKK4. In contrast only the long form (TAK1-A) is able to activate the NFκB pathway through phosphorylation of IKKα/β. This indicates a differential downstream signaling of the different splicing variants of Tak1 and shows that slicing variant D fails to activate the important pro-survival pathway NFκB is involved in.

While the lack of the C-terminal protein interaction domain in TAK1-D makes it unlikely that siRNA si5 activates the kinase through interaction with upstream signaling components in intact NCI-H460 cells, it does not rule out that possibility. To verify if siRNA si5 indeed interacts with TAK1-D directly, the activation of the kinase was studied in vitro using purified proteins. The inventors found that adding siRNA si5 but not siRNA si6 lead to an increase in autophosphorylation activity of the TAK1-D TAB1 complex as shown in FIG. 2A. To rule out an effect of si5 or si6 on another kinase co-precipitated with TAK1-D an inactive FLAG tagged TAK1-D was constructed by mutating lysine at position 63 to tryptophan (K62W) (Sakurai et al., 2000). FIG. 2B demonstrates that TAK1-D(K63W) does not show any detectable autophosphorylation in the kinase assay, indicating that the kinase assay shown in FIG. 2A specifically measures TAK1-D kinase activity. To test whether the increased activation of the TAK1-D/TAB1 complex by siRNA si5 is caused by an increased affinity of the RNA molecule to the kinase, binding of radiolabeled siRNAs to immunoprecipitated FLAG tagged TAK1-D was measured. In FIG. 2C the amount of RNA bound to immobilized FLAG-TAK1-D is given. It can be seen that the number of si5 molecules bound to TAK1-D under buffer conditions used for the kinase assay is significantly greater than the number of si6 or siNT RNAs. These data demonstrate that there is a moderately increased affinity of siRNA si5 to TAK1-D at least partially explaining the observed modulation of TAK1-D activity by siRNA si5.

FIGS. 3A-D illustrate the timecourse as well the downstream signaling events of dsRNA mediated Tak1-D activation in more detail. The upper panel of FIG. 3A shows that the activating auto-phosphorylation of TAK1-D on T184 and T187 occurs within 2 h after the addition of siRNA si5 to the cell culture. Six hours after the addition of siRNA si5 a significantly stronger autophosphorylation signal of Tak1-D can be observed. This activation is not triggered by siRNA si6 or by the non-targeting scrambled sequence siNT, even at later timepoints. Si5 induced Tak1-D kinase activity leads to the phosphorylation and activation of MKK3/6 as well as MKK4. This Western blot demonstrates again, that the activation does not occur after exposure of NCI-H460 cells to siRNA of different nucleotide sequence, like si6 or siNT. The activation of TAK1-D leads to a phosphorylation of the MAPKKs of both stress activated protein kinase signaling pathways, indicated by the occurrence of activation phosphorylation on MKK3/6 and MKK4 (FIG. 3A). Consecutively activation of MKK3/6 leads to phosphorylation and activation of the p38 MAPK, while activation of MKK4 phosphorylates and activates SAPK/JNK. These mitogen activated protein kinase kinases phosphorylate and activate their respective substrates p38 MAP kinase and SAPK/JNK. The bottom panel of FIG. 3A shows that the protein levels of Tlk1, the gene product siRNA si5 and siRNA si6 are directed against, remain unchanged during the first 6 h after addition of the siRNAs. FIG. 3B shows that after 48 h both siRNAs si5 and si6 drastically reduce the expression level of their target gene TLK1 in HeLa cells. This provided further confirmation, apart from the rapid occurrence of TAK1-D phosphorylation, that gene silencing effects of the siRNAs play no role in the phenomena described.

Having demonstrated the sequence specific activation of TAK1-D in a human non-small cell lung cancer cell line it is interesting to ask if this activation also occurs in other cell types. It has been reported (Dempsey et al., 2000) that the splicing variant D of TAK1 could not be detected in many cell lines despite its expression in the parental tissue, most probably due to downregulation of the transcript during in vitro culture. Therefore, the inventors used macrophages 24 h after obtaining them from athymic NCR-NU/NU female mice by peritoneal lavage. FIG. 3c shows that p38 is activated by phosphorylation 4 h after treatment with siRNA si5 but not siRNA si6. This indicates that the sequence specific activation of TAK1-D by short dsRNAs appears to be a general phenomenon occurring in various mammalian cell types.

P38 MAPK as well as SPK/JNK have a large number of downstream targets. Amongst these, the phosphorylation of the cell cycle control phosphatase cdc25 (Bulavin et al., 2001; Goss et al., 2003) are of particular interest, as these phosphorylations have the potential to transduce an immediate and direct effect of TAK1-D activation to the cell cycle. The inventors looked at the subcellular distributions of cdc25 isoforms in NCI-H460 cells, which are shown in FIG. 3D. Cdc25C was found to be exclusively cytoplasmic and phosphorylated on S216. This indicates that cdc25C does not take part in the classic activation of nuclear cyclin dependent kinases through removal of the inhibitory phosphorylation. In contrast, both cdc25A and cdc25B were found in the nucleus and therefore capable of cell cycle control. The upper panel of FIG. 3D shows that the intensity of the upper band, recognized by the cdc25A antibody increases in intensity within 2 h after the addition of siRNA si5. The occurrence of this shifted form of cdc25A is indicative of phosphorylation and inactivation of cdc25A (Zhao et al., 2002). The amount of cdc25B in the nucleus decreases with kinetics similar to the phosphorylation of cdc25A, indicative for a phosphorylation dependent translocation and proteolytic digestion of cdc25B (Cans et al., 1999). Therefore, it can be concluded that activation of TAK1-D in NCI-H460 cells leads to an inactivation of cdc25A and cdc25B through p38 MAPK and SAPK/JNK mediated phosphorylation and proteolytic destruction.

Example 2

Activation of Tak1-D is Functionally Required for the dsRNA Triggered Activation of the Stress-Activated Protein Kinase Cascade In order to prove that the activation of Tak1-D is indeed required for the dsRNA mediated activation of the p38 MAPK and SAPK/JNK pathways a dominant-negative Tak1-D was constructed. It has been demonstrated that mutation of Lysine at position 63, which is required in the ATP binding site of the enzyme (Brown et al., 2005) to Tryptophan leads to a loss of catalytic activity and also exerts a dominant-negative effect on wild-type Tak1 (Edlund et al., 2003). Therefore an adenoviral vector was constructed which contained the mutated Tak1-D cDNA (K63W) under the control of the CMV promoter.

Figure 4:
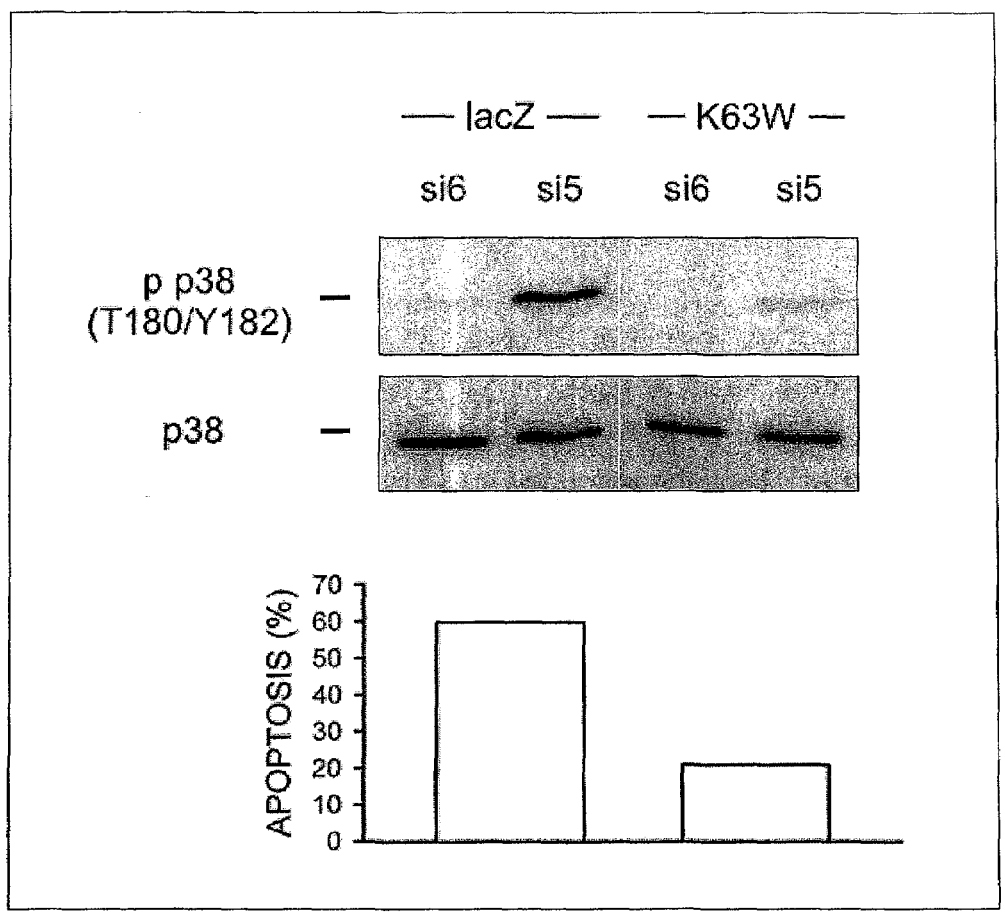
FIG. 4: Transfection of HCI-H460 cells with dominant-negative Tak1-D (K63W) significantly reduced the dsRNA mediated activation of p38 MAPK and subsequent apoptotic response.

In the experiment shown in FIG. 4, H460 cells were infected with adenoviral vectors containing the dominant-negative Tak1-D (K63W) or with a control vector coding for the sequence of β-galactosidase. 48 h after infection with a MOI of 2, cells were treated with 20 nM dsRNA for 4 h. It is evident from the top panel that the dsRNA si5 induced activating phosphorylation of p38 MAPK is significantly reduced in cells expressing the dominant-negative Tak1-D. The bar graph shows that the cellular apoptotic response, determined 48 h after siRNA treatment, and to be described in the following sections in more detail, is significantly reduced by inactivation of Tak1-D catalytic activity.

These data clearly demonstrate that splicing variant D of Tak1 is the upstream kinase triggering p38 MAPK and SAPK/JNK activation in response to double-stranded RNAs of specific sequence.

Example 3

The Tak1-D TAB1 Complex can be at Least be Partially Activated by Specific dsRNAs in a Cell-Free System Although the effect of the dominant-negative Tak1-D proves that the activation of the stress-activated protein kinase cascades is triggered by Tak1-D, it does not rule out the presence of an upstream signaling molecule which is capable of activating Tak1-D in response to sequence specific dsRNA. To test if any additional molecules are required for the dsRNA dependent activation of Tak1-D, the system was reconstituted in vitro using purified proteins. In vitro studies of Tak1 are complicated by the fact that recombinant Tak1 expressed in mammalian cells is catalytically inactive and requires co-expression of its binding protein TAB1 to gain protein kinase activity (Sakurai et al., 2000). Unfortunately, co-expression with TAB1 is sufficient to activate Tak1-D, requiring no other co-factors (Sakurai et al., 2000).

FLAG-tagged TAK1-D and HIS-tagged TAB1 were co-expressed in HeLa cells and the proteins were purified through immunoprecipitation with an anti-FLAG antibody.

Figure 5:
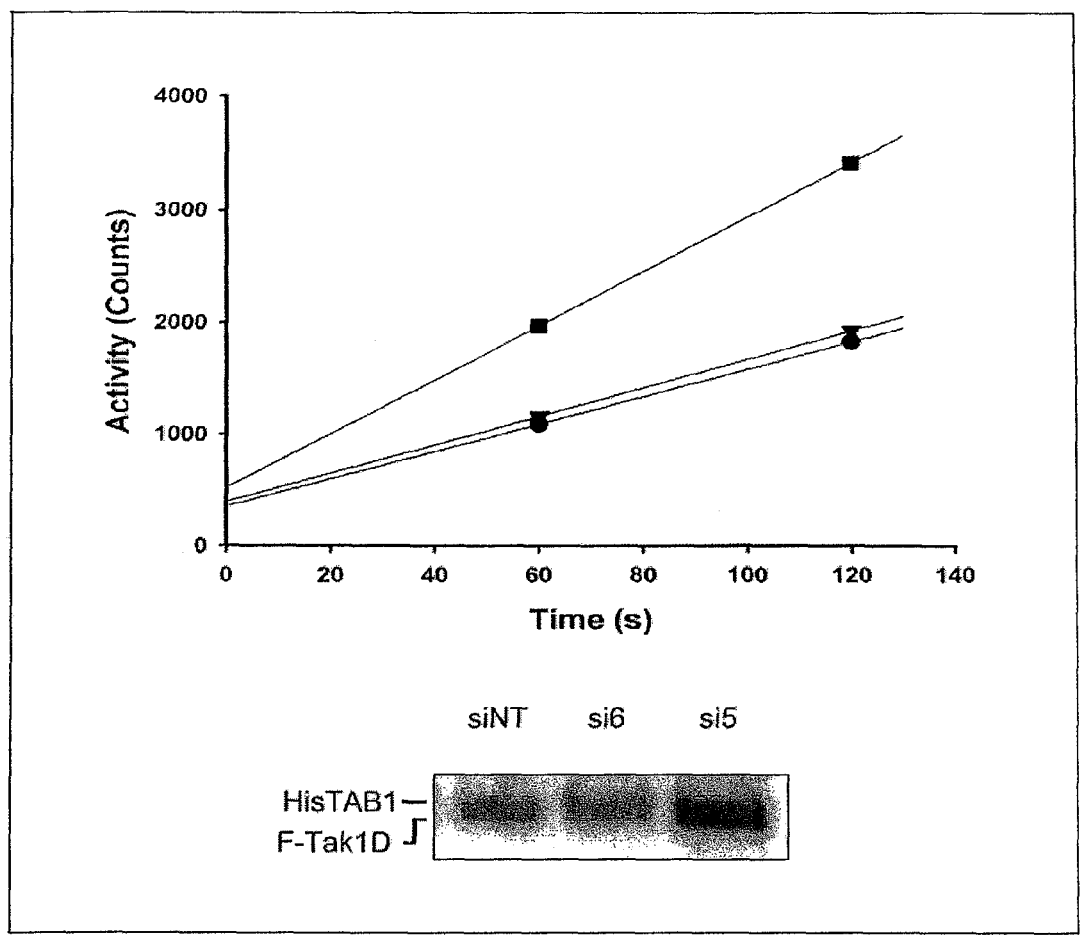
FIG. 5: In vitro kinase assay showing that autophosphorylation of the Tak1-D/TAB1 complex is increased in the presence of dsRNA si5.

Despite the above mentioned problems with the in vitro system, dsRNA si5 but not RNA si6 nor the scrambled dsRNA siNT increased the autophosphorylation activity of the Tak1-D/TAB1 complex as shown in FIG. 5. The insert in FIG. 5 shows the autoradiograph of a polyacrylamide gel separating the proteins 2 min after incubation with [$^-32$]P ATP.

The kinetics of the autophosphorylation reaction presented here demonstrates that the interaction between the dsRNA and the protein complex consisting of Tak1-D and TAB1 in vitro is sufficient to increase the kinase activity of Tak1-D.

Example 4

Sequence Features of dsRNAs Required to Activate Tak1-D

Figure 6:
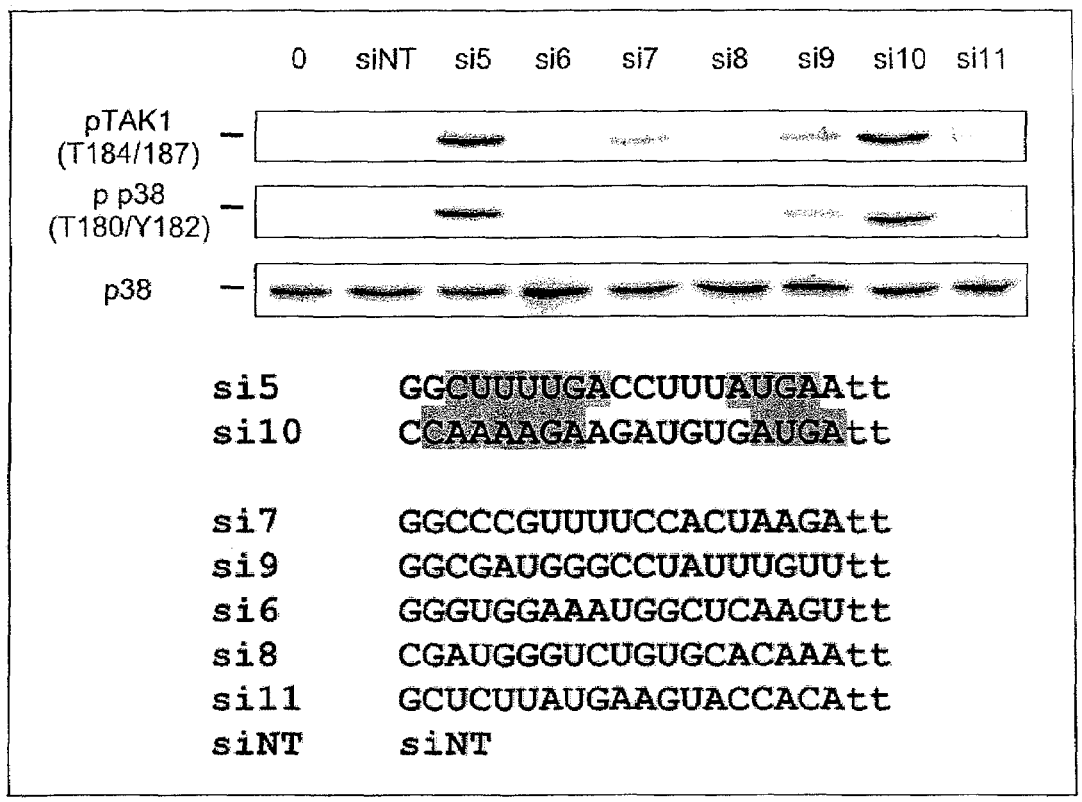
FIG. 6: Activation of TAK1-D by dsRNAs of specific sequence in intact cells. Transfection of NIH-H460 cells with randomly chosen siRNAs demonstrates that the activation of the TAK1-D p38 pathway depends on the siRNA sequence and siRNAs si5 and si10 activate the pathway most effectively (SEQ ID NOS: 2, 11, 12, 13, 14, 15 and 16).

Having demonstrated that the activation of Tak1-D depends on the specific sequence of the short dsRNA it is interesting to further elucidate the connection between RNA sequence and Tak1-D activation. The structure of Tak1D, which has been partially characterized only recently (Brown et al., 2005), makes it unlikely that the enzyme interacts with a specific base sequence but does not exclude the possibility that a certain RNA sequence lead to structural features of the nucleic acid, which is able to activate Tak1-D. To test this hypothesis several randomly chosen siRNAs were screened for their capability to activate Tak1-D. The Western blot in FIG. 6 shows that RNA si5 as well as the RNA designated si10 is able to activate Tak1-D and consecutively p38 MAPK. RNA si9 shows a slight activation of p38 MAPK while the others do not activate it at all.

The lower panel in FIG. 6 lists the sequences of the sense strands of the molecules used. If one compares the sequences of the two active RNAs (si5 and si10) it is clear that both molecules have two sequence motifs in common: in the 5' region: C followed by 4 consecutive A or U ribonucleotides followed by the sequence GA; in the 3' region: the sequence AUGA. These sequence similarities suggest that these sequence motifs might play a role in the activation of TAK1-D. To gain additional insight into the significance of these sequence motifs and to test the influence of sequence modifications on the ability of a short dsRNA molecule to activate Tak1-D, a number of small dsRNA molecules were synthesized and tested for their ability to activate Tak1-D and its downstream target p38 MAPK.

Figure 7:
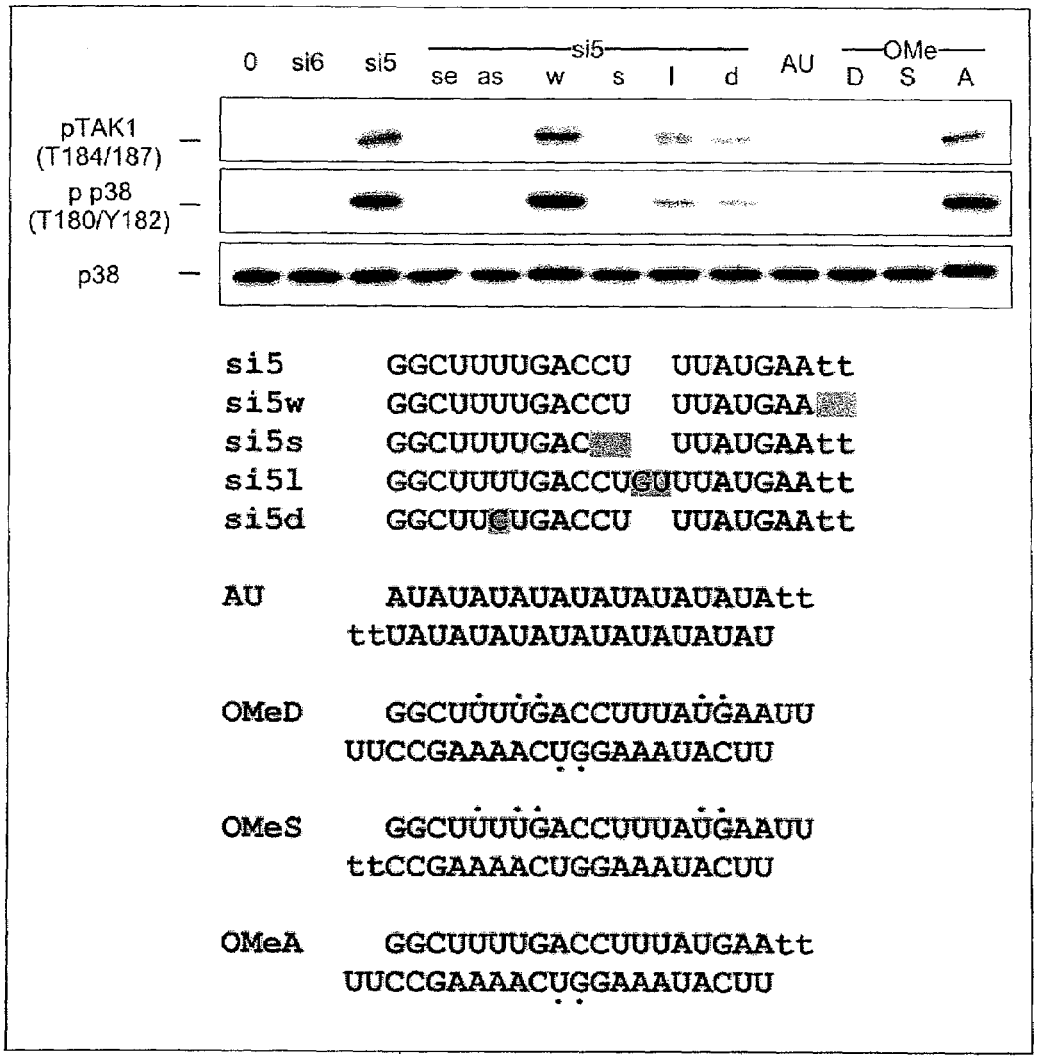
FIG. 7: Activation of TAK1-D by dsRNAs of specific sequence in intact cells. Consequences of modifications of the sequence of siRNA si5 on the activation of TAK1-D and its downstream target p38 MAPK in NCI-H460 cells, si5, si5w, si5s, si5l, and si5d (SEQ ID NOS:2, 1, 17, 18, and 19) are double-stranded RNAs and the aligned sequences of these molecules are shown, si5se and si5 as are single-stranded RNAs with the si5 sense and si5 antisense sequence. Molecules AU (control, SEQ ID NO:21 and 22) OMeD (SEQ ID NO:23 and 24), OMeS (SEQ ID NO:25 and 26), and OMeA (SEQ ID NO:27 and 28) are dsRNAs modified with a 2'OMe group at the dot marked bases.

FIG. 7 shows the sequence of these molecules and their effect on the TAK1-D p38 pathway. The left three lanes show the already described effects of siRNA si6 and si5 as a control. The following lanes show the effect of modification to the sequence of siRNA si5. In the lanes designated si5se and si5as, only the sense or the antisense strand of si5 were transfected. Transfection of NCI-H460 cells with single-stranded RNA molecules with the sequence of the si5 sense strand (si5se) and the si5 antisense strand (si5as) fails to activate TAK1-D, indicating that double-stranded RNA is required. Next, an siRNA named si5w was synthesized which did not possess the 3' dT overhangs typical for siRNAs. The strong effect of the molecule with both overhangs deleted proved that these structures are not required. It can be seen that the deletion of these 4 bases did not impair the ability of the molecule to activate Tak1-D. It can therefore be concluded that the 3' end structures and possibly also the 5' end groups are of no importance for the Tak1-D activating capability of the molecule. This is a very interesting and important finding, as it shows that dsRNAs can be modified at the 3' terminus and still keep their Tak1-D activating capability. In addition, it demonstrates that other RNA molecules which contain dsRNA structures like stem-loops can be efficient activators of Tak1-D mediated cell death in H460.

Next, it was tested whether other changes in the length of the si5 molecule have similar consequences. DsRNA si5s has two ribonucleotides in the middle of the molecule deleted. Surprisingly though the molecule had the same length as si5w the deletion completely abolished its ability to activate Tak1-D. Extending the length of the molecule by adding 2 ribonucleotides in molecule si5l significantly reduced its activity, but a small activation of Tak1-D and p38 MAPK could still be observed. These data indicate, as the central region of the molecule does not seem to be very important if one compares the effect of si5 and si10 in FIG. 6, that the spacing between the conserved CUUUUGA and AUGA motifs seems to be important. To investigate the role of the homopolymeric stretch of 4 A or U found in the activating RNAs si5 and si10 (FIG. 6), one U was changed to a C in dsRNA si5d. This single base change significantly reduced the capacity of the molecule to activate TAK1-D indicating the importance of this motif. When one compares the sequence of the activating siRNAs si5 and si10 in FIG. 6 with the other sequences, it can be noted that they contain a high proportion of A and U bases. To test whether this sequence feature is important for TAK1-D activation, a dsRNA with alternating A and U bases was constructed (AU). It can be seen in FIG. 7 that this sequence does not activate the TAK1-D pathway.

Sequence specificity has also been reported for the activation of the innate immune response (Judge et al., 2005) by siRNAs. In an effort to design dsRNA molecules with minimal activation of the inflammatory response, it has been demonstrated that substitution of the 2'-OH group of the ribonucleotide with a 2'-O-methyl group reduced the inflammatory reaction without reducing the mRNA silencing effect of the molecule (Judge et al., 2006). As such modifications would be beneficial for the intended in vivo application of Tak1-D activating dsRNA, the influence of 2'-Omethylation is shown in the right 3 lanes of FIG. 7. In the RNA sequences, a dot above or below the base indicated a 2'-O-methyl modification of the base. When a molecule of the same sequence as si5 with 2'-Omethyl on both strands (OmeD) was used, no activation of Tak1-D could be detected. The same is true for RNA OmeS, which has several bases of the sense strand modified. In contrast to these two molecules, modification of U and G by 2'-O-methylation in the antisense strand only did not reduce the ability of the molecule to activate the stress activated protein kinase pathway.

Two conclusions can be drawn from these data: (1) the central part of the sense, but not the antisense strand, seems to be important for Tak1-D activation which provides some information about the interaction of these molecules in their physiologic environment; (2) there are several bases in the sequence which can be modified by 2'-O-methylation to reduce possible inflammatory responses in vivo.

Example 5

Tak1-D Binds to the Ribosome

The long splicing variants of Tak1, Tak1-A and Tak1-B were found localize either to the plasma membrane during activation or are otherwise found in the cytoplasm (Jiang et al., 2002). To investigate whether the short splicing variant Tak1-D also shows this distribution pattern, subcellular fractionation experiments were performed.

Figure 8:
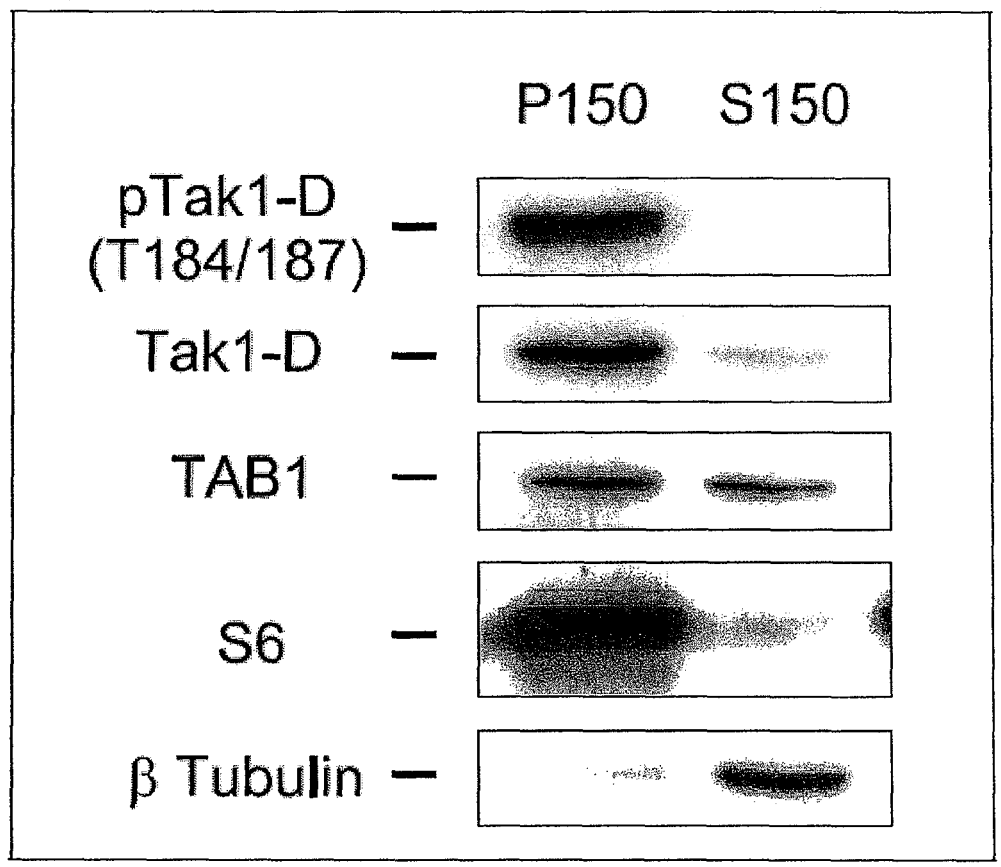
FIG. 8: Western blot showing the subcellular fractionation of H460 cells. Activated phosphorylated Tak1-D was found exclusively in the ribosomal fraction.

Somewhat unexpectedly, activated Tak1-D was found in the ribosomal fraction. Ribosomes were prepared using standard procedures (Samuel, 1981). Briefly, cells were lyzed 4 h after treatment with 20 nM siRNA si5 in a buffer containing 20 mM Tris (pH 7.5), 120 mM KCl, 1 mM MgCl$_2$, and 0.5% NP40. After removal of the nuclei and heavy organelles by centrifugation at 10,000 g for 10 minutes, the lysate was fractionated into a pellet (P$_{150}$) and a supernatant (S$_{150}$) by a 1 h centrifugation at 150,000 g. The bottom panel of FIG. 8 depicts the quality control of the separation, as the ribosomal protein S6 can only be found in the P$_{150}$ fraction. The figure also demonstrates by using a Tak1-D reactive antibody that most of the Tak1-D protein is found to be associated with the ribosomes. Nevertheless, a significant part could also be found in the S$_{150}$ fraction containing cytoplasmic proteins. In contrast, when an antibody specific for phosphorylated Tak1-D was used, the activated form could be exclusively detected in the ribosomal fraction (upper panel). The Tak1 binding protein TAB1 could be detected in both fractions, indicating that ribosomal Tak1-D is probably complexed with its binding protein TAB1.

Figure 9:
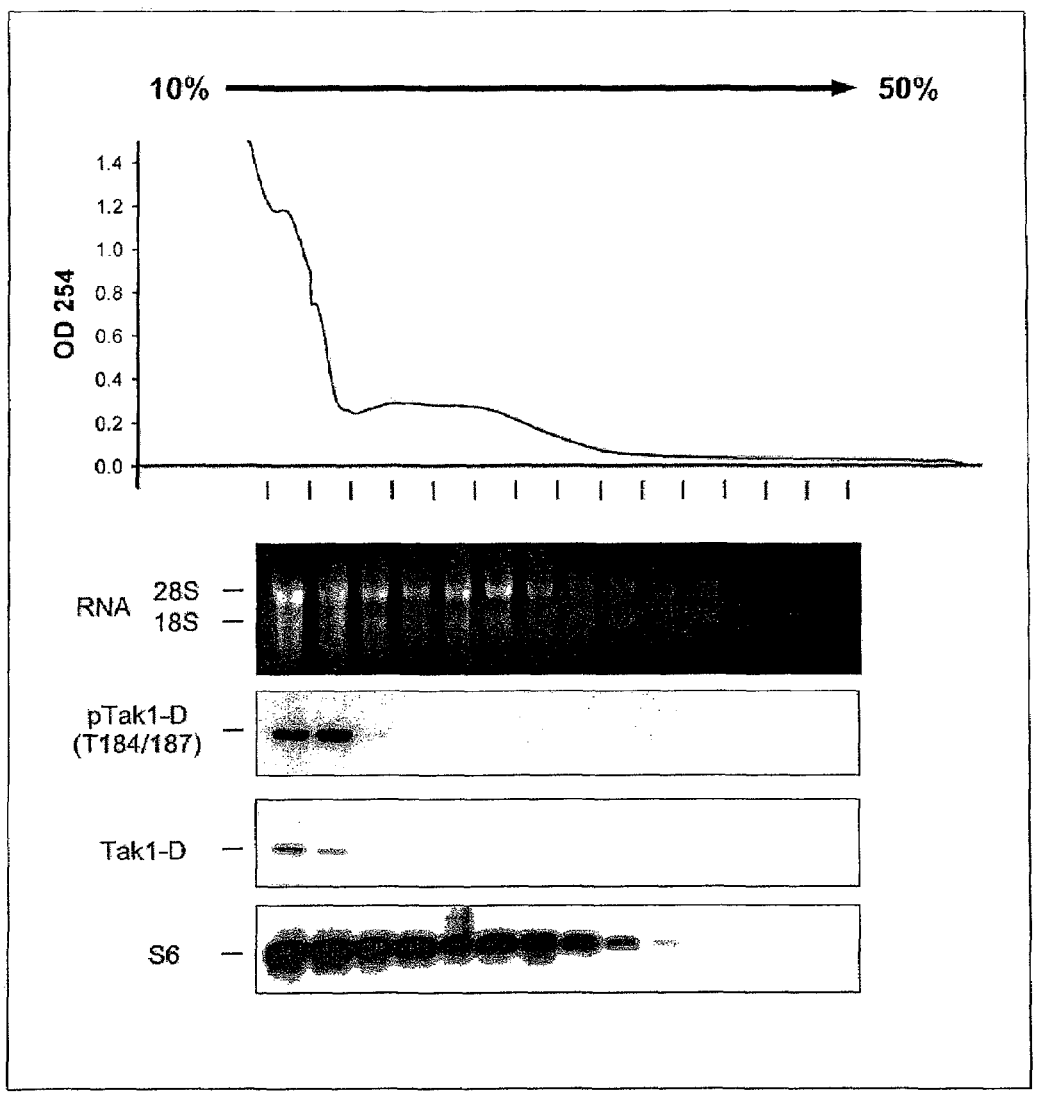
FIG. 9: Succrose density gradient centrifugation of ribosomes shows that activated Tak1-D cannot be found in the polysome fraction.

To investigate whether Tak1-D is bound to inactive ribosomes or to translationally active polysomes, the ribosomes were separated on a 10% to 50% sucrose gradient. The experimental protocol was exactly the same as previously published (Lu et al., 2006). The results of this separation are shown in FIG. 9. The upper panel shows the nucleic acid contents of the various fractions of the gradient as absorption at 254 nm. The corresponding rRNAs are shown in a ethidium bromide stained formaldehyde/agarose gel in the panel below. Western blot analysis using an antibody specific against phosphorylated activated Tak1-D shows a significant signal only in the first two fractions indicating that activated Tak1-D does not bind to transcriptionally active polysomes. The distribution of total Tak1-D also shows this distribution. As a control, the distribution of the ribosomal protein S6 is shown in the bottom panel.

The exclusive binding of activated Tak1-D to ribosomes which do not take part in translationally active polysomes gives room for the speculation that activation of Tak1-D might not only trigger stress-activated protein kinase cascades but also exert some control on the activity of the ribosome.

Example 6

Activation of Tak1-D Leads to Cell Cycle Arrest and Apoptosis in the NSCLC Cell Line H460

P38 MAPK and SAPK/JNK, which are activated by Tak1-D as demonstrated above, have a large number of downstream targets. Most prominent among those are several transcription factors, which are responsible for the change in gene expression induced by the activation of the stress-induced protein kinase pathway. Apart from the modulation of gene expression, several other downstream effectors directly phosphorylated by p38 MAPK or SAPK/JNK have been described. Among those, the inactivation of the cell cycle control phosphatases CDC25 (Bulavin et al., 2001; Goss et al., 2003) are particularly interesting, as a pronounced effect on the cell cycle can be expected from the inactivation of cdc25A and cdc25B.

To test this hypothesis, H460 cells were pulse labeled with BrdU for 15 min at various time points after treatment with siRNA si5 and analyzed by flow cytometry immediately afterwards. FIG. 10A shows the DNA content on the x-axis and the BrdU signal on the y-axis. FIG. 10A shows that within a few hours after transfection of NCI-H460 cells with siRNA si5 the number of cells in the S phase of the cell cycle drops to about half of the number found prior to the addition of the si5 siRNA. In particular, it can be seen that the fraction of cells in the S phase of the cell cycle drops from 48% in untreated cells to 27% 4 h after incubating the cells with 20 nM siRNA si5. The right panel of FIG. 10A shows that 24 h after treatment with siRNA si5 DNA synthesis has ceased almost completely. Specifically, 24 h DNA synthesis was found to have ceased in almost every cell. Because the fraction of cells containing a nuclear DNA amount specific for G$_1$, S, or G$_2$ cells did not change during the first 24 h after addition of siRNA si5, it can be concluded that activation of TAK1-D leads to an arrest of NCI-H460 cells in the G$_1$, S, and G$_2$ phase of the cell cycle.

Cell cycle arrest triggers programmed cell death in many tumor cell lines. As shown in FIG. 10B this also applies for TAK1-D mediated cell cycle arrest in NCI-H460 cells. Twenty four h after treatment with siRNA si5 cells from the G$_1$ and the S phase of the cell cycle show caspase 3 cleavage, indicative for the activation of the apoptotic pathway. After 48 h, the fraction of G$_1$ and S phase cells staining positive for cleaved caspase 3 is higher, still no Caspase 3 cleavage could be observed in G$_2$ phase NCI-H460 cells. The fact that NCI-H460 cells undergo classical apoptosis after TAK1-D induced cell cycle arrest is further demonstrated by the cleavage of the Caspase 3 substrate PARP shown in FIG. 10C and by the occurrence of nuclear condensation and fragmentation shown in the fluorescent micrographs of FIG. 10D.

As cell cycle arrest is incompatible with survival in many tumor cell lines the cellular response of H460 cells to the treatment with dsRNA si5 was investigated. The two micrographs in FIG. 10D, which show HOECHST 33342 stained nuclei of H460 cells, demonstrate that the cells exhibit typical apoptotic chromatin condensation and fragmentation 48 h after the activation of Tak1-D by dsRNA. In addition to the typical morphology the Western blot in FIG. 10D shows that PARP, a well-known Caspase substrate is cleaved within 24 h after the activation of Tak1-D providing biochemical evidence for apoptotic cell death.

Figure 11:
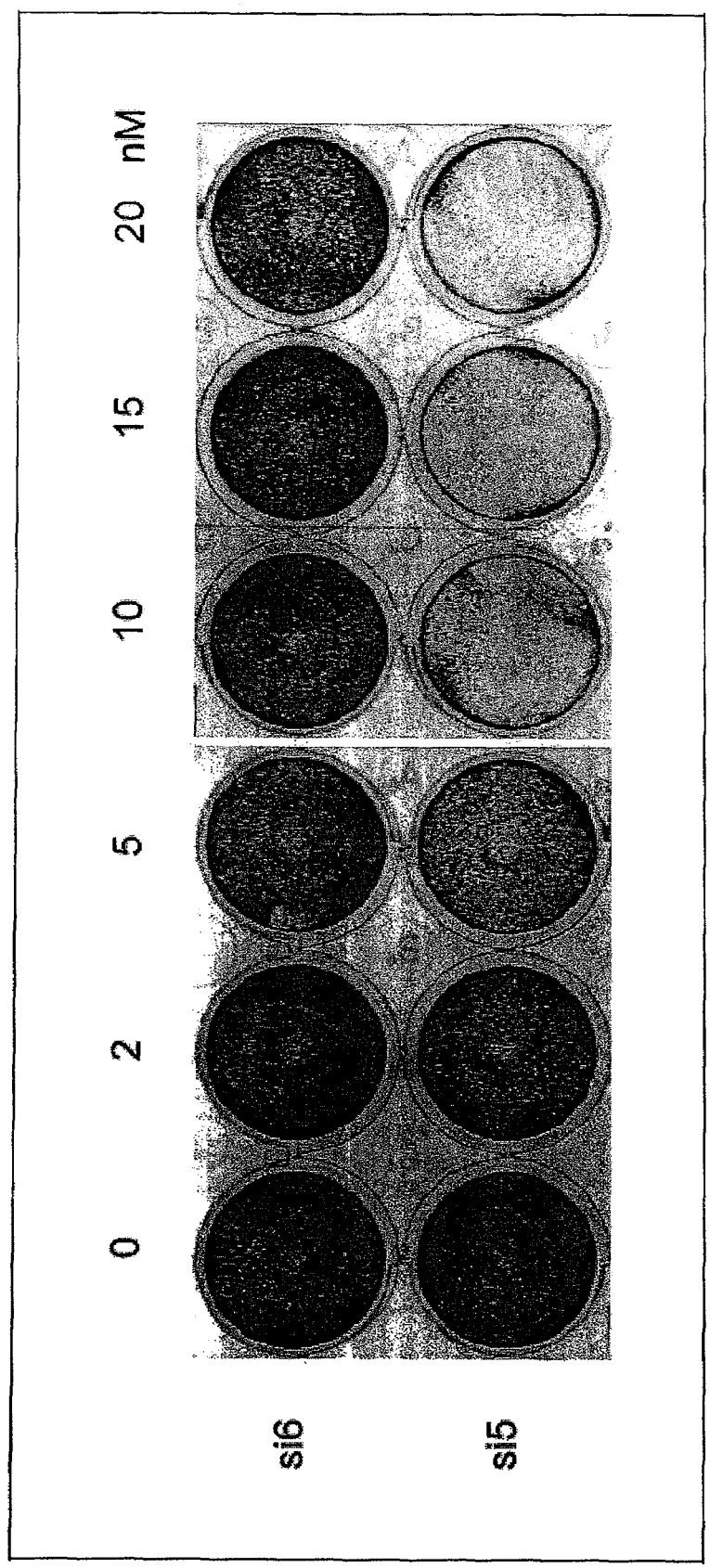
FIG. 11: Dose dependence of dsRNA si5 induced cell death in H460 cells stained in the culture wells with Crystal Violet 48 h after RNA treatment.

Having demonstrated that activation of Tak1-D by short dsRNAs of specific sequence leads to cell cycle arrest and apoptotic cell death in H460 cells, the dependence of this effect on the amount of transfected RNA remains an interesting question. To address this question, H460 cells were treated with different concentrations of siRNAs. FIG. 11 shows the result of a typical experiment. In this experiment, H460 cells were seeded at a density of 70,000 per well into a 12-well tissue culture plate. The next day, cells were treated with different concentrations of siRNA si5. Si6 at the same concentration was used as a control. Cells were fixed and stained with Crystal Violet in the wells 48 h later. FIG. 11 shows the image of the plate. It can be seen that a slight growth retardation occurs at RNA concentrations as low as 5 nM. However, a significant cell kill can be observed at higher doses ranging from 10 nM to 20 nM. It can also be noted the control siRNA si6, which targets the same mRNA does not show any significant cytotoxicity in the concentration range tested.

Taken together, the data presented here demonstrate that activation of Tak1-D by a short dsRNA of specific sequence induced apoptotic cell death in a NSCLC cell line in a dose dependent way.

Figure 12:
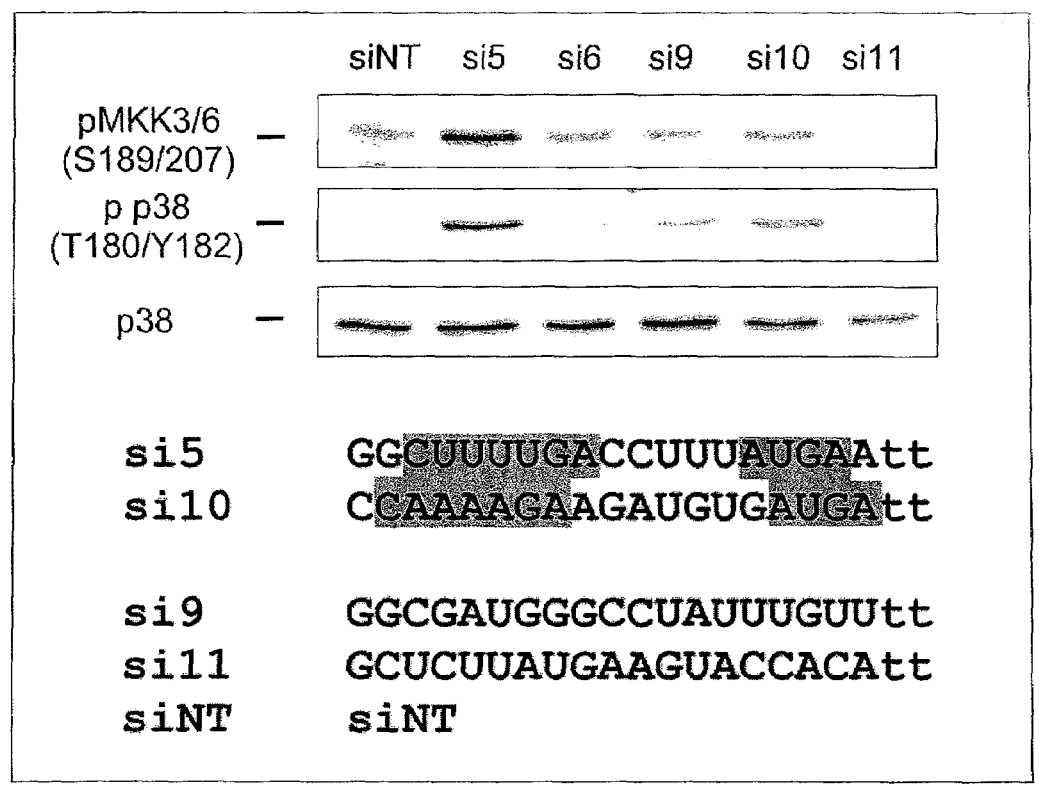
FIG. 12: Western blots showing that the p38 MAPK cascade is activated by short dsRNAs of similar sequence in HCC2279 NSCLC cells (SEQ ID NOS:2, 11, 13, and 16).

Example 7 dsRNAs of Specific Sequence Also Lead to Growth Arrest and Cell Death in Other NSCLC Cell Lines but not in Non-Malignant Cells Like HBECs or Fibroblasts A possible application for the above mentioned findings in cancer therapy requires data on the effects of dsRNA mediated activation of Tak1-D in other tumors and in normal tissues. To test whether dsRNA mediated cell killing also occurs in other tumor cell lines, the NSCLC cell line HCC2279 was chosen. This cell line originated from an adenocarcinoma and was initially described by Wistuba et al. (1999). FIG. 12 shows that the p38 MAPK cascade is activated in HCC2279 cells by RNAs of the same sequence, which have been shown to activate it in H460 cells as shown in FIG. 6. Specifically, it can be seen that siRNA si5 and to a lesser degree siRNA si10 activate p38 MAPK in the same way in 2279 cells as has been shown in H460 cells in FIG. 6.

Figure 13:
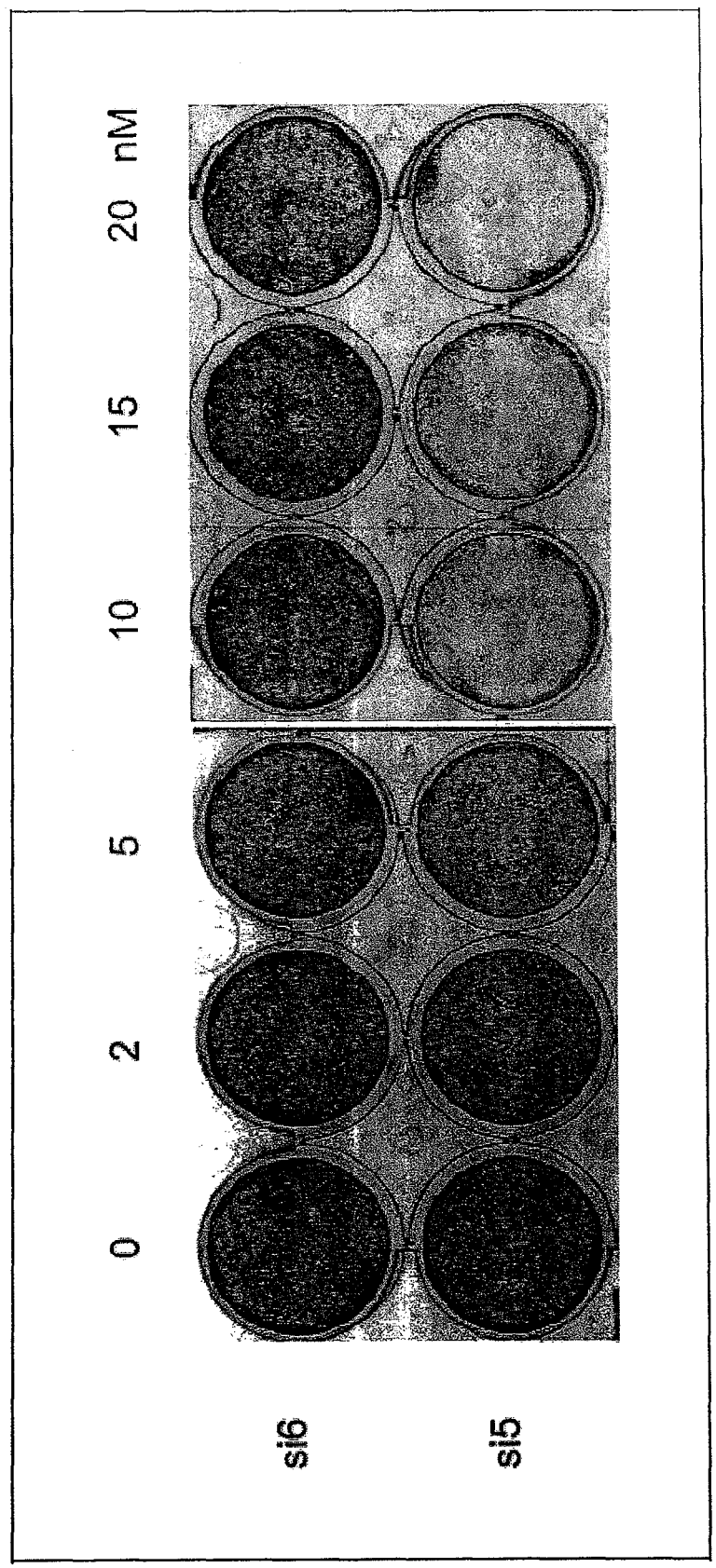
FIG. 13: Dose dependence of siRNA si5 induced cell death in HCC2279 cells stained in the culture wells with Crystal Violet 48 h after RNA treatment.

To test whether the dsRNA mediated activation of the stress-activated protein kinase cascade also leads to cell death in HCC2279 cells, the cells were plated in a 12 well multi-well plated, treated with siRNA si5 or as a control with siRNA si6 and stained with Crystal Violet 48 h later. A similar experiment with H460 cells is shown in FIG. 11. The image shown in FIG. 13 demonstrates, that a small effect on cell growth of HCC2279 cells can be observed 48 h after treatment with 5 nM si RNA si5. In contrast treatment with higher concentration ranging between 10 and 20 nM lead to significant cell death comparable to the results shown for H460 cells in FIG. 11. Again, the siRNA si6, which targets the same mRNA as siRNA si5 shows no significant toxicity in the concentration range tested. The data presented as well as the widespread expression of Tak1-D in tissues like lung, brain, liver, and prostate (Dempsey et al., 2000) makes targeted activation of TAK1-D by specific dsRNA an interesting treatment opportunity for these types of cancer.

Figure 14:
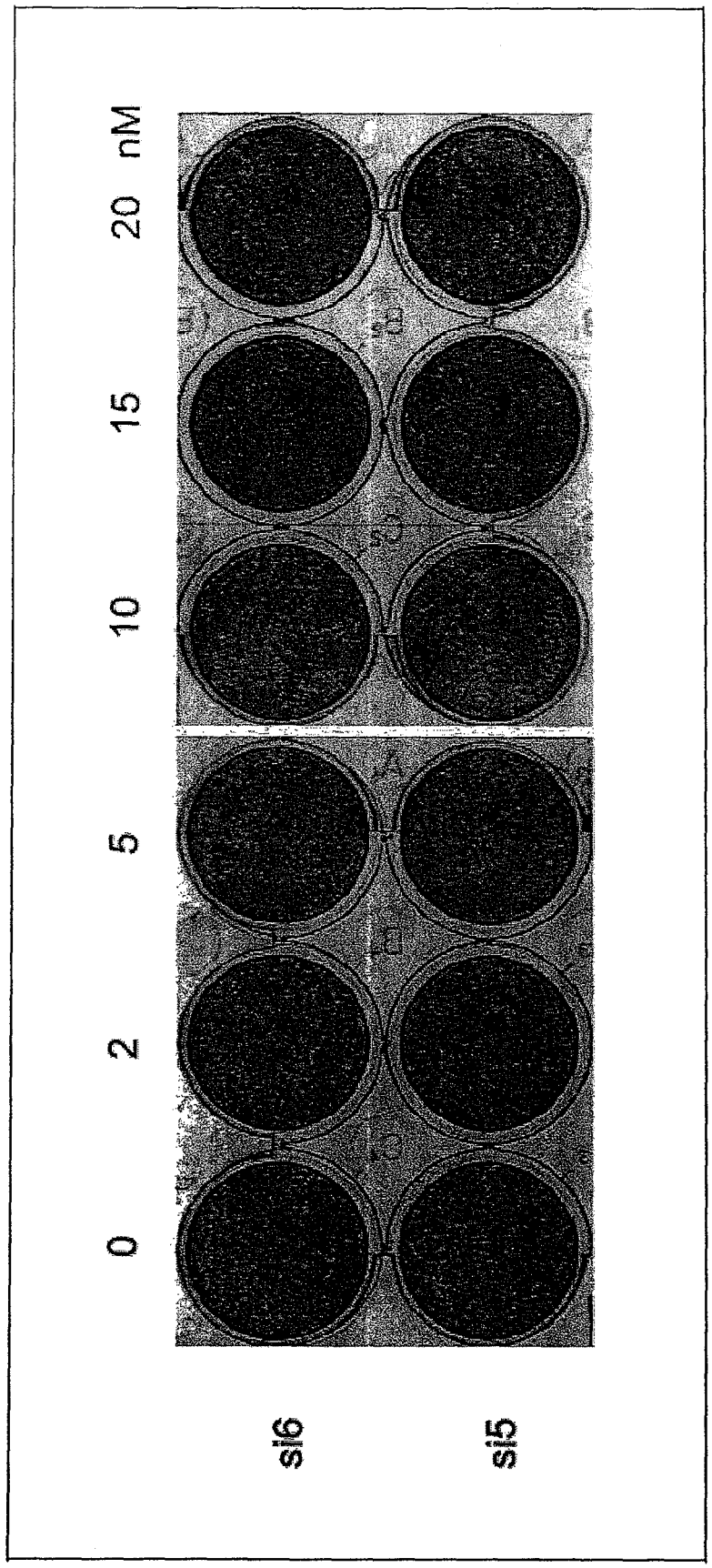
FIG. 14: Normal human skin fibroblasts show no cytotoxicity or growth delay after treatment with siRNA si5.
Figure 15:
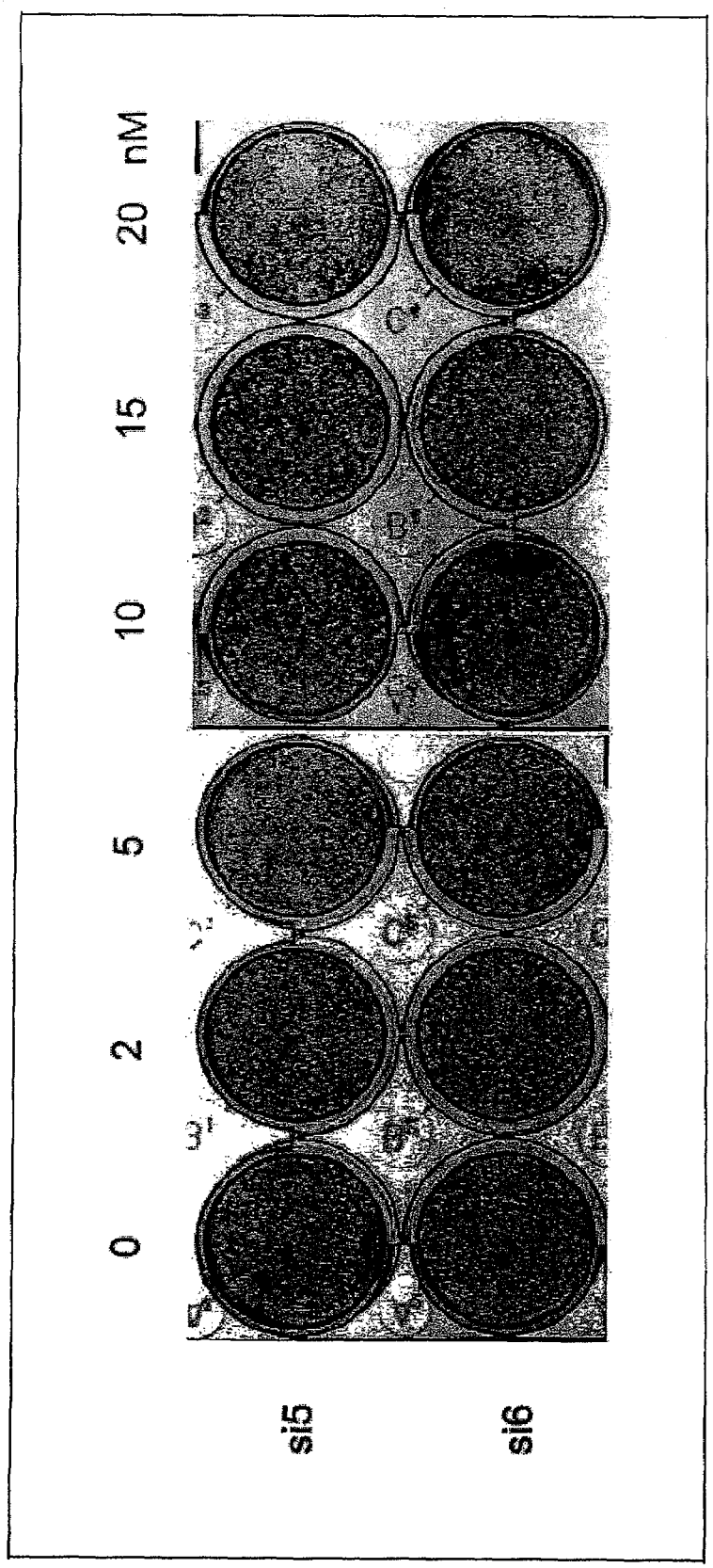
FIG. 15: Human bronchial epithelial cells (HBEC) show no cytotoxicity or growth delay after treatment with siRNA si5.

In order to obtain preliminary data describing the response of normal tissue cells to dsRNA mediated Tak1-D activation normal human fibroblasts as well as human bronchial epithelial cells (HBEC) were plated into 12-well multiwell plates, treated with siRNA si5 or si6 in different concentrations and stained with Crystal Violet 48 h later. FIG. 14 shows the reaction of normal human skin fibroblasts to siRNA si5. In contrast to H460 cells (FIG. 11) or HCC2279 cells (FIG. 13), no growth inhibitory or cytotoxic effect could be observed in the fibroblasts when treated with siRNA si5 using RNA concentrations up to 20 nM. The same hold true for HBEC shown in FIG. 15. No si5 induced cell death is visible for RNA concentration up to 20 nM, indicating that RNA si5 does not exhibit a specific cytotoxic effect like the one demonstrated for the NSCLC lines H460 and HCC2279. These data give a first indication that a differential effect between normal and tumor cells exist which might be caused by differences in cell cycle control in these two cell types.

Example 8

Methods for Examples 9-Y

Cell culture. NCI-H460 non-small cell lung cancer cells were cultured in RPMI1640 medium supplemented with 10% FBS, 100 U/ml penicillin, and 100 µg/ml streptomycin. Cells were incubated at 37° C. in a humidified atmosphere containing 5% CO.

dsRNA and drug treatment of cells. siRNAs si5

```
5' GGCUUUUGACCUUUAUGAAtt 3'     (SEQ ID NO: 2)

3' ttCCGAAAACUGGAAAUACUU 5'     (SEQ ID NO: 3)
and si6
5' GGGUGGAAAUGGCUCAAGUtt 3'     (SEQ ID NO: 4)
3' gtCCCACCUUUACCGAGUUCA 5'     (SEQ ID NO: 5)
``` which are both directed against the mRNA of TLK1, were synthesized by Ambion and transfected by lipofection as described previously (Kodym et al., 2008b).

The p38 MAP kinase inhibitor SB-203580 (Calbiochem, San Diego, Calif., USA) as well as the SAPK/JNK inhibitor JNK inhibitor II (Calbiochem) were dissolved in DMSO and added to the cell culture medium to give a final concentration of 2 µM. The final DMSO concentration was less than 0.25%.

Ricin A (SIGMA, St. Louis, Mo., USA) was dissolved in unsupplemented RPMI1640 medium at a concentration of 100 µg/ml, mixed with an equal volume of 2.5% (vol/vol) Lipofectamine in RPMI1640 and incubated at room temperature for 20 minutes. The liposome Ricin A mixture was added to H460 cells covered with complete medium to a final concentration of 9 µg/ml.

Blasticidin S (Invitrogen. Carlsbad, Calif., USA) was added to the cell culture medium to give a final concentration of 100 µM. Puromycin (SIGMA) was used in the same way in a final concentration of 200 µM. Cycloheximide (SIGMA) was dissolved in water and added to the culture medium to give a final concentration of 25 µg/ml. G418 (Invitrogen) was used in a final concentration of 1 mg/ml. After addition of the drugs H460 cells were incubated at 37° C. for 90 minutes.

TAK1-D/K63W plasmid construction and transfection. The coding sequence of TAK1-D was amplified by PCR from H460 derived cDNA using Advantage-Taq polymerase (Clontech, Mountain View, Calif., USA). PCR based site directed mutagenesis (Landt et al., 1990) was used to introduce the K to W mutation at position 63. The PCR produced was cloned into the pIRESneo3 vector (Clontech). This bi-cistronic vector allowed the expression of TAK1-D/K63W and the selection marker neomycin phosphotransferase from the same mRNA. The plasmid was transfected into H460 cells using Lipofectamine 2000 (Invitrogen). Cells expressing TAK1-D/K63W or vector transfected control cells were selected by passaging the cells in the presence of 400 µg/ml G418. Prior to experiments G418 was removed from the culture medium for at least 1 passage.

Survival assay and apoptosis scoring. H460 cells were plated at a density of 70 000 cells per well in a 12-well plate. After an over night incubation cells were transfected with si5 as described above. Forty-eight hours after transfection cells were fixed and stained by incubating the monolayer for an hour in PBS containing 1% formaldehyde and 0.05% Crystal Violet. After a brief wash with water the plates were air dried. Apoptotic cells were identified and counted according to their nuclear morphology as described previously (Kodym et al., 2008a).

EMSA. Electrophoretic mobility shift assays for NFκB were performed as described previously (Kurland et al., 2001) using 3.5 µg of nuclear protein for each reaction.

Subcellular fractionation. About $10^4$ H460 cells growing in a 10 cm dish were transfected with 20 nM dsRNA si5 or si6. Six hours after transfection cells were washed twice in PBS and lyzed on ice for 10 minutes in a buffer consisting of 10 mM Tris (pH 7.5), 1.5 mM MgCl, 10 mM KCl, 0.5 mM DTT, 1 mM PMSF, 1 mM β-glycerophosphate, and 1 mM Sodiumorthovanadate. A crude nuclear pellet (P.7) was obtained by centrifugation at 700 g and 4° C. for 5 minutes. The supernatant was centrifuged at 10,000 g and 4° C. for 30 minutes producing the P10 pellet and finally separated by ultracentrifugation (Sorvall 90SE ultracentrifuge and Sorvall AH-629 rotor) at 150,000 g and 4° C. for 1 hour into pellet (P150) and supernatant (S150). Proteins from the S150 fraction were concentrated by precipitation with 10% trichloroacetic acid (TCA). All pellets were dissolved in SDS sample buffer.

Sucrose density gradients. Separation of ribosomes by sucrose density gradient centrifugation was performed basically as described previously (Lu et al., 2006). Briefly, about $10^6$ H460 cells growing in a 10 cm cell culture dish were treated with 100 μg/ml cycloheximide for 15 minutes to preserve polysomes or with 500 μM puromycin for 30 minutes to disrupt the polysomes. Thereafter, cells were lyzed on ice in a buffer containing 10 mM Tris (pH 7.4), 140 mM KCl, 1.5 mM MgCl, 0.5% NP40, 1.5 mM DTT, 100 μg/ml cycloheximide, 500 μg/ml heparin, 1 mM PMSF, and 500 U/ml RNAsin (Promega, Madison, Wis., USA). After a 10 minutes centrifugation at 10,000 g and 4° C. the supernatant was layered onto a 10-40% sucrose gradient and centrifuged in an ultracentrifuge (Sorvall 90SE and Sorvall AH-629 rotor) at 100,000 g and 4° C. for 2 (FIG. 3) or 4 hours (FIG. 4). The gradient was harvested with a peristaltic pump through a FPLC UV detector and 1 ml fractions were collected. From these fractions rRNA was extracted using TrizolLS (Invitrogen) and separated on a formaldehyde-agarose gel. Proteins for western blot analysis were precipitated with 10% TCA from the fractions and dissolved in sample buffer.

Fractionation of ribosome associated proteins. Fractionated dissociation of ribosome associated proteins was performed as described by Samuel (Samuel, 1981) by increasing the KCl concentration in the buffer. The only modification to the original protocol was that the sedimentation was performed by centrifugation at 150,000 g and 4° C. for 1 hour and salt washes were done at 4° C. for 20 minutes.

Measurement of protein synthesis by [$^{35}$S] methionine incorporation H460 cells were plated at a density of 10 cells/well in 12 well plates. On the next day cells were incubated with the dsRNAs for the given amount of time. Ten minutes prior to labeling the cell culture medium was replaced with cystein/methionine free RPMI. Thereafter, cells were incubated for 15 minutes in cystein/methionine free RPMI containing 40 μC/ml [$^{35}$S] methionine (Perkin Elmer, Waltham, Mass., USA).

In order to measure the incorporated radionuclide, cells were washed 5 times with 5% TCA, once with 70% ethanol and the proteins were solubilized in SDS-PAGE sample buffer. After addition of the samples to a liquid scintillation cocktail, [$^{35}$S] activity was determined in a LS6500 scintillation counter (Beckmann).

For SDS-PAGE cells were washed 3 times with PBS and proteins were solubilized by heating in non reducing sample buffer. After determination of the protein concentration (D protein assay, Bio-Rad, Hercules, Calif., USA) samples were reduced by the addition of DTT to a final concentration of 100 mM and separated in a 4-12% Bis-Tris gradient gel (NuPAGE, Invitrogen). The gel was dried after Coomassie blue staining and autoradiography was performed using a phosphoimager (Typhoon 9410, Amerham).

Immunofluorescence. H460 cells stably expressing TAK1-D fused on its c-terminus to a FLAG tag were generated as described above for the K36W mutant. Cells were transfected with 20 nM si5 or si6 and fixed in 4% formaldehyde 6 h later. After 15 min of fixation at room temperature cells were washed 3 times in PBS and permeabilized in methanol at −20° C. for 10 min. After one wash in PBS slides were blocked for 1 hour at room temperature in PBS containing 1% BSA. Thereafter, the cells were incubated over night at 4° C. in blocking buffer containing the following primary antibodies: mouse monoclonal anti-S6 ribosomal protein antibody (Cell Signaling #2317, Danvers, Mass., USA) diluted 1:25, rabbit anti FLAG antibody (SIGMA) diluted 1:200. After three 5 min washed in PBS the slides were incubated for one hour at room temperature in blocking buffer containing the following secondary antibodies: Alexa Fluor 488 conjugated anti-mouse antibody (Invitrogen) diluted 1:100, Cy3 conjugated anti-rabbit antibody (Jackson ImmunoResearch, West Grove, Pa., USA) diluted 1:200. After three 5 min washes in PBS cells were visualized by fluorescence microscopy. Images were acquired in the green Alexa Fluor 488 channel (S6 protein) and in the red Cy3 channel (FLAG tagged TAK1-D). These images were superimposed using the ImageJ software (Collins, 2007).

Immunoblot analysis. Western blotting was performed exactly as described previously (Kodym et al., 2008b). In addition to the primary antibodies previously mentioned (Kodym et al., 2008b) the following antibodies were used: S6 ribosomal protein (Cell Signaling #2217), DPM1 (Santa Cruz #sc-15836, Santa Cruz, Calif., USA), and Histone H3 (Cell Signaling #9715).

Example 9

The Kinase Activity of TAK1-D is Required for dsRNA-Triggered Activation of Stress Response and Induction of Cell Death The inventors have previously demonstrated (Kodym et al., 2008b) that treatment of H460 cells with a short dsRNA of a specific sequence (si5) leads to the phosphorylation of TAK1-D on threonine 184 and 187, to the activation of the stress-activated protein kinase cascade, and finally to apoptotic cell death. In order to demonstrate that the activation of TAK1-D is functionally required to trigger these events, H460 cells were stably transfected with a mutated from of TAK1-D, which lost its kinase activity by substituting the amino acid Lysine at position 63 in the ATP-binding site with Tryptophan (TAK1-D/K63W) (Sakurai et al., 2000). FIG. 1A shows that treatment of wild-type as well as vector transfected H460 cells with dsRNA si5 leads to phosphorylation of TAK1-D at the autophosphorylation sites T184 and T187 within 4 hours. The downstream kinases p38 MAP kinase and SAPK/JNK show activating phosphorylations at the specific threonine and tyrosine residues. In contrast a very significant reduction in the amount of activating phosphorylation of p38 MAP kinase as well as of SAPK/JNK can be observed in H460 cells transfected with the kinase inactivated TAK1-D mutant K63W. These data demonstrate a transdominant negative effect of TAK1-D/K63W on si5 induced activation of the p38 MAP kinase and SAPK/JNK signaling cascade.

It is interesting to note that TAK1-D/K63W transfection did not lead to an increased cellular concentration of TAK1-D as the antibody used in the upper panel of FIG. 16A does not distinguish between wild-type and K63W mutated TAK1-D. In an effort to explain this phenomenon TAK1-D mRNA levels were quantified by RT-PCR using wild-type and mutant specific primers. RT-PCR demonstrated (data not shown) that both cell lines express similar amounts of total TAK1-D mRNA but that this mRNA consists of wild-type and mutant mRNA in TAK1-D/K63W transfected cells. Therefore, H460 cells transfected with the dominant-negative TAK1-D mutant express both wild-type and mutant protein with the expression level of wild-type protein reduced, probably due to a feedback mechanism. The presence of both proteins in TAK1-D/K63W transfected cells explains the increased phosphorylation of TAK1-D at T184 and T187 after si5 treatment, as it has been shown that T187 is phosphorylated by intermolecular auto-phosphorylation (Singhirunnusorn et al., 2005).

FIG. 16B illustrates the effect of dominant-negative TAK1-D/K63W on dsRNA si5 induced cell death. The left image shows a section of a multi-well plate with crystal violet stained H460 cells 48 hours after transfection with dsRNA si5. While 5 or 10 nM si5 induces massive cell death in untreated H460 cells (H460-wt) as well as in vector transfected cells (H460-vec), H460 cells transfected with the dominant-negative TAK1-D/K63W survive the treatment with dsRNA si5. As a control the right image shows that no significant toxicity can be observed in any of the cell lines when transfected with the control RNA si6. Therefore, the dominant-negative effect of TAK1-D/K63W is not limited to si5 mediated activation of the stress-activated protein kinase cascades but also protects the cells against si5-induced cell death, demonstrating that functional TAK1-D is required for this cellular response to dsRNAs of specific sequence. As a slight growth inhibition of si5 transfected H460-K63W cells can be observed in FIG. 16B it is interesting to ask whether this is caused by an incomplete suppression of TAK1-D activity or by activation of other dsRNA-dependent stress pathways. To answer this question, the activation of the transcription factor NF-κB by dsRNA si5 was tested, as it well established that dsRNA triggered activation of PKR (Zamanian-Daryoush et al., 2000), TLR3 (Jiang et al., 2003), and RIG1/Mda-5 (Hiscott et al., 2006) leads to a downstream activation of NF-κB. FIG. 16C shows the electrophoretic mobility shift assay (EMSA) of nuclear protein of H460 cells, which were transfected with dsRNA si5 and si6. It can be seen that neither si5 nor si6 transfection lead to an activation of NF-κB activation after 6 hours. These data make it likely that the growth inhibition of H460-K63W treated with 10 nM si5 in FIG. 16B is caused by an incomplete suppression of endogenous TAK1-D activity.

Having established the functional role of TAK1-D in si5 mediated cell death it was tested whether activation of the stress induced protein kinase cascade is the causal mechanism triggering apoptosis after TAK1-D activation. H460 cells were treated with 2 μM of the p38 MAP kinase inhibitor SB-203580 in combination with 2 μM of the SAPK/JNK inhibitor JNK inhibitor II 30 minutes prior to transfection with 20 nM dsRNA si5. FIG. 16D shows that while the inhibitors had no effect on background apoptosis levels in untreated H460 cells the amount of apoptosis observed 24 hours after transfection with dsRNA si5 was significantly reduced. This indicates a functional role of p38 MAP kinase and SAPK/JNK in dsRNA triggered and TAK1-D mediated apoptotic cell death in H460 cells. However, FIG. 16D clearly shows that this protection against dsRNA induced apoptosis by the SB-203580/JNK inhibitor II combination in only partial. This can be most likely explained by the activation of other stress induced protein kinase pathways, which are insensitive to the inhibitors used like p38 MAP kinase gamma (Kuma et al., 2005).

Example 10

Subcellular Distribution of TAK1-D

Figure 17:
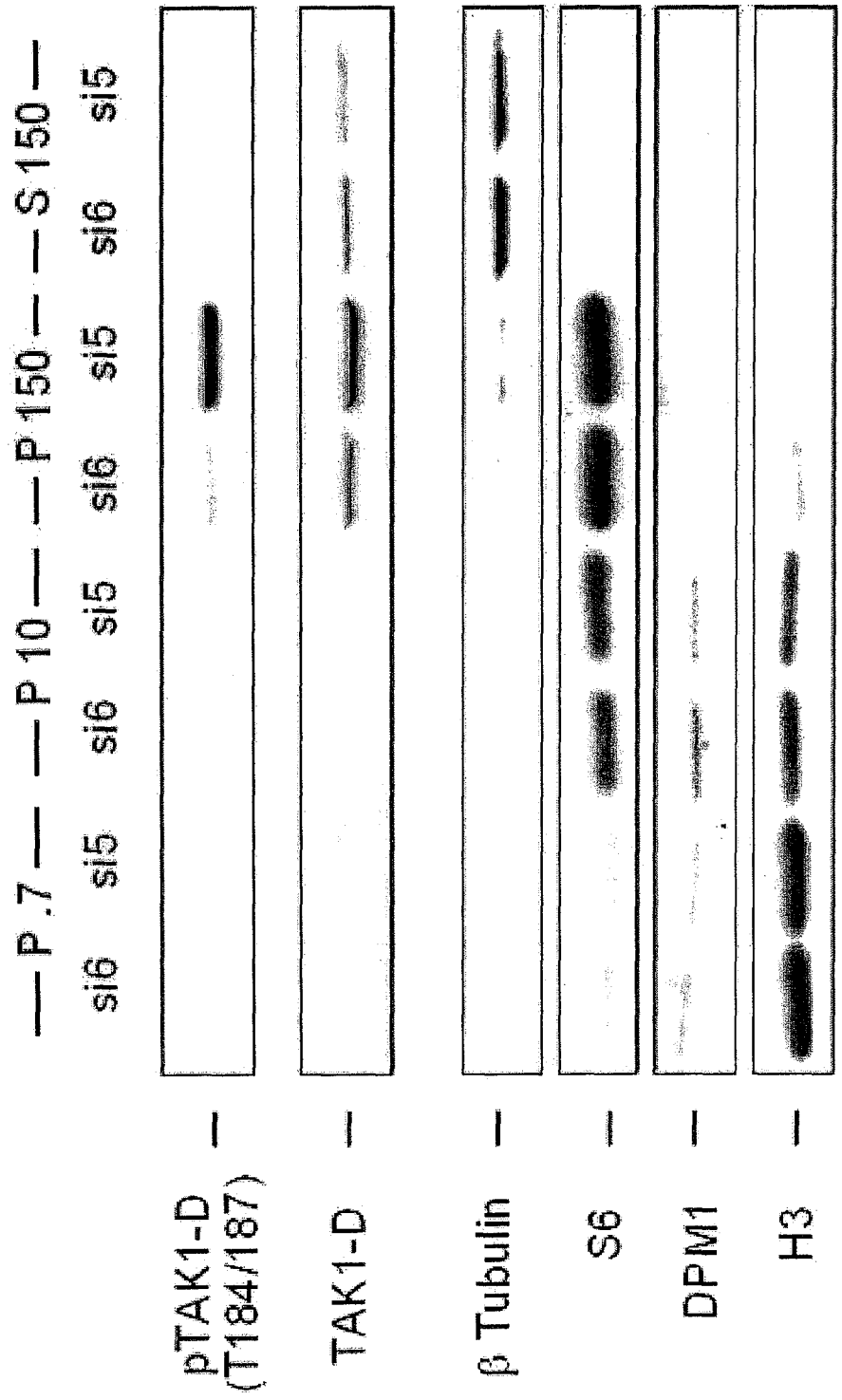
FIG. 17: Sub cellular localization of total and phosphorylated TAK1-D. H460 cells were treated with 20 nM dsRNA si5 and si6 for 4 h. After hypotonic lysis organelles were fractioned through centrifugation steps at 700 g, 10,000 g, and 150,000 g. 30 μg of protein from each fraction was separated by SDS-PAGE and analyzed by western blotting. The top panel shows that phosphorylated TAK1-D could be exclusively found in the 150,000 g pellet, while total TAK1-D protein could be found in the 150,000 g supernatant as well. The bottom panels show marker proteins for the different sub cellular compartments (β-tubulin: cytoplasma; ribosomal S6 protein: ribosomes; DPM1: rough endoplasmic reticulum; histone H3: nucleus).

To determine the sub cellular localization of TAK1-D, H460 cells were lyzed in hypotonic buffer and the sub cellular fractions were separated by centrifugation. FIG. 17 shows the western blot of equal amounts of protein obtained by the different centrifugation steps of H460 cells, which have been treated for 4 hours with si5 or with the control RNA si6, which does not activate TAK1-D (Kodym et al., 2008b). The immunoblots for the marker proteins β-tubulin, ribosomal S6 protein, dolicholphosphate mannose synthase 1 (DPM1), and histone H3 demonstrating the separation between cytoplasmic, ribosomal, rough endoplasmatic reticulum, and nuclear proteins. No TAK1-D was found in the 700 g pellet, which consisted mostly of nuclei, nor in the 10,000 g pellet, which contained heavy membranes and mitochondria. All of the TAK1-D protein appeared either in the pellet or in the supernatant after a 1 hour centrifugation at 150,000 g. While total TAK1-D protein was detectable in both fractions, the activated T184/T187 phosphorylated form was found exclusively in the pellet. In addition, when TAK1-D was activated by si5 the amount of TAK1-D in the pellet increased when compared to the control, indicating a translocation of the protein from the cytosol into the 150,000 g pellet. As the most prominent organelle in the P150 fraction is the ribosome, the association of phosphorylated TAK1-D with the ribosome was tested.

Example 11

Association of TAK1-D with the 80S Ribosome

As a certain amount of T184/T187 phosphorylation was detected in the 150,000 g pellet of the control cells shown in FIG. 17, ribosomes from untreated H460 cells were separated by centrifugation through a sucrose density gradient. The graph in the upper panel of FIG. 18A shows the absorbance profile measured at 254 nm for the ribosomes separated by the gradient into mono- and polysomes. While most of the total TAK1-D protein could be found on top of the gradient, all of the T184/T197 phosphorylated TAK1-D partitioned into the single fraction which contained the large 60S ribosomal subunit as well as the 80S monosomes. No T184/T187 phosphorylated TAK1-D was detectable in the polysomal fractions.

In order to identify the ribosomal subunit TAK1-D is associated with, TAK1-D phosphorylation was increased by treating the cells with si5 for 4 hours and the polysomes were disrupted by incubating the cells with the translation elongation inhibitor Puromycin. The upper panel in FIG. 18B shows the absorption profile after separating the ribosomes by sucrose density gradient centrifugation clearly distinguishing between the 40S and 60S subunits and the 80S monosomal fraction. Western blot analysis of the gradient fractions demonstrates that TAK1-D phosphorylated on T184 and T187 co-localizes with the 80S ribosomal fraction indicating that TAK1-D binds to the 80S ribosome.

Figure 19:
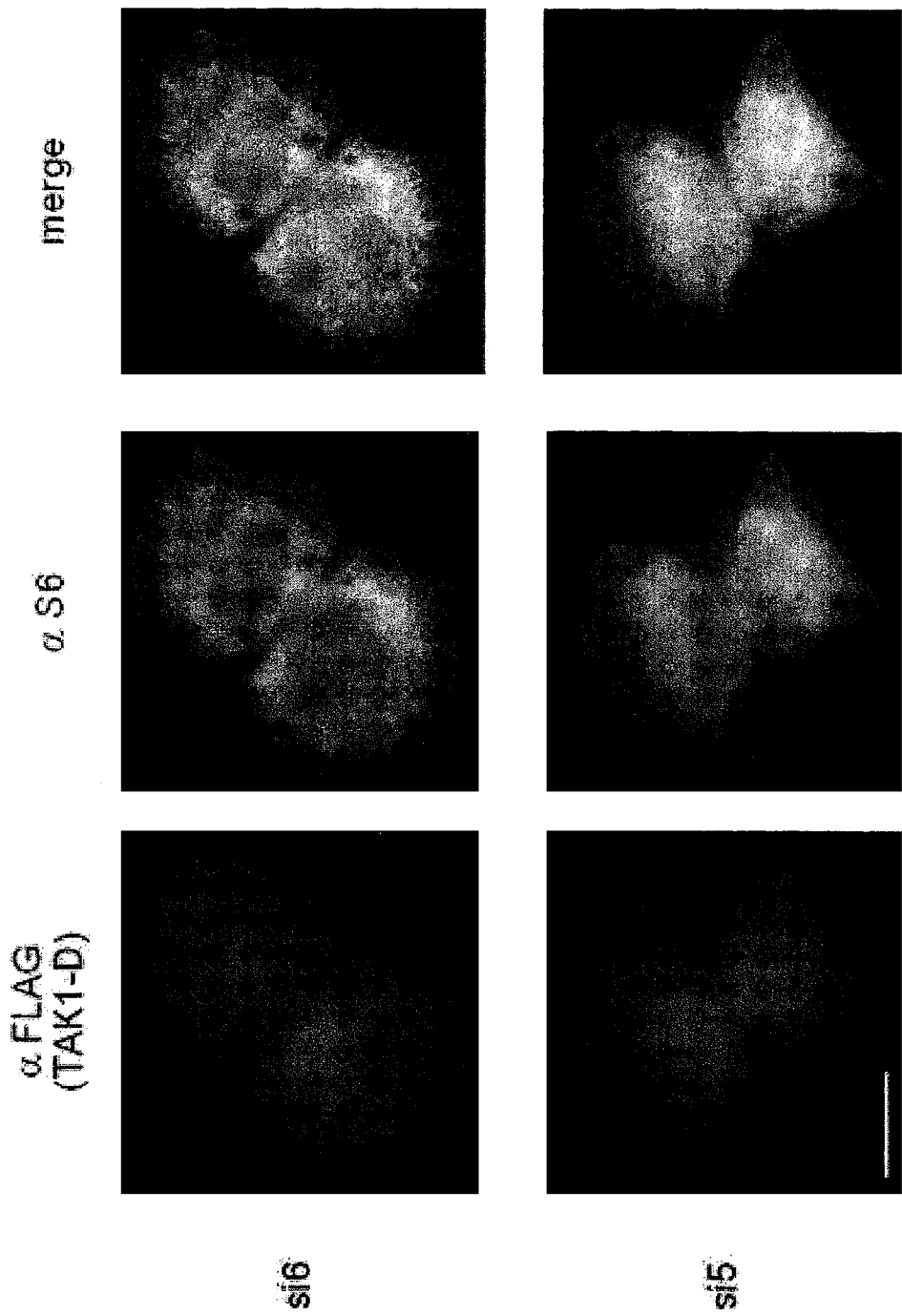
FIG. 19: Colocalization of FLAG tagged TAK1-D and the ribosomes after transfection with si5. H460 cells were permanently transfected with a plasmid coding for a cterminal TAK1-D FLAG fusion protein. Cells were fixed 6 h after treatment with dsRNA si5 and si6. FLAG-TAK1-D was detected using an anti-FLAG primary antibody and a Cy3 (red) labeled secondary antibody. Ribosomal protein S6 was detected using a S6 specific primary antibody and an Alexa Fluor 488 (green) conjugated secondary antibody. The right panels show the superposition of the TAK1-D and ribosomal fluorescence signals. Increased colocalization of TAK1-D and ribosomes after transfection with dsRNA si5 is visible by the increase of the yellow signal in the merged images. The scale bar has a length of 10 μm.

As the association of activated TAK1-D has been shown after cell lysis and separation of the organelles, it was tested whether this association could also be observed in intact cells. Immunofluorescence was used to detect a colocalization between TAK1-D and ribosomes. TAK1-D was detected by using a FLAG antibody to label transfected TAK1-D c-terminally fused to a FLAG tag. Ribosomes were detected using an antibody against the ribosomal protein S6. FIG. 19 shows in red the cytoplasmic and nuclear localization of the FLAG tagged TAK1-D protein 6 hours after treatment with dsRNA si5 or si6. In the same figure, the green panels show the cytoplasmic distribution of the ribosomes detected by ribosomal protein S6 staining. The panels on the right of FIG. 19 show the superposition of the TAK1-D and ribosomal signals. The increase of yellow colored pixels in si5 treated cells indicates the increased colocalization of TAK1-D and the ribosomes under these conditions. These data demonstrate that the binding of TAK1-D to 80S ribosomes after si56 treatment can also be observed in fixed intact cells.

Example 12

Binding of TAK1-D to the 80S Ribosome

To probe the extent of interaction between TAK1-D and the 80S ribosome, ribosomes were washed with different concentrations of KCl as described by Samuel (Samuel, 1981). This method separates proteins bound loosely to the ribosome in the 0.12 M KCl salt wash from proteins with a stronger ribosomal association like PKR (Samuel, 1981) in the 0.3 M and 0.8 M KCl fractions from the ribosomal core proteins still bound after the 0.8 M KCl washing step.

Figure 20:
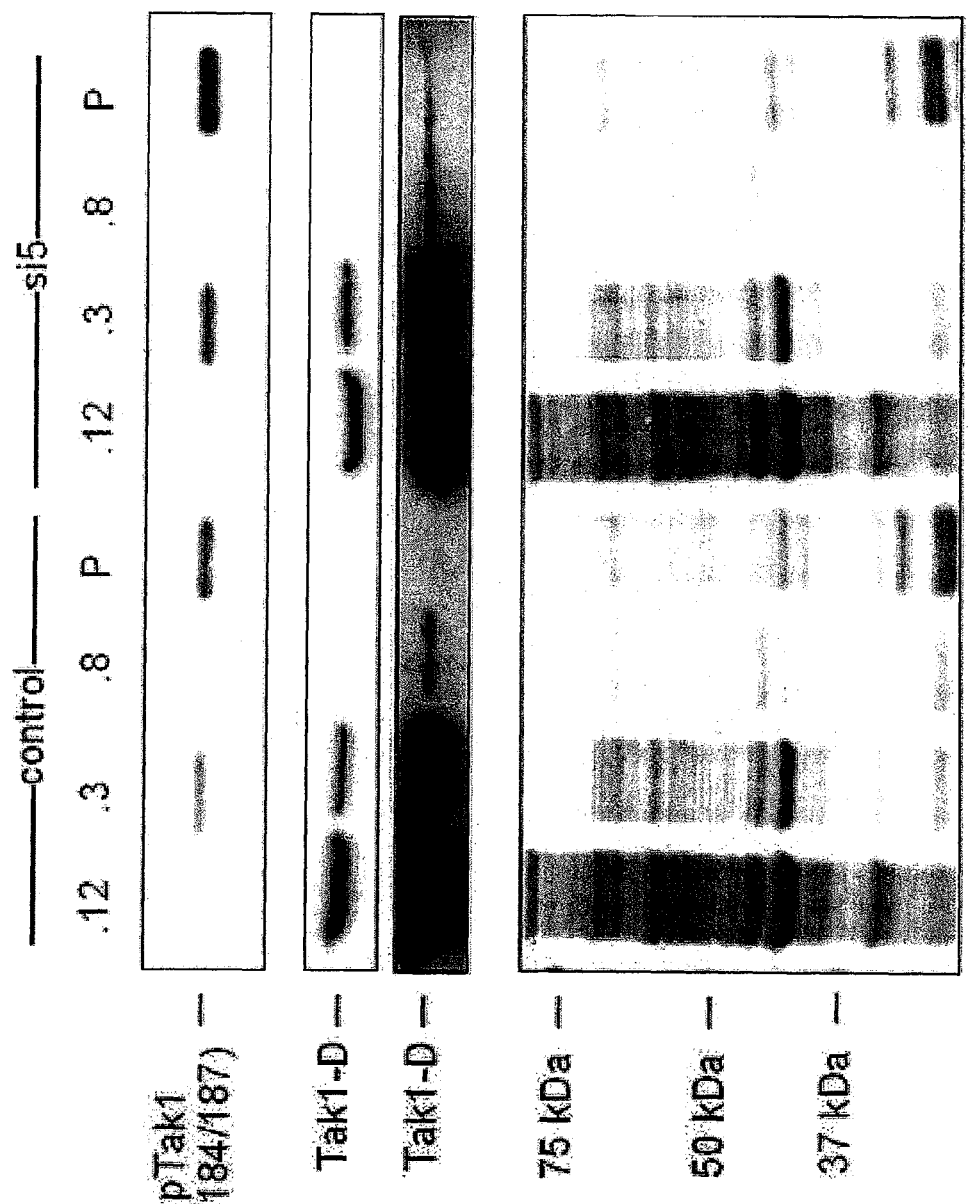
FIG. 20: Phosphorylated TAK1-D (T184/T187) is tightly associated with the ribosome. Ribosomal protein from untreated control and dsRNA si5 treated (4 h) H460 cells were separated by washing the ribosomes with increasing concentrations of KCl. The lanes contain the total protein found in the 0.12, 0.3, and 0.8 M KCl supernatants as well as the one found in the pellet (P) after the 0.8 M KCl wash. Phosphorylated TAK1-D could be found in the 0.3 M KCl wash and in the final pellet (P) (top panel). The two panels labeled TAK1-D show a normal and long film exposure of a TAK1-D immunoblot. Only very small amount of TAK1-D can be detected in the pellet (P) despite the strong phospho-TAK1-D signal detected in this fraction. The bottom panel shows the Ponceau S stained blotting membrane to demonstrate the amount of protein found in each fraction.

The Ponceau S stained PVDF membrane shown in the bottom panel of FIG. 20 demonstrates that most ribosome associated proteins dissociate from the ribosome in the presence of 0.12 M KCl. The same holds true for total TAK1-D protein, most of which can be found in the 0.12 M KCl wash fraction. The immunoblot in the top panel of FIG. 20 shows that no phosphorylation of this TAK1-D fraction could be detected on T184 and T187 in the activation loop of the kinase. T184/T187 phosphorylated TAK1-D was detectable in the 0.3 M KCl wash fraction which contains almost all of the total TAK1-D protein not dissociated by the 0.12 M KCl wash step. However, most of the T184/T187 phosphorylated TAK1-D still remained bound to be ribosome (P fraction) after washing it with 0.8 M KCl. As no total TAK1-D protein could be detected in this fraction in the standard immunoblot a prolonged exposure of the immunoblot to the film was performed, which is shown in the lower panel of FIG. 20 labeled TAK1-D. On this long exposure film a small amount of total TAK1-D protein can be seen in the ribosomal pellet after the 0.8M KCl wash. If the amount of TAK1-D protein and the amount of signal obtained with the phosphorylation specific antibody is compared between fraction 0.3 and P in FIG. 20 it can be concluded that a very high fraction of the tightly bound TAK1-D molecules is phosphorylated on the activating auto-phosphorylation sites T184 and T187.

Example 13 si5-Mediated Activation of TAK1-D is Associated with Inhibition of Translation

The tight association of phosphorylated TAK1-D with the ribosome leads to the question of whether dsRNA mediated activation of TAK1-D influences the function of the ribosome. To test this hypothesis the translational activity was measured in cultured cells by determining the incorporation of [$^{35}$S] methionine. FIG. 21A shows that [$^{35}$S] methionine incorporation was significantly reduced within 1 hour of transfection with dsRNA si5 and reached about 60% of its initial value after 4 hours. In contrast [35S] methionine incorporation remained unchanged after transfection of H460 cells with dsRNA si6.

To determine whether this translation inhibition affects all or just a subset of newly synthesized proteins, total protein from H460 cells was separated after [$^{35}$S] methionine pulse labeling by SDS-PAGE. FIG. 21B shows the total amount of protein visible in the gel after Coomassie Blue staining in the left panel as well as the autoradiographic detection of [$^{35}$S] methionine in the right panel. Similar to the results shown in panel A of the same figure, [$^{35}$S] methionine incorporation drops to about 50% of it initial value within the first 4 hours after transfection with dsRNA si5 and remains about constant at this level for up to 24 hours. No inhibition of translation was observed after transfection of dsRNA si6. It can be seen in the autoradiography, that although the total amount of incorporated [$^{35}$S] methionine is significantly reduced after treatment of the cells with dsRNA si5, the distribution of radiolabeled proteins at different molecular weights did not change when compared to untreated control cells. These findings indicate that there is no preferential post-transcriptional silencing but rather a global down regulation of translation affecting the synthesis of most or even all cellular proteins.

As it has been shown in FIGS. 16A and 16B that the transdominant-negative mutant of TAK1-D/K63W inhibits si5 triggered p38 MAP kinase and SAPK/JNK activation as well as apoptotic cell death, the question arises whether TAK1-D/K63W also inhibits si5 triggered down regulation of protein synthesis. To answer this question, protein synthesis was measured by [$^{35}$S] methionine incorporation 4 hours after transfection of wild-type, vector transfected, or TAK1-D/K63W transfected H460 cells. The results are shown in FIG. 21C. Again [$^{35}$S] methionine incorporation is given relative to the incorporation measured in untreated cells. FIG. 21C shows, that while si5 induced a significant reduction in mRNA translation in wild-type as well as in vector transfected cells, this reduction could not be observed in H460 cells transfected with TAK1-D/K63W. This further indicates the functional role of TAK1-D in dsRNA-mediated transcriptional shutdown and cell death.

The data presented demonstrate that a dsRNA of a specific sequence inhibits protein translation and triggers stress-activated protein kinase cascades leading to an activation of p38 MAP kinase and SAPK/JNK. This inhibition is dependent upon TAK1-D and its association with the 80S ribosome and subsequent translation inhibition. As many other agents have been shown to activate stress-activated protein kinase cascades in response to ribotoxic stress (Iordanov et al., 1997) it is interesting to ask whether TAK1-D activation is also associated with other types of ribotoxic stress.

Example 14

Figure 22:
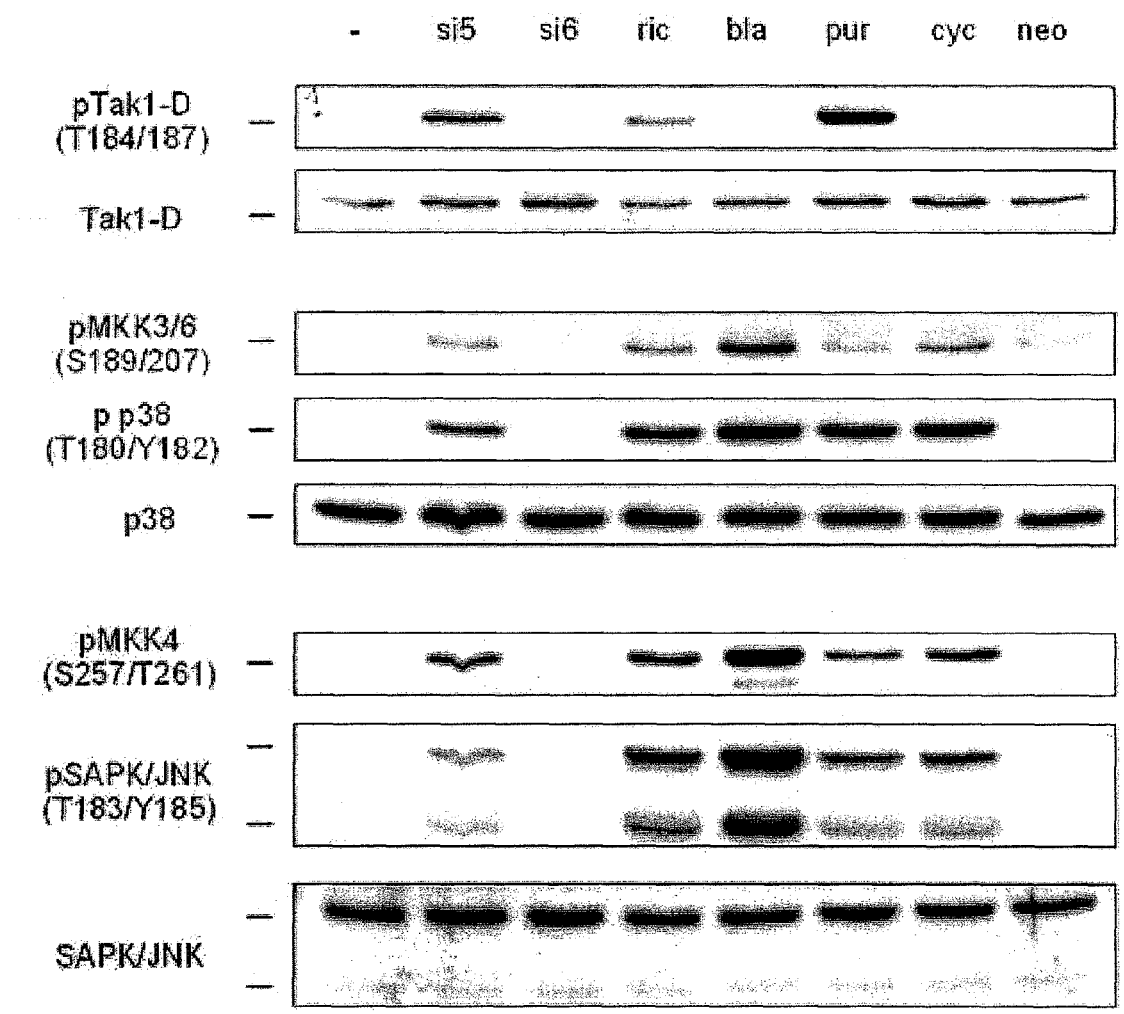
FIG. 22: Activating autophosphorylation of TAK1-D after other types of ribotoxic stress. H460 cells were treated as a control with 20 nM dsRNA si5 (si5) or si6 (si6) for 4 hours or with the following ribotoxins for 90 minutes: 9 μg/ml ricin A (ric), 100 μM blasticidin S (bla), 200 μM puromycin (pur), 25 μg/ml cycloheximide (cyc), and 1 mg/ml G418 (neo). Western blots using phosphorylation specific antibodies demonstrated that in addition to dsRNA si5 ricin A and puromycin induce an activating TAK1-D phosphorylation at T184 and T187. As blasticidin S and cycloheximide also induce an activation of p38 MAP kinase and SAPK/JNK the MAPKKK TAK1-D seems participate in signaling after special types of ribosomal stress.

Activating TAK1-D Autophosphorylation Also Occurs after Other Types of Ribotoxic Stress Five toxins and antibiotics, which are known inhibitors of protein synthesis in mammalian cells were tested for their ability to activate TAK1-D: Ricin A, Blasticidin S, Puromycin, Cycloheximide, and G418. FIG. 22 shows that these substances, with the exception of G418 induced activating phosphorylations of p38 MAP kinase and its upstream kinases MKK3/6 as well as SAPK/JNK and its upstream kinase MKK4. Interestingly, only Ricin A and Puromycin led to an activating autophosphorylation of TAK1-D on T184 and T187 despite their different molecular mechanisms. No such activation was detectable after treating the cells with Basticidin S and Cycloheximide. These findings indicate that TAK1-D seems not to be involved in a general ribotoxic stress response but in the signaling events in response to translation inhibition by selected substances like Ricin A, Puromycin, and dsRNA si5.

Example 15 dsRNAs do not Silence TLK1

Figure 23:
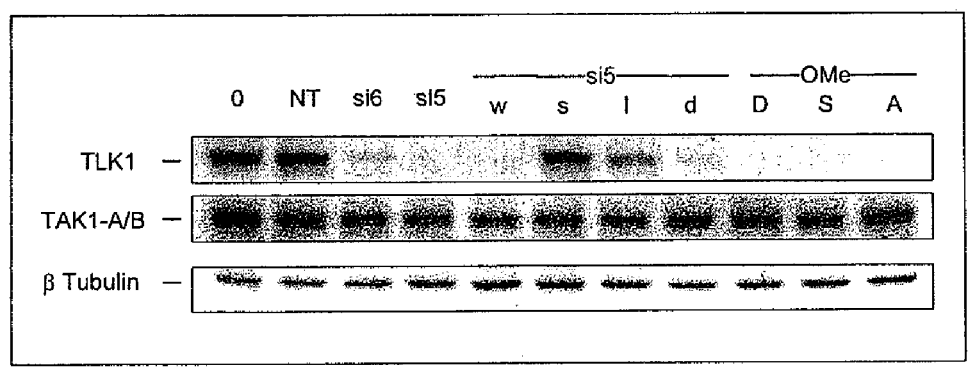
FIG. 23: Efficiency of dsRNAs to post-transcriptionally silence TLK1 expression.

In order to test whether dsRNA molecules show the same cellular uptake and stability the efficiency of these molecules to post-transcriptionally silence the expression of TLK1 was determined as si6 as well as si5 siRNA are directed against the mRNA of this protein. HeLa cells were used to test TLK1 silencing as these cells do not express TAK1-D and are therefore resistant to si5 induced cell death. FIG. 23 shows that 48 hours after transfection of HeLa cells with dsRNA si6, si5, si5w, si5d, si5OMeD, si5OMeS, and si5OMeA a very significant reduction in the expression of TLK1 can be observed due to RISC-AGO2 mediated mRNA degradation. The lack of post-transcriptional silencing of TLK1 after transfection with dsRNAs si5s and si5l can be explained by the insufficient homology of these molecules to the sequence of the TLK1 mRNA. As a loading control the unchanged expression levels of TAK1-A/B and 3-tubulin are shown in the two lower panels.

Example 16

Expression of TAK1-D in Human Non-Small Cell Lung Cancers

Figure 24:
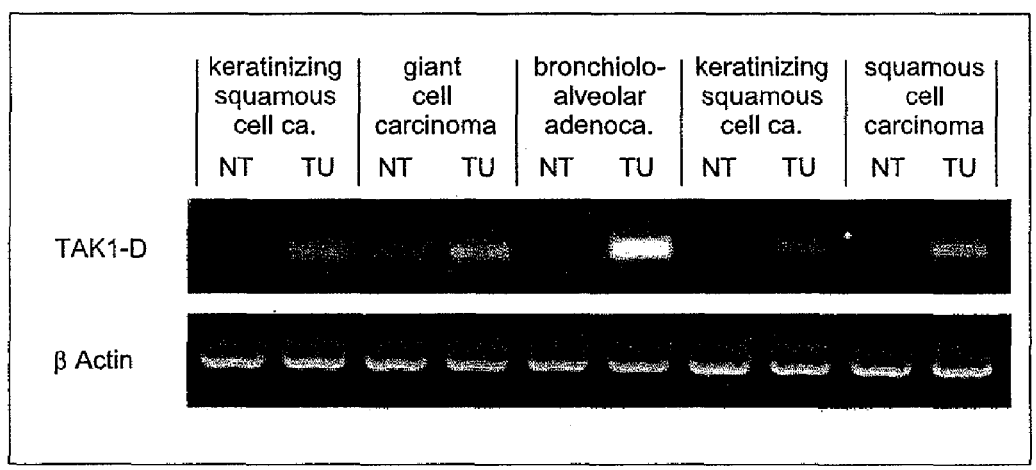
FIG. 24: Ethidium bromide stained agarose gel showing the PCR products obtained with TAK1-D specific primers from 5 matched NSCLC (TU) and normal tissue (NT) samples.

In order to analyze the expression of the splicing variant D of TAK1 in human NSCLC samples and in matched samples of normal lung tissue, cDNAs synthesized from patient specific tumors and normal lung tissue were purchased from a commercial source (Clontech). For each tumor and normal tissue sample 15 ng of cDNA was amplified in a 50 µl standard PCR reaction. For the amplification of TAK1-D cDNA the following primers were used: 5': ATCGCCGCAACCA-CAGGCAAC, 3' (SEQ ID NO:9): GTCCAGTTCTGCAAC-TAGTTCTTGCCTG (SEQ ID NO:10). The cycling conditions were: 35 cycles (94° C., 15 sec; 65° C., 30 sec; 72° C., 45 sec). The PCR products, which were 274 base pairs in length, were separated on an ethidium bromide stained agarose gel, shown in the upper panel of FIG. 24. The lower panel of FIG. 24 shows the amplification products of the β-actin cDNA as a control. It can be seen in the upper panel of FIG. 24 that all 5 tumor samples express TAK1-D. In addition in all samples a significantly higher expression of TAK1-D mRNA could be detected in the tumors when compared to matched normal tissue. These data demonstrate that TAK1-D is overexpressed in many if not all NSCLCs. Therefore the targeted activation of TAK1-D, which has been proposed in this application, might offer a novel and specific treatment strategy for NSCLCs.

Example 17

A Short Hairpin RNA Containing the si5 Sequence Induces Cell Death

Figure 25:
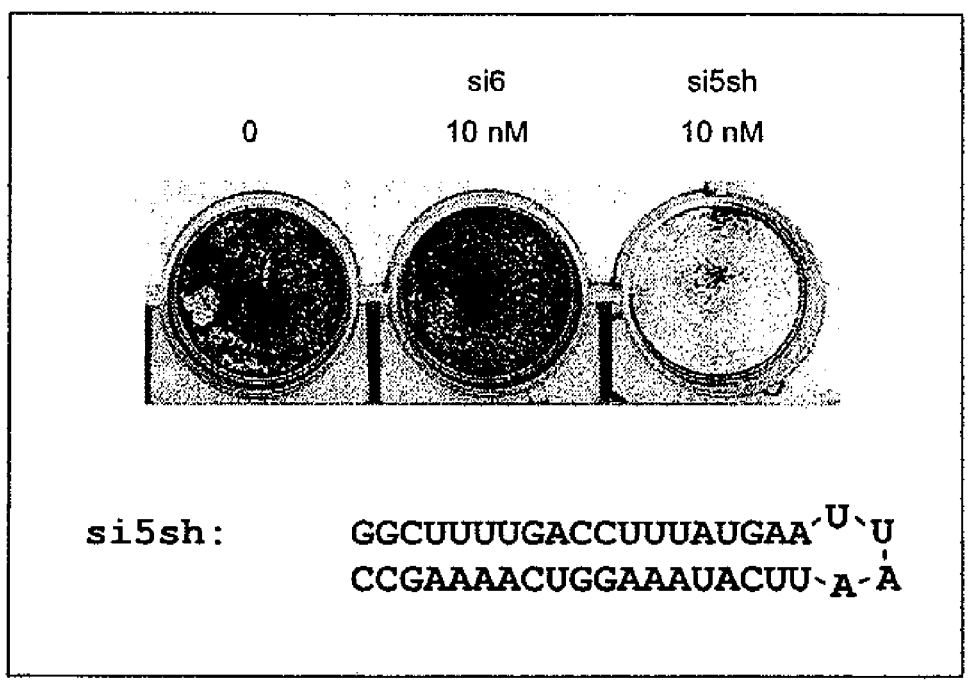
FIG. 25: Crystal Violet stained H460 cells 48 hours after transfection with control (si6) or shRNA si5h (SEQ ID NO:20).

With the intended development of a NSCLC treatment strategy in mind it is important to consider not only delivery strategies of chemically synthesized RNAs but also cellular expression of dsRNAs from DNA vectors. When considering intracellular expression it is the most common strategy to induce the transcription of a short hairpin RNA (shRNA) by a suitable promoter. Although the dsRNA modification experiments indicate that modifications at the 3' end of the sense strand, which are required to form a shRNA, do not interfere with the TAK1-D activating activity of the molecule, an experimental proof is desirable. Therefore, a shRNA was synthesized by in vitro transcription from a chemically synthesized double-stranded DNA molecule using T7 RNA polymerase. The si5-related sequence of this molecule is shown in the lower panel of FIG. 25. Transfection of this molecule into H460 cells led to cell death within 48 hours as shown in the upper panel of FIG. 25. In contrast, no cell death or growth inhibition could be observed after transfection of the control dsRNA si6. Thus, it can be concluded that cellular expression of shRNAs represent an effective and alternative approach to trigger cell death by TAK1-D activation.

Example 18 dsRNA Induces Growth Delay in a Human Xenograft Tumor In Vivo

Figure 26:
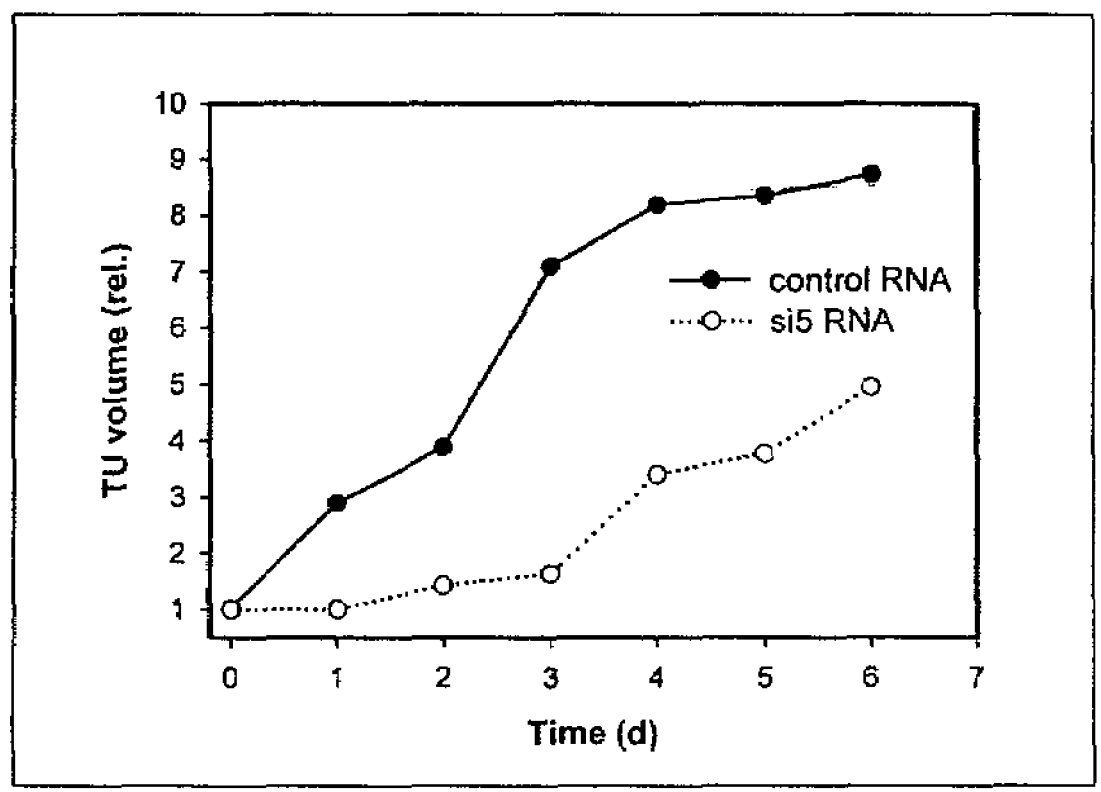
FIG. 26: Tumor growth curves of H460 xenograft tumors injected with control RNA or dsRNA si5.

In order to test whether the proposed treatment approach for NSCLC using dsRNA-mediated activation of TAK1-D is feasible in vivo H460 xenograft tumors grown in athymic NCr nu/nu mice were treated with by intratumoral injection of a liposomal dsRNA preparation. About 10 days after subcutaneous injection of 106 H460 cells into the left hind leg of the animals tumors had reached a volume of about 300 µl and were injected with 50 µl of liposomal control RNA or active RNA si5. Liposomes consisting of DOTAP and Cholesterol (1:1) were prepared by sonication and extrusion. RNA was bound to the polycation protamine and liposome/polycation/RNA nanoparticles were prepared by mixing the protamine RNA complex with the liposomes. Finally 4 µg of RNA were injected in a volume of 50 µl on day 0 and 1. FIG. 26 shows the tumor growth kinetics observed after injection of active and control RNA. The tumor growth delay seen after the injection of dsRNA si5 demonstrates that dsRNA mediated activation of TAK1-D can be used to inhibit tumor growth in vivo. In addition to the observed growth delay it is important to note that no sign of normal tissue toxicity like necrosis of the skin or the tumor vascular system could be observed, indicating that the tumor cell specificity shown is not only an in vitro phenomenon.

To gain an insight into the mechanisms of dsRNA si5-induced growth delay in H460 xenograft tumors shown in FIG. 26, the tumors were analyzed by immunohistochemical staining for apoptotic activation of Caspase-3. Two tumors with a volume of about 500 µl were injected with a liposomal preparation of active and control dsRNA as described above. Sixteen hours after injection mice were sacrificed and the tumors were fixed in formaldehyde. After paraffin embedding 5 µm sections were cut from the central region of the tumor. The sections were stained immunohistochemically using a primary antibody against cleaved Caspase-3. The primary antibody was detected using a biotinylated secondary antibody and an peroxidase ABC-Kit (Vector Laboratories). Diaminobenzidine (DAB) was used as a substrate for immunohistochemical detection and the slides were counterstained with Hematoxylin. The brownish DAB reaction product, indicating apoptotic activation of Caspase-3, is visible in many cells in the sections obtained from tumors, which have been injected with the active dsRNA si5. In contrast almost no Caspase-3 activation can be seen in the sections obtained from inactive control dsRNA injected tumors. This indicates that dsRNA si5 induces apoptotic cell death in H460 xenograft tumors in vivo similar to the apoptotic response of H460 cells to dsRNA si5 observed in cell culture.

All of the methods and apparatus disclosed and claimed herein can be made and executed without undue experimentation in light of the present disclosure. While the compositions and methods of this invention have been described in terms of particular embodiments, it will be apparent to those of skill in the art that variations may be applied to the methods and apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

H. References

The following references, to the extent that they provide exemplary procedural or other details supplementary to those set forth herein, are specifically incorporated herein by reference.

U.S. Pat. No. 4,415,723
U.S. Pat. No. 4,458,066
U.S. Pat. No. 4,659,774
U.S. Pat. No. 4,682,195
U.S. Pat. No. 4,683,202
U.S. Pat. No. 4,797,368
U.S. Pat. No. 4,816,571
U.S. Pat. No. 4,959,463
U.S. Pat. No. 5,139,941
U.S. Pat. No. 5,141,813
U.S. Pat. No. 5,187,260
U.S. Pat. No. 5,214,136
U.S. Pat. No. 5,223,618
U.S. Pat. No. 5,264,566
U.S. Pat. No. 5,378,825
U.S. Pat. No. 5,428,148
U.S. Pat. No. 5,446,137
U.S. Pat. No. 5,466,786
U.S. Pat. No. 5,470,967
U.S. Pat. No. 5,543,328
U.S. Pat. No. 5,554,744
U.S. Pat. No. 5,559,099
U.S. Pat. No. 5,574,146
U.S. Pat. No. 5,602,240
U.S. Pat. No. 5,602,244
U.S. Pat. No. 5,610,289
U.S. Pat. No. 5,614,617
U.S. Pat. No. 5,623,070
U.S. Pat. No. 5,645,897
U.S. Pat. No. 5,652,099
U.S. Pat. No. 5,670,663
U.S. Pat. No. 5,672,344
U.S. Pat. No. 5,672,697
U.S. Pat. No. 5,681,947
U.S. Pat. No. 5,700,922
U.S. Pat. No. 5,705,629
U.S. Pat. No. 5,708,154
U.S. Pat. No. 5,714,606
U.S. Pat. No. 5,739,169
U.S. Pat. No. 5,763,167
U.S. Pat. No. 5,777,092
U.S. Pat. No. 5,792,847
U.S. Pat. No. 5,795,715
U.S. Pat. No. 5,801,005
U.S. Pat. No. 5,824,311
U.S. Pat. No. 5,830,880
U.S. Pat. No. 5,846,945
U.S. Pat. No. 5,858,988
U.S. Pat. No. 5,859,221
U.S. Pat. No. 5,872,232
U.S. Pat. No. 5,886,165
U.S. Pat. No. 5,889,136
U.S. Pat. No. 6,506,559
U.S. Pat. No. 6,573,099
U.S. Pat. No. 6,740,511
U.S. Pat. No. 7,235,233
U.S. patent application Ser. No. 09/351,778
U.S. patent application Ser. No. 09/575,473
U.S. Publication Ser. No. 10/391,068
U.S. Publication No. 2002/0168707
U.S. Publication No. 2002/0028785
U.S. Publication No. 2003/0051263
U.S. Publication No. 2003/0055020
U.S. Publication No. 2003/0159161
U.S. Publication No. 20030147966
U.S. Publication No. 20030223938
U.S. Publication No. 2004/0064842
U.S. Publication No. 2004/0265839
U.S. Publication No. 20040213764
U.S. Publication No. 20050143336
U.S. Publication No. 20060002893

Aksentijevich et al., *Hum. Gene Ther.*, 7(9):1111-1122, 1996.
Alexopoulou et al., *Nature*, 413:732-738, 2001.
Austin-Ward and Villaseca, *Revista Medica de Chile*, 126(7): 838-845, 1998.
Ausubel et al., In: *Current Protocols in Molecular Biology*, John, Wiley & Sons, Inc, New York, 1996.
Bakhshi et al., *Cell*, 41(3):899-906, 1985.
Bosher and Labouesse, *Nat. Cell. Biol.*, 2(2):E31-E36, 2000.
Brown et al., *J. Mol. Biol.*, 354(5):1013-1020, 2005.
Brummelkamp et al., *Science*, 296(5567):550-553, 2002.
Bukowski et al., *Clinical Cancer Res.*, 4(10):2337-2347, 1998.
Bulavin et al., *Nature*, 411(6833):102-107, 2001.
Cans et al., *Mol. Biol. Rep.*, 26:53-57, 1999.
Chada et al., *Mol. Ther.*, 7:S446, 2003.
Chang et al., *Hepatology*, 14:134A, 1991.
Christodoulides et al., *Microbiology*, 144(Pt 11):3027-3037, 1998.
Clark et al., *Hum. Gene Ther.*, 6(10):1329-1341, 1995.
Cleary and Sklar, *Proc. Natl. Acad. Sci. USA*, 82(21):7439-7443, 1985.
Cleary et al., *J. Exp. Med.*, 164(1):315-320, 1986.
Coffin, In: *Virology*, Fields et al. (Eds.), Raven Press, NY, 1437-1500, 1990.
Collins, *Biotechniques*, 43:25-30, 2007.
Davidson et al., *J. Immunother.*, 21(5):389-398, 1998.
Davis et al., *J. Virol.*, 70(6):3781-3787, 1996.
de Haro et al., *FASEB J.*, 10: 1378-1387, 1996.
Dempsey et al., *Biochim. Biophys. Acta*, 1517(1):46-52, 2000.
Edlund et al., *Mol. Biol. Cell*, 14(2):529-544, 2003.
Elbashir et al., *Nature*, 411(6836):494-498, 2001.
Elroy-Stein et al., *Proc. Natl. Acad. Sci. USA*, 86(16):6126-6130, 1989.
EP 266,032
Felgner et al., *Proc. Natl. Acad. Sci. USA*, 84(21):7413-7417, 1987.
Fire et al., *Nature*, 391(6669):806-811, 1998.
Flotte et al., *Am. J. Respir. Cell Mol. Biol.*, 7(3):349-356, 1992.
Flotte et al., *Proc. Natl. Acad. Sci. USA*, 90(22):10613-10617, 1993.
Flotte, et al., *Gene Ther.*, 2(1):29-37, 1995.
Fraley et al., *Proc. Natl. Acad. Sci. USA*, 76:3348-3352, 1979.
Froehler et al., *Nucleic Acids Res.*, 14(13):5399-5407, 1986.
Gabizon et al., *Cancer Res.*, 50(19):6371-6378, 1990.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Glorioso et al., *Mol. Biotechnol.*, 4(1):87-99, 1995.
Goss et al., *Cell Signal*, 15(7):709-718, 2003.
Grishok et al., *Science*, 287:2494-2497, 2000.
Hanibuchi et al., *Int. J. Cancer*, 78(4):480-485, 1998.
Hellstrand et al., *Acta Oncologica*, 37(4):347-353, 1998.
Hermonat and Muzycska, *Proc. Natl. Acad. Sci. USA*, 81:6466-6470, 1984.
Hiscott et al., *Oncogene*, 25:6844-6867, 2006.

Horwich et al., *J. Virol.*, 64:642-650, 1990.
Hui and Hashimoto, *Infection Immun.*, 66(11):5329-5336, 1998.
Inouye and Inouye, *Nucleic Acids Res.*, 13:3101-3109, 1985.
Iordanov et al., *Mol. Cell. Biol.*, 17:3373-3381, 1997.
Jiang et al., *J. Biol. Chem.*, 278:16713-16719, 2003.
Jiang et al., *Mol. Cell. Biol.*, 22(20):7158-7167, 2002.
Ju et al., *Gene Ther.*, 7(19):1672-1679, 2000.
Judge et al., *Mol. Ther.*, 13(3):494-505, 2006.
Judge et al., *Nat. Biotechnol.*, 23:457-462, 2005.
Kaneda et al., *Science*, 243:375-378, 1989.
Kaplitt et al., *Nat. Genet.*, 8(2):148-154, 1994.
Karlsson et al., *EMBO J.*, 5:2377-2385, 1986.
Kato et al., *J. Biol. Chem.*, 266:3361-3364, 1991.
Kerr et al., *Br. J. Cancer*, 26(4):239-257, 1972.
Ketting et al., *Cell*, 99(2):133-141, 1999.
Kodym et al., *Radiat. Res.*, 169:46-58, 2008a.
Kodym et al., *RNA*, 14:535-542, 2008b.
Kornberg and Baker, *DNA Replication*, 2nd Ed., Freeman, San Francisco, 1992.
Kuma et al., *J. Biol. Chem.*, 280:19472-19479, 2005.
Kurland et al., *J. Biol. Chem.*, 276(48):45380-45386, 2001.
LaFace et al., *Virology*, 162(2):483-486, 1988.
Landt et al., *Gene*, 96:125-128, 1990.
Laughlin et al., *J. Virol.*, 60(2):515-524, 1986.
Lebkowski et al., *Mol. Cell. Biol.*, 8(10):3988-3996, 1988.
Lee et al., *Biochim. Biophys. Acta*, 1582:175-177, 2002.
Lin and Avery, *Nature*, 402:128-129, 1999.
Liu et al., *Cancer Res.*, 55(14):3117-3122, 1995.
Lu et al., *Cancer Res.*, 66(2):1052-1061, 2006.
Mann et al., *Cell*, 33:153-159, 1983.
McCarty et al., *J. Virol.*, 65(6):2936-2945, 1991.
McLaughlin et al., *J. Virol.*, 62(6):1963-1973, 1988.
Mitchell et al., *Ann. NY Acad. Sci.*, 690:153-166, 1993.
Mitchell et al., *J. Clin. Oncol.*, 8(5):856-869, 1990.
Miyagishi et al., *Nature Biotechnol.*, 19:497-500, 2002.
Montgomery et al., *Proc. Natl. Acad. Sci. USA*, 95:15502-15507, 1998.
Morton et al., *Arch. Surg.*, 127:392-399, 1992.
Muzyczka, *Curr. Topics Microbiol. Immunol.*, 158:97-129, 1992.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Ninomiya-Tsuji et al., *Nature*, 398(6724):252-256, 1999.
Ohi et al., *Gene*, 89(2):279-282, 1990.
Paddison et al. *Genes Dev.*, 16(8):948-958, 2002.
Paskind et al., *Virology*, 67:242-248, 1975.
Paul et al., *Nature Biotechnol.*, 20:505-508, 2002.
Paul, *Immunology*, Chap. 27 and 29, 3$^{rd}$ Ed., Raven Press, NY, 1993.
PCT Appln. WO 00/44914
PCT Appln. WO 01/36646
PCT Appln. WO 01/68836
PCT Appln. WO 02/08436
PCT Appln. WO 02/31168
PCT Appln. WO 02/85287
PCT Appln. WO 03/33029
PCT Appln. WO 98/07408
PCT Appln. WO 99/32619
Pietras et al., *Oncogene*, 17(17):2235-2249, 1998.
Player and Torrence, *Pharmacol. Ther.*, 78:55-113, 1998.
Qin et al., *Proc. Natl. Acad. Sci. USA*, 95(24):14411-14416, 1998.
Ravindranath and Morton, *Intern. Rev. Immunol.*, 7: 303-329, 1991.
Rosenberg et al., *Ann. Surg.* 210(4):474-548, 1989.
Rosenberg et al., *N. Engl. J. Med.*, 319:1676, 1988.
Roux et al., *Proc. Natl. Acad. Sci. USA*, 86:9079-9083, 1989.
Sakurai et al., *Biochem. Biophys. Res. Commun.*, 297:1277-1281, 2002.
Sakurai et al., *FEBS Lett.*, 474(2-3):141-145, 2000.
Sambrook et al., In: *Molecular cloning*, Cold Spring Harbor Laboratory Press, Cold Spring Harbor, N.Y., 2001
Samuel, *Methods Enzymol.*, 79(Pt B):168-178, 1981.
Samulski et al., *J. Virol.*, 63:3822-3828, 1989.
Scacheri et al., *Proc. Natl. Acad. Sci. USA*, 101:1892-1897, 2004.
Scheit, In: *Synthesis and Biological Function*, Wiley-Interscience, NY, 171-172, 1980.
Sharp and Zamore, *Science*, 287:2431-2433, 2000.
Sharp, *Genes Dev.*, 13:139-141, 1999.
Shelling and Smith, *Gene Therapy*, 1:165-169, 1994.
Singhirunnusorn et al., *J. Biol. Chem.*, 280:7359-7368, 2005.
Sledz et al., *Nat. Cell Biol.*, 5:834-839, 2003.
Smith and Moss, *Gene*, 25(1):21-28, 1983.
Smyth-Templeton et al., *DNA Cell Biol.*, 21(12):857-867, 1997.
Solodin et al., *Biochemistry*, 34(41):13537-13544, 1995.
Sui et al., *Proc. Natl. Acad. Sci. USA*, 99(8):5515-5520, 2002.
Tabara et al., *Cell*, 99(2):123-132, 1999.
Tang, *Trends Biochem. Sci.*, 30:106-114, 2004.
Temin, In: *Gene Transfer*, Kucherlapati (Ed.), NY, Plenum Press, 149-188, 1986.
Templeton et al., *Nat. Biotechnol.*, 15(7):647-652, 1997.
Thierry et al., *Proc. Natl. Acad. Sci. USA*, 92(21):9742-9746, 1995.
Tratschin et al., *Mol. Cell. Biol.*, 4:2072-2081, 1984.
Tratschin et al., *Mol. Cell. Biol.*, 5:3258-3260, 1985.
Tsujimoto and Croce, *Proc. Natl. Acad. Sci. USA*, 83(14):5214-5218, 1986.
Tsujimoto et al., *Nature*, 315:340-343, 1985.
Tsujimoto et al., *Science*, 228(4706):1440-1443, 1985.
Tsukamoto et al., *Nat. Genet.*, 9(3):243-248, 1995.
Wall and Shi, *Lancet*, 362:1401-1403, 2003.
Walsh et al., *J. Clin. Invest*, 94:1440-1448, 1994.
Wei et al., *Gene Therapy*, 1:261-268, 1994.
Wincott et al., *Nucleic Acids Res.*, 23(14):2677-2684, 1995.
Wistuba et al., *Clin. Cancer Res.*, 5(5):991-1000, 1999.
Wong et al., *Gene*, 10:87-94, 1980.
Yang and Huang, *Gene Therapy*, 4 (9):950-960, 1997.
Yang et al., *J. Virol.*, 68:4847-4856, 1994.
Yoder et al., *Bio/Technology* 12:263-268, 1994.
Yu et al., *J. Am. Chem. Soc.*, 124(23):6576-6583, 2002.
Zamanian et al., *Mol. Cell. Biol.*, 20:1278-1290, 2000.
Zhao et al., *Proc. Natl. Acad. Sci. USA*, 99:14795-14800, 2002.
Zhou et al., *J. Exp. Med.*, 179:1867-1875, 1994.
Zhou et al., *Nature*, 361(6412):543-547, 1993.
Zhu et al., *Science*, 261(5118):209-211, 1993.

What is claimed is:

1. A method of inducing apoptosis and/or cell cycle arrest in a lung cancer cell that expresses Tak1-D comprising contacting said cell with a double-stranded (ds) RNA directed to an mRNA for TLK1, wherein said dsRNA has the sequence NC(A/U)(A/U)(A/U)(A/U)GAX$_{4-6}$AUGAN, wherein in N is any base or null and X is any base, GGCUUUUGACCUUUAUGAA (SEQ ID NO: 1), CCAAAAGAAGAUGUGAUGA (SEQ ID NO:6), 5'-GGCUUUUGACCUUUAUGAAU-U (SEQ ID NO:7) or 3'-CCGAAAACUGGAAAUACUUA-A (SEQ ID NO:8).

2. The method of claim 1, wherein said dsRNA is encapsulated in a lipid vehicle.

3. The method of claim 1, wherein said cancer cell is a metastatic cancer cell, a recurrent cancer cell, a multi-drug resistant cancer cell.

4. The method of claim 1, further comprising contacting said cell with a second apoptosis-inducing agent.

5. The method of claim 4, wherein said second apoptosis-inducing agent is a chemotherapeutic, radiation, or a polypeptide inducer of apoptosis.

6. A method of treating a subject with lung cancer, cells of which express Tak 1-D, comprising administering to said subject a double-stranded (ds) RNA directed to an mRNA for TLK1, wherein said dsRNA has the sequence NC(A/U)(A/U)(A/U)(A/U)GAX$_{4-6}$AUGAN, wherein in N is any base or null and X is any base, GGCUUUUGACCUUUAUGAA (SEQ ID NO: 1), CCAAAAGAAGAUGUGAUGA (SEQ ID NO:6), or 5'-GGCUUUUGACCUUUAUGAAU-U (SEQ ID NO:7) or 3'-CCGAAAACUGGAAAUACUUA-A (SEQ ID NO:8).

7. The method of claim 6, wherein said dsRNA is encapsulated in a lipid vehicle.

8. The method of claim 6, wherein said cancer is metastatic cancer, recurrent cancer, or a multi-drug resistant cancer cell.

9. The method of claim 6, further comprising contacting said cell with a second apoptosis-inducing agent.

10. The method of claim 9, wherein said second apoptosis-inducing agent is a chemotherapeutic, radiation, or a polypeptide inducer of apoptosis.

11. The method of claim 6, wherein said dsRNA is administered intratumorally, into tumor vasculature, loco-regional to a tumor, or systemically.

\* \* \* \* \*

UNITED STATES PATENT AND TRADEMARK OFFICE
CERTIFICATE OF CORRECTION

| | |
|---|---|
| PATENT NO. | : 8,163,709 B2 |
| APPLICATION NO. | : 12/361311 |
| DATED | : April 24, 2012 |
| INVENTOR(S) | : Reinhard Kodym et al. |

It is certified that error appears in the above-identified patent and that said Letters Patent is hereby corrected as shown below:

In claim 6, column 64, lines 12-13, delete "NC(A/U)(A/U)(A/U)(A/U)GAX$_4$-6AUGAN" and insert --NC(A/U)(A/U)(A/U)(A/U)GAX$_{4-6}$AUGAN-- therefor.

Signed and Sealed this
Third Day of July, 2012

David J. Kappos
*Director of the United States Patent and Trademark Office*